United States Patent
Ye et al.

(10) Patent No.: US 9,422,598 B2
(45) Date of Patent: Aug. 23, 2016

(54) METHOD AND KIT FOR THE PROGNOSIS OF COLORECTAL CANCER

(75) Inventors: Xun Ye, Shanghai (CN); Fei Wu, Shanghai (CN); Qinghua Xu, Hangzhou (CN); Xia Meng, Shanghai (CN); Bruno Mougin, Lyons (FR); Fang Liu, Shanghai (CN)

(73) Assignee: BIOMERIEUX, Marcy l'Etoile (FR)

( * ) Notice: Subject to any disclaimer, the term of this patent is extended or adjusted under 35 U.S.C. 154(b) by 287 days.

(21) Appl. No.: 13/698,219

(22) PCT Filed: Jun. 4, 2010

(86) PCT No.: PCT/EP2010/057843
§ 371 (c)(1),
(2), (4) Date: Nov. 15, 2012

(87) PCT Pub. No.: WO2011/150976
PCT Pub. Date: Dec. 8, 2011

(65) Prior Publication Data
US 2013/0072401 A1    Mar. 21, 2013

(51) Int. Cl.
C07H 21/04        (2006.01)
C12Q 1/68         (2006.01)
C40B 40/06        (2006.01)

(52) U.S. Cl.
CPC .......... *C12Q 1/6837* (2013.01); *C12Q 1/6886* (2013.01); *C40B 40/06* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,672,040 A | 6/1987 | Josephson |
| 4,683,195 A | 7/1987 | Mullis et al. |
| 4,683,202 A | 7/1987 | Mullis |

(Continued)

FOREIGN PATENT DOCUMENTS

| | | |
|---|---|---|
| CN | 101068936 A | 11/2007 |
| CN | 101111604 A | 1/2008 |

(Continued)

OTHER PUBLICATIONS

Killer Cell Lectin-Like Receptor Subfamily K, Member 1. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=KLRK1>.*

(Continued)

*Primary Examiner* — Jeanine A Goldberg
(74) *Attorney, Agent, or Firm* — Oliff PLC

(57) ABSTRACT

A method and kit for the prognosis of colorectal cancer where the method includes the steps of: a) obtaining a peripheral blood sample and extracting total RNA from the sample, b) contacting the total RNA with at least one reagent specific for at least one NK cell gene and no more than 25 specific reagents for 25 NK cell genes, c) determining the expression level of at least one and at most 25 NK cell genes to obtain an expression profile for the patient, d) analyzing the expression profile with expression profiles previously clinically classified as a good prognosis and as a poor prognosis, wherein if the expression profile is clustered with the poor prognosis profiles, then the patient is determined to have a poor prognosis, and if the expression profile is clustered with the good prognosis profiles, then the patient is determined to have a good prognosis.

15 Claims, 1 Drawing Sheet

(56) References Cited

U.S. PATENT DOCUMENTS

| | | | |
|---|---|---|---|
| 4,800,159 | A | 1/1989 | Mullis et al. |
| 4,981,783 | A | 1/1991 | Augenlicht |
| 5,234,809 | A | 8/1993 | Boom et al. |
| 5,399,491 | A | 3/1995 | Kacian et al. |
| 5,445,934 | A | 8/1995 | Fodor et al. |
| 5,700,637 | A | 12/1997 | Southern |
| 5,744,305 | A | 4/1998 | Fodor et al. |
| 5,750,338 | A | 5/1998 | Collins et al. |
| 5,807,522 | A | 9/1998 | Brown et al. |
| 2004/0002082 | A1 | 1/2004 | Feinberg |
| 2004/0033516 | A1 | 2/2004 | Mougin |
| 2004/0265230 | A1 | 12/2004 | Martinez et al. |
| 2005/0130170 | A1* | 6/2005 | Harvey et al. ............. 435/6 |
| 2005/0287544 | A1* | 12/2005 | Bertucci ............. C12Q 1/6886 435/6.12 |
| 2008/0311574 | A1* | 12/2008 | Manne et al. ............. 435/6 |
| 2011/0117083 | A1* | 5/2011 | Bais ............. C12Q 1/6883 424/133.1 |

FOREIGN PATENT DOCUMENTS

| | | |
|---|---|---|
| EP | 0 201 184 A2 | 12/1986 |
| EP | 2 169 078 A1 | 3/2010 |
| EP | 2 177 615 A1 | 4/2010 |
| FR | 14.691 | 1/1912 |
| FR | 14.896 | 3/1912 |
| FR | 2 780 059 A1 | 12/1999 |
| FR | 2 816 711 A1 | 5/2002 |
| FR | 2 816 958 A1 | 5/2002 |
| WO | WO 89/10977 A1 | 11/1989 |
| WO | WO 90/01069 A1 | 2/1990 |
| WO | WO 90/03382 A1 | 4/1990 |
| WO | WO 90/06995 A1 | 6/1990 |
| WO | WO 91/02818 A1 | 3/1991 |
| WO | WO 91/19812 A1 | 12/1991 |
| WO | WO 94/12670 A2 | 6/1994 |
| WO | WO 97/45202 A1 | 12/1997 |
| WO | WO 99/15321 A1 | 4/1999 |
| WO | WO 99/35500 A1 | 7/1999 |
| WO | WO 99/53304 A1 | 10/1999 |
| WO | WO 99/65926 A1 | 12/1999 |
| WO | WO 00/05338 A1 | 2/2000 |
| WO | WO 00/71750 A1 | 11/2000 |
| WO | WO 01/44506 A1 | 6/2001 |
| WO | WO 01/44507 A1 | 6/2001 |
| WO | 02/40711 A1 | 5/2002 |
| WO | WO 02/090319 A1 | 11/2002 |
| WO | WO 02/090584 A2 | 11/2002 |
| WO | WO 2005/054508 A2 | 6/2005 |
| WO | WO 2009/049228 A2 | 4/2009 |
| WO | WO 2009/126804 A2 | 10/2009 |
| WO | WO 2010/040571 A2 | 4/2010 |
| WO | WO 2010/056374 A2 | 5/2010 |

OTHER PUBLICATIONS

Killer Cell Lectin-Like Receptor Subfamily B, Member 1. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=KLRB1>.*

Granzyme B (Granzyme 2, Cytotoxic T-Lymphocyte-Associated Serine Esterase 1). Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=GZMB>.*

Related RAS Viral (R-Ras) Oncogene Homolog 2. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=RRAS2>.*

Querying HG U133 Plus 2.0 array probe set for gene symbols. Query results [online]. Affymetrix, 2014 [retrieved on Nov. 13, 2014]. Retrieved from the Internet: <https://www.affymetrix.com/analysis/netaffx/showresults.affx>.*

Irizarry, R.A. et al., "Exploration, normalization, and summaries of high density oligonucleotide array probe level data," *Biostatistics*, 2003, pp. 249-264, vol. 4, No. 2.

Johnson, W.E. et al., "Adjusting batch effects in microarray expression data using empirical Bayes methods," *Biostatistics*, 2007, pp. 118-127, vol. 8, No. 1.

Tusher, V.G. et al., "Significance analysis of microarrays applied to the ionizing radiation response," *PNAS*, Apr. 24, 2001, pp. 5116-5121, vol. 98, No. 9.

Abstract of ComBat: 'Combating' Batch Effects When Combining Batches of Gene Expression Microarray Data, obtained from http://www.bu.edu/jlab/wp-assetsComBat/Abstract.html on Feb. 14, 2013.

Nielsen, P.E. et al., "Sequence-Selective Recognition of DNA by Strand Displacement with a Thymine-Substituted Polyamide," *Science*, Dec. 6, 1991. pp. 1497-1500, vol. 254.

Kricka, L.J., "Nucleic Acid Detection Technologies-Labels, Strategies, and Formats," *Clinical Chemistry*, 1999, pp. 453-458, vol. 45, No. 4.

Chef, M. et al., "Accessing Genetic Information with High-Density DNA Arrays," *Science*, Oct. 25, 1996, pp. 610-614, vol. 274.

Pease, A.C. et al., "Light-generated oligonucleotide arrays for rapid DNA sequence analysis," *Proc. Natl. Acad. Sci. USA*, May 1994, pp. 5022-5026, vol. 91.

Ginot, F., "Oligonucleotide Micro-Arrays for Identification of Unknown Mutations: How Far from Reality?," *Human Mutation*, 1997, pp. 1-10, vol. 10.

Cheng, J. et al., "Microchip-based Devices for Molecular Diagnosis of Genetic Diseases," *Molecular Diagnosis*, 1996, vol. 1, No. 3.

Livache, T. et al., "Preparation of a DNA matrix via an electrochemically directed copolymerization of pyrrole and oligonucleotides bearing a pyrrole group," *Nucleic Acids Research*, 1994, pp. 2915-2921, vol. 22, No. 15.

Bustin, S.A., "Quantification of mRNA using real-time reverse transcription PCR (RT-PCR): trends and problems," *Journal of Molecular Endocrinology*, 2002; pp. 23-39, vol. 29.

Giulietti, A. et al, "An Overview of Real-Time Quantitative PCR: Applications to Quantify Cytokine Gene Expression," *Methods*, 2001, pp. 386-401, vol. 25.

Tachibana, T. et al., "Increased Intratumor Vα24-Positive Natural Killer T Cells: A Prognostic Factor for Primary Colorectal Carcinomas," *Clin Cancer Res.*, Oct. 15, 2005, pp. 7322-7327, vol. 11, No. 20.

Liu, J. et al., "Gene expression profiling for nitric oxide prodrug JS-K to kill HL-60 myeloid leukemia cells," *Genomics*, 2009, pp. 32-38, vol. 94.

Clemson, C.M. et al., "An Architectural Role for a Nuclear Noncoding RNA: NEAT1 RNA Is Essential for the Structure of Paraspeckles," *Molecular Cell*, Mar. 27, 2009, pp. 717-726, vol. 33.

Sheu, B. et al., "Up-regulation of Inhibitory Natural Killer Receptors CD94/NKG2A with Suppressed Intracellular Perforin Expression of Tumor-Infiltrating CD8[1] T Lymphocytes in Human Cervial Carcinoma," *Cancer Res.*, Apr. 1, 2005, pp. 2921-2929, vol. 65, No. 7.

McGilvray, R.W. et al., "NKG2D Ligand Expression in Human Colorectal Cancer Reveals Associations with Prognosis and Evidence for Immunoediting," *Clin Cancer Res*, Nov. 15, 2009, pp. 6993-7002, vol. 15, No. 22.

Keller, G.H. et al., "Section 5 Non-Radioactive Labeling Procedures," *DNA Probes*, 2nd Ed., 1993, pp. 173-198.

Keller, G.H. et al., "Section 6 Hybridization Formats and Detection Procedures," *DNA Probes*, 2nd Ed., 1993, pp. 199-253.

Tyagi et al., "Molecular Beacons: Probes that Fluoresce upon Hybridization," *Nature Biotechnology*, Mar. 1996, pp. 303-308, vol. 14.

Ramsay, G., "DNA chips: State-of-the art," *Nature Biotechnology*, Jan. 1998, pp. 40-44, vol. 16.

Cheng, J. et al., "Preparation and hybridization analysis of DNA/RNA from E.coli on microfabricated bioelectronic chips," *Nature Biotechnology*, Jun. 1998, pp. 541-546, vol. 16.

International Search Report issued in International Application No. PCT/EP2010/057843 on Apr. 1, 2011.

(56) References Cited

OTHER PUBLICATIONS

Written Opinion of the International Searching Authority issued in International Application No. PCT/EP2010/057843 on Apr. 1, 2011.
Maglott et al., "Entrez Gene: Gene-Centered Information at NCBI," Nucleic Acids Research, 2007, vol. 35, pp. D26-D31.
Genbank, Accession No. NM_001031700, 2000.
Genbank, Accession No. NM_016613, 2000.
Genbank, Accession No. NM_001128424, 2000.
Oct. 1, 2013 International Preliminary Report on Patentability issued in International Application No. PCT/CN2012/072931.
Jul. 5, 2012 International Search Report issued in International Application No. PCT/CN2012/072931.
U.S. Appl. No. 14/007,439, filed Oct. 18, 2013 in the name of Ye et al.
May 12, 2016 Office Action issued in U.S. Appl. No. 14/007,439.
Xu, Ye, et. al., "Decrease in Natural Killer Cell Associated Gene Expression as a Major Characteristic of the Immune Status in the Bloodstream of Colorectal Cancer Patients." Cancer Biology & Therapy, http://dx.doi.org/10.4161/cbt.11.2.13670. vol. 11, Issue 2, p. 188-195, 2011.

* cited by examiner

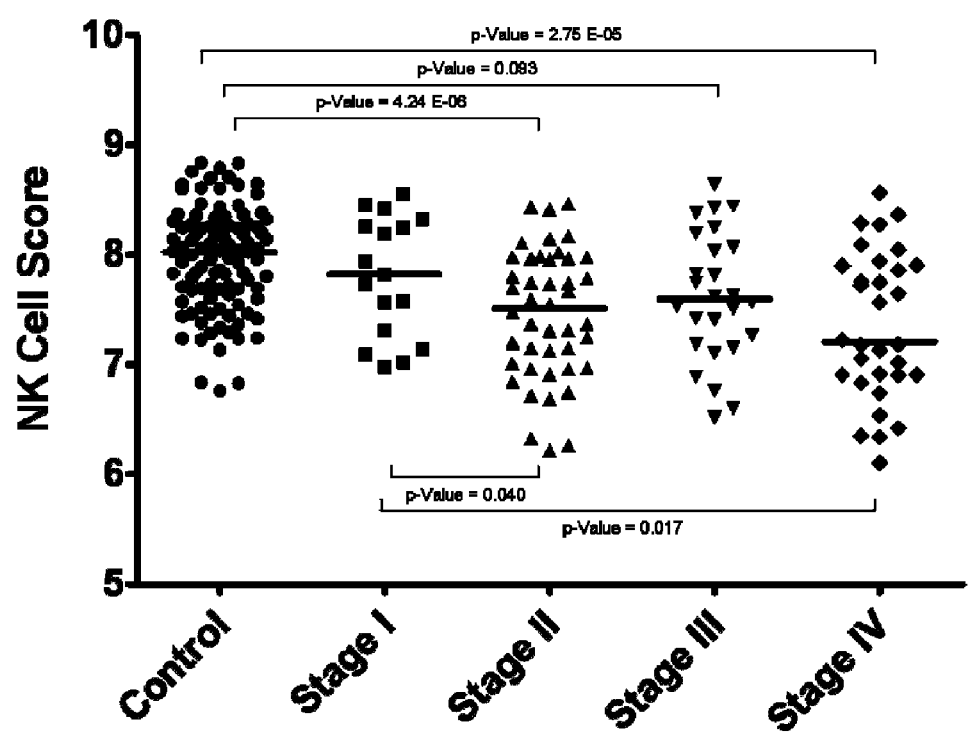

METHOD AND KIT FOR THE PROGNOSIS OF COLORECTAL CANCER

FIELD OF THE INVENTION

The present invention relates to the prognosis of a colorectal cancer, especially to a method and kit for prognosis such a cancer.

BACKGROUND

Colorectal cancer (CRC), also called colon cancer or large bowel cancer is the fifth most common form of cancer in the United States, the fourth common cancer in China and the third leading cause of cancer-related death in Europe. The early detection of CRC remains a major public health challenge. Indeed, CRC is often curable particularly when diagnosed at early stages. Several screening strategies are already in place in various countries. Conventional CRC screening tests include fecal occult blood test (FOBT), sigmoidoscopy, colonoscopy, double contrast barium enema, or digital rectal examination. All of them have advantages and limitations, but compliance remains less than expected mainly due to logistics or discomfort for the patients.

Search for blood biomarkers aimed at early detection of CRC became a focus since several years, especially for its convenience. Meantime, blood-based test feasibility was supported by very few studies, which have shown that gene biomarkers in blood could differentiate CRC patients from controls. These studies were based on the flow cytometry that is a technique for counting and examining microscopic particles, such as cells by suspending them in a stream of fluid and passing them by an electronic detection apparatus.

The present inventors have found that differentially expressed genes were mostly associated to immune cell activation and trafficking. Especially, they have shown that Natural Killer cells (NK cells) represent important biomarkers in peripheral blood samples. They did not used classical technique of flow cytometry but the determination of differential expression of genes from whole blood. It is non usual to determine an expression level of genes via the analysis of transcripts in whole blood, because it is commonly admitted by the persons skilled in the art that it is very difficult to retrieve a specific information when it is diluted in a complex mixture of RNAs (total RNA) without a step of specific purification. An advantage of the present method is also to avoid the step of purification of RNA.

Accordingly, the present invention relates to a method for determining the prognosis of a colorectal cancer in a peripheral blood sample from a patient, the method comprising:
a) obtaining the peripheral blood sample and extracting total RNA from the blood sample,
b) contacting the total RNA with at least one reagent that is specific for at least one NK cell gene and no more than 25 specific reagents for 25 NK cell genes,
c) determining the expression level of the at least one NK cell gene and of the most 25 NK cell genes to obtain an expression profile for the patient,
d) performing analysis of the expression profile of the patient with expression profiles of NK cell genes from patients previously clinically classified as a good prognosis and expression profiles of NK cell genes from patients previously classified as a poor prognosis, wherein if the expression profile for the patient is clustered with the expression profiles from patients previously clinically classified as a poor prognosis, then the patient is determined to have a poor prognosis, and
if the expression profile for the patient is clustered with the expression profiles from patients previously clinically classified as a good prognosis, then the patient is determined to have a good prognosis.

Especially in the above step b) the total RNA is brought into contact with at least one reagent is specific for at least one NK cell gene and no more than 25 specific reagents for 25 NK cell genes, said NK cell gene comprising the nucleic acid sequences set forth in SEQ ID NOs: 1 to 13, wherein the at least one reagent is specific for at least one NK cell gene selected from the group consisting of:
(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 gene comprising a full length sequence such as identified in SEQ ID NO: 13, and the expression level of the at least one NK cell gene is determined in step c) to obtain the expression profile for the patient.

The expression level of at least one of the above genes is a sufficient information for predicting a risk of CRC, as detailed in the experimental data.

In one embodiment in step b) the total RNA is brought into contact with reagents specific for a combination of least 5 NK cell genes and no more than 25 NK cell genes, wherein the reagents include at least reagents specific for the NK cell genes consisting of:
(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 comprising a full length sequence such as identified in SEQ ID NO: 13, the expression level of at least said 5 NK cell genes is determined in step c) to obtain the expression profile for the patient.

Furthermore, in step b) the total RNA can be brought into contact with at least one reagent specific for at least one target cell gene and no more than 5 specific reagents for 5 target cell genes, said target cell gene comprising the nucleic acid sequences set forth in SEQ ID NOs: 14 to 30, wherein the at least one reagent is specific for at least one target cell gene selected from the group consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30, and the expression level of the at least one cell gene is determined in step c) to obtain the expression profile for the patient; and in one embodiment the total RNA is brought into contact with reagents specific for a combination 5 target cell genes, wherein the reagents are specific for the target cell genes consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30, and the expression level of the at least 5 cell gene is determined in step c) to obtain the expression profile for the patient.

In another embodiment, in step b) the total RNA is further brought into contact with at least one reagent specific for at least one target cell gene and no more than 100 specific reagents for 100 target cell genes, said target cell gene comprising the nucleic acid sequences set forth in SEQ ID NOs: 25 to 59, wherein the at least one reagent is specific for at least one target cell gene selected from the group consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDE4D gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51,
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59, and, the expression level of the at least one cell gene is determined in step c) to obtain the expression profile for the patient.

Especially, in step b) the total RNA is brought into contact with reagents specific for a combination of least 17 target cell genes and no more than 100 target cell genes, wherein the reagents include at least reagents specific for the target cell genes consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDE4D gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51,
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59, and the expression level of the at least 17 cell genes is determined in step c) to obtain the expression profile for the patient.

More precisely, in the methods described above the at least one specific reagent of step b) comprises at least one hybridization probe, in particular at least one hybridization probe and at least one primer and more particularly at least one hybridization probe and two primers.

Total RNA comprises transfer RNAs (tRNA), messenger RNAs (mRNAs), such as the mRNAs transcribed from the target gene, but also transcribed from any other gene, and ribosomal RNAs.

By way of indication, the extraction of total RNA can be carried out by: a step consisting of lysis of the cells present in the blood sample, in order to release the nucleic acids contained in the cells of the patient. By way of example, use may be made of the methods of lysis as described in patent applications: WO 00/05338 regarding mixed magnetic and mechanical lysis, WO 99/53304 regarding electrical lysis, WO 99/15321 regarding mechanical lysis. Those skilled in the art may use other well-known methods of lysis, such as thermal or osmotic shocks or chemical lyses using chaotropic agents such as guanidinium salts (U.S. Pat. No. 5,234,809). It is also possible to provide an additional step for separating the nucleic acids from the other cellular constituents released in the lysis step. This generally makes it possible to concentrate the nucleic acids. By way of example, use may be made of magnetic particles optionally coated with oligonucleotides, by adsorption or covalence (in this respect, see U.S. Pat. Nos. 4,672,040 and 5,750,338), and the nucleic acids which are bound to these magnetic particles can thus be purified by means of a washing step. This nucleic acid purification step is particularly advantageous if it is desired to subsequently amplify said nucleic acids. A particularly advantageous embodiment of these magnetic particles is described in patent applications: WO-A-97/45202 and WO-A-99/35500.

The term "specific reagent" is intended to mean a reagent which, when it is brought into contact with biological material as defined above, binds with the material specific for said target gene. By way of indication, when the specific reagent and the biological material are of nucleic origin, bringing the specific reagent into contact with the biological material allows the specific reagent to hybridize with the material specific for the target gene. The term "hybridization" is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracile (U)) bases (this is referred to as an A-T bond) or between the complementary guanine (G) and cytosine (C) bases (this is referred to as a G—C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base. The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70.degree. C., in particular between 35 and 65.degree. C. in a saline solution at a concentration of approximately 0.5 to 1 M. A sequence, or nucleotide fragment, or oligonucleotide, or polynucleotide, is a series of nucleotide motifs assembled together by phosphoric ester bonds, characterized by the informational sequence of the natural nucleic acids, capable of hybridizing to a nucleotide fragment, it being possible for the series to contain monomers having different structures and to be obtained from a natural nucleic acid molecule and/or by genetic recombination and/or by chemical synthesis. A motif is a derivative of a monomer which may be a natural nucleotide of nucleic acid, the constitutive elements of which are a sugar, a phosphate group and a nitrogenous base; in DNA, the sugar is deoxy-2-ribose, in RNA, the sugar is ribose; depending on whether DNA or RNA is involved, the nitrogenous base is selected from adenine, guanine, uracile, cytosine and thymine; alternatively the monomer is a nucleotide that is modified in at least one of the three constitutive elements; by way of example, the modification may occur either at the level of the bases, with modified bases such as inosine, methyl-5-deoxycytidine, deoxyuridine, dimethylamino-5-deoxyuridine, diamino-2,6-purine, bromo-5-deoxyuridine or any other modified base capable of hybridization, or at the level of the sugar, for example the replacement of at least one deoxyribose with a polyamide (P. E. Nielsen et al, Science, 254, 1497-1500 (1991)[3]), or else at the level of the phosphate group, for example its replacement with esters in particular selected from diphosphates, alkyl- and arylphosphonates and phosphorothioates.

According to a specific embodiment of the invention, the specific reagent comprises at least one hybridization probe or at least one hybridization probe and at least one primer which is specific for the target gene or at least one hybridization probe and two primers specific for the target genes.

For the purpose of the present invention, the term "amplification primer" is intended to mean a nucleotide fragment comprising from 5 to 100 nucleotides, preferably from 15 to 30 nucleotides that allow the initiation of an enzymatic polymerization, for instance an enzymatic amplification reaction. The term "enzymatic amplification reaction" is intended to mean a process which generates multiple copies of a nucleotide fragment through the action of at least one enzyme. Such amplification reactions are well known to those skilled in the art and mention may in particular be made of the following techniques: PCR (polymerase chain reaction), as described in U.S. Pat. Nos. 4,683,195, 4,683,202 and 4,800,159, LCR (ligase chain reaction), disclosed, for, example, in patent application EP 0 201 184, RCR (repair chain reaction), described in patent application WO 90/01069, 3SR (self sustained sequence replication) with patent application WO 90/06995, NASBA (nucleic acid sequence-based amplification) with patent application WO 91/02818, TMA (transcription mediated amplification) with U.S. Pat. No. 5,399,491 and RT-PCR.

When the enzymatic amplification is a PCR, the specific reagent comprises at least two amplification primers, specific for a target gene, that allow the amplification of the material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the cDNAs specific for a target gene (reference is then made to target-gene-specific cRNA). When the enzymatic amplification is a PCR carried out after a reverse transcription reaction, reference is made to RT-PCR.

The term "hybridization probe" is intended to mean a nucleotide fragment comprising at least 5 nucleotides, such as from 5 to 100 nucleotides, in particular from 10 to 75 nucleotides, such as 15-35 nucleotides and 60-70 nucleotides, having a hybridization specificity under given conditions so as to form a hybridization complex with the material specific for a target gene. In the present invention, the material specific for the target gene may be a nucleotide sequence included in a messenger RNA derived from the target gene (reference is then made to target-gene-specific mRNA), a nucleotide sequence included in a complementary DNA obtained by reverse transcription of said messenger RNA (reference is then made to target-gene-specific cDNA), or else a nucleotide sequence included in a complementary RNA obtained by transcription of said cDNA as described above (reference will then be made to target-gene-specific cRNA). The hybridization probe may include a label for its detection. The term "detection" is intended to mean either a direct detection such as a counting method, or an indirect detection by a method of detection using a label. Many methods of detection exist for detecting nucleic acids (see, for example, Kricka et al., Clinical Chemistry, 1999, no 45 (4), p. 453-458 or Keller G. H. et al., DNA Probes, 2nd Ed., Stockton Press, 1993, sections 5 and 6, p. 173-249. The term "label" is intended to mean a tracer capable of generating a signal that can be detected. A non limiting list of these tracers includes enzymes which produce a signal that can be detected, for example, by colorimetry, fluorescence or luminescence, such as horseradish peroxidase, alkaline phosphatase, beta-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as $^{32}P$, $^{35}S$ or $^{125}I$.

For the purpose of the present invention, the hybridization probe may be a "detection" probe. In this case, the "detection" probe is labeled by means of a label. The detection probe may in particular be a "molecular beacon" detection probe as described by Tyagi & Kramer (Nature biotech, 1996, 14:303-308). These "molecular beacons" become fluorescent during the hybridization. They have a stem-loop-type structure and contain a fluorophore and a "quencher" group. The binding of the specific loop sequence with its complementary target nucleic acid sequence causes the stem to unroll and the emission of a fluorescent signal during excitation at the appropriate wavelength. The detection probe in particular may be a "reporter probe" comprising a "color-coded barecode" according to NanoString™'s technology.

For the detection of the hybridization reaction, use may be made of target sequences that have been labeled, directly (in particular by the incorporation of a label within the target sequence) or indirectly (in particular using a detection probe as defined above). It is in particular possible to carry out, before the hybridization step, a step consisting in labeling and/or cleaving the target sequence, for example using a labeled deoxy-ribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2780059.

According to a preferred embodiment of the invention, the detection probe comprises a fluorophore and a quencher. According to an even more preferred embodiment of the invention, the hybridization probe comprises an FAM (6-carboxy-fluorescein) or ROX (6-carboxy-X-rhodamine) fluorophore at its 5' end and a quencher (Dabsyl) at its 3' end.

The hybridization probe may also be a "capture" probe. In this case, the "capture" probe is immobilized or can be immobilized on a solid substrate by any appropriate means, i.e. directly or indirectly, for example by covalence or adsorption. As solid substrate, use may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cDNAs or cRNAs specific for a target gene that it is desired to analyze are then hybridized, for example, to specific capture probes. After hybridization, the substrate or chip is washed and the labeled cDNA or cRNA/capture probe complexes are revealed by means of a high-affinity ligand bound, for example, to a fluorochrome-type label. The fluorescence is read, for example, with a scanner and the analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614. "Light-generated oligonucleotide arrays for rapid DNA sequence analysis", A. Caviani Pease et al., Proc. Natl. Acad. Sci. USA, 1994, 91, 5022-5026), for molecular diagnoses. In this technology, the capture probes are generally small in size, around 25 nucleotides. Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1 (3), p. 183-200; T. Livache et al, Nucleic Acids Research, 1994, No. 22 (15), p. 2915-2921 J. Cheng et al, Nature Biotechnology, 1998, No. 16, p. 541-546 or in U.S. Pat. Nos. 4,981,783, 5,700,637, 5,445,934, 5,744,305 and 5,807,522. The main characteristic of the solid substrate should be to conserve the hybridization characteristics of the capture probes on the target nucleotide fragments while at the same time generating a minimum background noise for the method of detection. Three main types of fabrication can be distinguished for immobilizing the probes on the substrate.

First of all, there is a first technique which consists in depositing pre-synthesized probes. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition).

Printing is an adaptation of the method used by inkjet printers. It is based on the propulsion of very small spheres of fluid (volume<1 nl) at a rate that may reach 4000 drops/second. The printing does not involve any contact between the system releasing the fluid and the surface on which it is deposited.

Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 cm.sup.2. The use of nylon membranes, referred to as "macroarrays", which carry products that have been amplified, generally by PCR, with a diameter of 0.5 to 1 mm and the maximum density of which is 25 spots/cm.sup.2, should not however be forgotten. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It consists in moving a reaction chamber, in which the oligonucleotide extension reaction takes place, along the glass surface.

Finally, the third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers ($\mu m^2$). This resolution makes it possible to create up to several hundred thousand spots on a surface area of a few square centimeters ($cm^2$). Photolithography has advantages: in bulk in parallel, it makes it possible to create a chip of N-mers in only 4.times.N cycles. All these techniques can be used with the present invention. According to a preferred embodiment of the invention, the at least one specific reagent of step b) defined above comprises at least one hybridization probe which is preferably immobilized on a substrate. This substrate is preferably a low-, high- or medium-density substrate as defined above.

These hybridization steps on a substrate comprising a multitude of probes may be preceded by an enzymatic amplification reaction step, as defined above, in order to increase the amount of target genetic material.

In step c), the determination of the expression level of a target gene can be carried out by any of the protocols known to those skilled in the art. In general, the expression of a target gene can be analyzed by detecting the mRNAs (messenger RNAs) that are transcribed from the target gene at a given moment.

The invention preferably relates to the determination of the expression level of a target gene by detection of the mRNAs derived from this target gene according to any of the protocols well known to those skilled in the art. According to a specific embodiment of the invention, the expression level of several target genes is determined simultaneously, by detection of several different mRNAs, each mRNA being derived from a target gene.

When the specific reagent comprises at least one amplification primer, it is possible, to determine the expression level of the target gene in the following way: 1) After having extracted the total RNA (comprising the transfer RNAs (tRNAs), the ribosomal RNAs (rRNAs) and the messenger RNAs (mRNAs)) from the whole blood, a reverse transcription step is carried out in order to obtain the complementary DNAs (or cDNAs) of said mRNAs. By way of indication, this reverse transcription reaction can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can in particular be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained. 2) The amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for different target genes, by using several pairs of different amplification primers, each one being specific for a target gene: reference is then made to multiplex amplification. 3) The expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio of the expression of the target gene to the expression of the housekeeping gene, i.e. by realizing a ratio of the amount of target-gene-specific cDNAs to the amount of housekeeping-gene-specific cDNAs, any variability between the various experiments is thus corrected. Those skilled in the art may refer in particular to the following publications: Bustin S A, J Mol Endocrinol, 2002, 29: 23-39; Giulietti A Methods, 2001, 25: 386-401.

When the specific reagent comprises at least one hybridization probe, the expression of a target gene can be determined in the following way: 1) After having extracted the total RNA from the whole blood, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene). 2) All the cDNAs are brought into contact with a substrate, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid substrate which includes all the materials as indicated above. According to a preferred embodiment, the hybridization probe is immobilized on a substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred specific methods for labeling and/or cleaving nucleic acids are described in applications WO 99/65926, WO 01/44507, WO 01/44506, WO 02/090584, WO 02/090319. 3) A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

When the at least one specific reagent is brought into contact in step b) comprises at least one hybridization probe, the expression of a target gene can also be determined in the following way: 1) After having extracted the total RNA from the whole blood, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained. 2) All the cRNAs are brought into contact with a substrate on which are immobilized capture probes specific for the target gene whose expression it is desired to analyze, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step consisting in labeling and/or cleaving the target-gene-specific cRNAs as described above. 3) A step consisting of detection of the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

The present invention also includes a kit for the prognosis of a colorectal cancer in a peripheral blood sample from a patient comprising at least one specific reagent for at least one NK cell gene and no more than 25 specific reagents for 25 NK cell genes comprising at least the nucleic acid sequences set forth in SEQ NOs 1 to 13, wherein the at least one reagent is specific for at least one NK cell gene selected from the group consisting of:

(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 gene comprising a full length sequence such as identified in SEQ ID NO: 13.

In one embodiment, the kit comprises a combination of reagents that are specific for the NK cell genes consisting of:
(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 gene comprising a full length sequence such as identified in SEQ ID NO: 13.

In such an embodiment, the specific reagents can targeted a combination of several NK cell genes but no more than 25 NK genes.

Furthermore, the kit can comprise at least one reagent that is specific for at least one target cell gene and no more than 5 target cell genes, said at least one target cell gene being selected from the group consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30.

In particular, it comprises 5 reagents that are specific for the target cell genes consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30.

In such an embodiment, the specific reagents can targeted a combination of several target cell genes, such as described above but no more than 5 target cell genes.

In another embodiment, the kit such as defined above can comprise at least one reagent that is specific for at least one target cell gene and at the most 100 reagents that are specific for 100 target cell genes, said at least target cell gene being selected from the group consisting of:
(i) MRPS6 gene comprising a full length sequence such as identified in SEQ ID NO: 31 , 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDE4D gene comprising a full length sequence such as identified in SEQ ID NO: 38 or 39,
(vii) SH2D2A gene comprising a full length sequence such as identified in SEQ ID NO: 40 , 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50 , or 51,
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59.

And especially, it comprises 17 reagents that are specific for 17 target cell genes consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,.
(vi) DPDE4D gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51.
(xii) P2RY 10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59.

In such an embodiment, the specific reagents can targeted a combination of several target cell genes, such as described above but no more than 100 target cell genes.

As explained above the at least one specific reagent comprises at least one hybridization probe, in particular at least one hybridization probe and at least one primer and more particularly at least one hybridization probe and two primers.

Finally, the invention concerns the use of at least one specific reagent for at least one NK cell genes and no more than 25 specific reagents for 25 NK cell genes comprising the nucleic acid sequences set forth in SEQ ID NOs: 1 to 13 in the manufacture of a composition for the prognosis of colorectal cancer in a biological sample from a patient, wherein the at least one reagent is specific for at least one NK cell gene comprising a nucleic acid sequence selected from the nucleic acid sequences set forth in anyone of SEQ ID NOs: 1 to 13;

especially the use of reagents specific for a combination of at least 5 NK cell genes and no more than 25 NK cell genes in the manufacture of a composition for the prognosis of colorectal cancer in a biological sample from a patient, wherein the reagents are specific for at least 5 NK cell genes comprising a nucleic acid sequence selected from the nucleic acid sequences set forth in SEQ ID NOs: 1, 2 to 4, 5 to 7, 8 to 12, and 13 respectively;

in particular, the use of reagents specific for a combination of 10 target cell genes in the manufacture of a composition for the prognosis of colorectal cancer in a biological sample from a patient, wherein the reagents are specific for target cell genes comprising a nucleic acid sequence selected from the nucleic acid sequences set forth in SEQ ID NOs: 1, 2to 4, 5 to 7, 8 to 12, 13, 14 to 17, 18 to 20, 21-22 , 23-24, and 25 to 30, respectively; and more particularly the use of reagents specific for a combination of 10 target cell genes and no more than 100 target genes in the manufacture of a composition for the prognosis of colorectal cancer in a biological sample from a patient, wherein the reagents are specific for target cell genes comprising a nucleic acid sequence selected from the nucleic acid sequences set forth in SEQ ID NOs: 1, 2 to 4, 5 to 7, 8 to 12, 13, 14 to 17, 18 to 20, 21-22, 23-24, 25 to 30, 31 to 33, 34, 35, 36, 37, 38-39, 40 to 42, 43-44, 45, 46-49, 50-51, 52-53, 54, 55-56, 57, 58 and 59 respectively;

wherein the at least one specific reagent comprises at least one hybridization probe, at least one hybridization probe and at least one primer or at least one hybridization probe and two primers.

FIGURE

NK Cell Score in colonoscopy negative control (CNC) and colorectal cancer (CRC) patient blood samples, with distribution for CRC samples according to the cancer stage. Circles represent CNC; squares, up triangles, down triangle and lozenges represent CRC, Stage I, II, III and IV, respectively.

EXAMPLES

I) Materials and Methods
1. Patients and Sample Collection

The study was approved by the local Ethical Committee for Clinical Research. Written informed consent was obtained for all participants.

For the CRC group, 119 colorectal patients were consecutively recruited for the study, between July 2006 and March 2008 at the Department of Colorectal Surgery, Fudan University Cancer Hospital (FUCH), China. The tumors were staged according to the International Union Against Cancer (UICC) recommended tumor-node-metastasis (TNM) system. No patient received preoperative radiotherapy or chemotherapy. Patients suffering from hereditary colorectal cancer or inflammatory bowel disease (Crohn's disease or ulcerative colitis) were excluded from this study. For each patient, 2.5 ml of peripheral blood were collected into PAXgene™ Blood RNA tubes (PreAnalytiX GmbH, Hombrechtikon, CH) at least one week after colonoscopy, before surgery, and processed according to manufacturer's guidelines. For the control group, 101 FOBT test-positive participants without carrying any symptom of polyps or colorectal cancer, which had been confirmed by colonoscopy, were enrolled from the Community Hospital in Shanghai area. The peripheral blood samples were collected into PAXgene tubes one week before colonoscopy examination. A detailed characterization of all participants included in this study is given in Table 1.

TABLE 1

Characteristics of the Patients

| Category | Colorectal cancer (CRC) n = 119 | Colonoscopy negative controls (CNC) n = 101 |
|---|---|---|
| Age (y) | | |
| Average | 57.6 | 54.9 |
| Max | 82 | 71 |
| Min | 27 | 38 |
| Gender | | |
| Male | 59 | 42 |
| Female | 60 | 59 |
| Site | | |
| Colon | 60 | — |
| Rectal | 59 | |
| Cancer UICC Stage | | |
| Stage I | 17 | — |
| Stage II | 44 | |
| Stage III | 26 | |
| Stage IV | 32 | |

2. RNA Extraction and Microarray Experiments

Total RNA was extracted with the PAXgene™ Blood RNA System (PreAnalytix) following manufacturer's instructions. The quantity of total RNA was measured by spectrophotometer at optical density 260 nanometers and the quality was assessed using the RNA 6000 Nano LabChip® Kit on a BioAnalyzer Agilent 2100 (Agilent Technologies, Palo Alto, Calif., U.S.A.). Only samples with RNA Integrity Number between 7 and 10 were analyzed. 50 nanograms of total RNA was then reversely transcribed and linearly amplified to single strand cDNA using Ribo-SPIA™ technology with WT-Ovation™ RNA Amplification System (NuGEN Technologies Inc., San Carlos, Calif., U.S.A.) according to the manufacturer's standard protocol, and the products were purified with QIAquick™ PCR purification kit (QIAGEN GmbH, Hilden, Germany). 2 micro grams of amplified and purified cDNA were subsequently fragmented with RQ1 RNase-Free DNase (Promega Corp., Fitchburg, Wis., U.S.A.) and labeled with biotinylated deoxynucleoside triphosphates by Terminal Transferase (Roche Diagnostics Corp., Indianapoli, Ind., U.S.A.) and GeneChip® DNA Labeling Reagent (Affymetrix Inc., Santa Clara, Calif., U.S.A). The labeled cDNA was hybridized onto HG U133 Plus 2.0 Array (Affymetrix) in a Hybridization Oven 640 (Agilent Technologies) at 60 rotations per minute, 50° C. for 18 hours. The HG U133 Plus 2.0 Array contains 54,675 probe sets representing approximately 39,000 best-characterized human genes. After hybridization, the arrays were washed and stained according to the Affymetrix protocol EukGE-WS2v4 using a GeneChip® Fluidics Station 450 (Affymetrix). The arrays were scanned with the GeneChip® Scanner 3000 (Affymetrix).

3. Microarray Data Analysis

Quality control analyses were done according to the suggestions of standard Affymetrix quality control parameters. Based on the evaluation criteria, all our experiments fulfilled the minimal quality requirements. The Affymetrix expression arrays were preprocessed by RMA (Robust Multi-chip Average) with background correction, quantile normalization and median polish summarization [1]. The probe sets with extreme signal intensity (lower than 50 or higher than $2\cdot 10^{14}$) were filtered out. To reduce the likelihood of batch effect, a normalization algorithm, Combat was applied to the filtered expression data[11]. The ComBat method (http://statistics.byu.edu/johnson/ComBat/) applies either parametric or nonparametric empirical Bayes framework for adjusting batch effects in a given data set. Differential expressed genes (DEG) were identified by Significance Analysis of Microarrays (SAM) at False Discovery Rate (FDR) equals 0.05[12]. The preprocessing and statistical steps were executed using R-environment with Bioconductor libraries[13, 14]. Gene Ontology and Canonical Pathways analysis were conducted by using Ingenuity Pathway Analysis software version 8.5 (Ingenuity Systems, Redwood City, Calif., U.S.A).

II) Results

1. Characteristics of the Colorectal Cancer and Control Patient Populations

Clinical and demographic variables for the 119 colorectal cancer (CRC) patients and the 101 colonoscopy-negative controls (CNC) are summarized in Table 1. For the CRC, the diagnosis of colorectal cancer has been confirmed by the pathologist following the colonscopy. The controls have been selected among FOBT positive patients enrolled in the Community Hospital, for whom the colonoscopy performed at Fudan University Cancer Hospital (FUCH) was finally negative. The age and the gender were well balanced between the CRC and the CNC groups.

2. Identification of Genes Whose Expression in Peripheral Blood is Different for Colorectal Cancer Patients and Colonoscopy-Negative Controls The inventors looked for differentially expressed genes (DEG) between the 119 CRC and the 101 CNC, with the highest differences between the two groups, considering the CRC group as a whole (Stage I, II, III and IV). After appropriate preprocessing, 20,169 probe sets were retained to perform DEG analysis. Using SAM, 327 DEGs were identified at FDR equal to 0.05, with fold change (FC) higher than 1.2.

Among these 327 DEG, 195 (59.6%) and 132 (40.36%) were found to be expressed at higher and lower levels in CRC samples respectively. The t-test p-values ranged from $1.43\cdot 10^{-25}$ to $1.51\cdot 10^{-01}$, with 18 DEG having t-test p-values lower than $6.27\cdot 10^{-15}$ and all corresponding to well-annotated genes: MRPS6, SPRY4, NEAT1, CYBB, DUSP2, PDE4D, SH2D2A, G(1-2)NSR, ITGAM, VCAN, CD163, P2RY10, CD226, MRPL10, ITPRIPL2, CD2 and NUDT16 (Table 2). The highest fold change (FC) values were 1.83 (NEAT1 with higher level for CRC) and 1.71 (HBG2 with lower level for CRC), while 26 (8%) out of the 327 DEG have a FC value higher than 1.40.

As illustration, the results observed for SPRY4 (first ranked with higher expression level in CRC, t-test p-value $4.04\cdot 10^{-23}$, FC 1.79) and MRPS6 (first ranked with lower expression level in CRC, t-test p-value $1.43\cdot 10^{-25}$, FC 1.27). Such examples illustrate genes significantly differentially expressed between CRC and CNC patients. For SPRY4, rather homogenous hybridization signal values were observed for the 101 CNC, while the values for the CRC were more heterogeneous but with a mean value significantly (p-value $4.04\cdot 10^{-23}$) increased compared to CNC (FC 1.78). For MRPS6, both populations presented a similar dispersion, with a significant (p-value $1.43\cdot 10^{-25}$) mean decrease for CRC (FC 1.27).

Among the Top 18 DEG, four membrane leukocyte markers were observed, indicating different levels of expression in the peripheral blood of CRC patients compared to CNC: lower levels for CD2 and CD226 expressed by T cells and mainly NK cells respectively; higher levels for CD163 and CD11B (ITGAM) expressed mainly expressed by monocytes and in many leukocytes involved in the innate immune system, respectively. Also interesting is the lower expression of granzyme B encoded by the GZMB gene in cytotoxic T lymphocytes and Natural Killer (NK) cells, in CRC samples. The other genes like INSR, SPRY4, DUSP2, PDE4D, and ITPRIPL2 are reported to be part of various signaling pathways, SH2D2A reported to be T-cell specific. VCAN has been reported to be expressed in monocytes, and its higher expression levels in CRC samples, together with CD163 and ITGAM, would be associated with some activation of circulating monocytes in the peripheral blood of these patients compared to CNC.

Analysis of the 327 DEG has been performed by using Ingenuity Pathway Analysis (IPA), which returned 321 mapped IDs suitable for interpretation of associated Bio Functions and Canonical Pathways. For Physiological System Development and Function, a high score was observed for Immune Cell Trafficking (p-value from $1.44\cdot 10^{-12}$ to $1.57\cdot 10^{-02}$, with 50 molecules), covering activation, migration, accumulation, influx, chemotaxis, cell spreading, cell movement, chemoattraction, priming and adhesion of various immune cells. Interestingly for Canonical Pathways, Natural Killer Cell Signaling was the one with the lowest p-value ($2.55\cdot 10^{-05}$), with 10 genes: CD247, KLRB1, KLRC2, KLRC3, KLRD1, KLRK1, LCK, PRKCH, RRAS2 and SH2D1D. The implication of five membrane receptors specific to NK cells (KLRB1, KLRC2, KLRC3, KLRD1, KLRK1), very strongly suggests a particular NK cells component in the differences at the gene expression level in the peripheral blood of CRC patients. All NK cell genes are down-expressed in CRC. The results are summarized in the following tables 2 and 3.

TABLE 2

TOP 18 differentially expressed genes (DEGs) between colorectal cancer (CRC) and colonoscopy negative control (CNC) patient samples; Gene description, T-test p-value and fold change-related information

| Affymetrix Probeset ID | SEQ ID NOs: | Gene Name | Gene Description* | T-test p-value | Fold Change | Direction (in CRC) |
| --- | --- | --- | --- | --- | --- | --- |
| 224919_at | 31, 32, 33 | MRPS6 | Mitochondrial ribosomal protein S6 | $1.43\cdot 10^{-25}$ | 1.27 | Down |
| 220983_s_at | 34 | SPRY4 | Sprouty homolog 4 | $4.04\cdot 10^{-23}$ | 1.79 | Up |
| 227062_at | 35 | NEAT1 | Nuclear paraspeckle assembly transcript 1 | $7.62\cdot 10^{-22}$ | 1.83 | Up |

TABLE 2-continued

TOP 18 differentially expressed genes (DEGs) between colorectal cancer (CRC) and colonoscopy negative control (CNC) patient samples; Gene description, T-test p-value and fold change-related information

| Affymetrix Probeset ID | SEQ ID NOs: | Gene Name | Gene Description* | T-test p-value | Fold Change | Direction (in CRC) |
|---|---|---|---|---|---|---|
| 203922_s_at | 36 | CYBB | Cytochrome b-245, beta polypeptide | $4.36\ 10^{-21}$ | 1.31 | Up |
| 204794_at | 37 | DUSP2 | Dual specificity phosphatase 2 | $1.44\ 10^{-20}$ | 1.49 | Down |
| 204491_at | 38, 39 | PDE4D | Phosphodiesterase 4D, cAMP-specific | $7.83\ 10^{-20}$ | 1.49 | Down |
| 207351_s_at | 40, 41, 42 | SH2D2A | SH2 domain protein 2A | $1.28\ 10^{-19}$ | 1.47 | Down |
| 210164_at | 14, 15, 16, 17 | GZMB | Granzyme B | $3.75\ 10^{-18}$ | 1.62 | Down |
| 213792_s_at | 43, 44 | INSR | Insulin receptor | $4.24\ 10^{-18}$ | 1.35 | Up |
| 205785_at | 45 | ITGAM | Integrin alpha M | $5.43\ 10^{-18}$ | 1.32 | Up |
| 215646_s_at | 46, 47, 48, 49 | VCAN | Versican | $6.03\ 10^{-18}$ | 1.49 | Up |
| 203645_s_at | 50, 51 | CD163 | CD163 | $3.78\ 10^{-17}$ | 1.44 | Up |
| 1553856_s_at | 52, 53 | P2RY10 | Purinergic receptor P2Y, G-protein coupled, 10 | $4.19\ 10^{-17}$ | 1.26 | Down |
| 207315_at | 54 | CD226 | CD226 | $1.14\ 10^{-16}$ | 1.29 | Down |
| 224671_at | 55, 56 | MRPL10 | Mitochondrial ribosomal protein L10 | $1.68\ 10^{-16}$ | 1.21 | Down |
| 227954_at | 57 | ITPRIPL2 | Inositol 1,4,5-triphosphate receptor interacting protein-like 2 | $8.71\ 10^{-16}$ | 1.26 | Up |
| 205831_at | 58 | CD2 | CD2 | $5.96\ 10^{-15}$ | 1.28 | Down |
| 235002_at | 59 | NUDT16 | Nudix (nucleoside diphosphate linked moiety X)-type motif 16 | $6.27\ 10^{-15}$ | 1.21 | Up |

*Gene description from NetAffx ™ and from Ingenuity Pathway Analysis ® version 8.5

TABLE 3

NK cell score: Selected genes, T-test p-value and fold change-related information

| Affymetrix Probeset ID | SEQ ID Nos: | Gene Name | Gene Description* | T-test p-value | Fold change CNC/CRC |
|---|---|---|---|---|---|
| 214470_at | 1 | KLRB1 | Killer cell lectin-like receptor subfamily B, member 1 | $2.67\ 10^{-04}$ | 1.23 |
| 206785_s_at | 2, 3, 4 | KLRC2 | Killer cell lectin-like receptor subfamily C, member 2 | $3.02\ 10^{-05}$ | 1.40 |
| 207723_s_at | 5, 6, 7 | KLRC3 (NKG2E) | Killer cell lectin-like receptor subfamily C, member 3 | $4.42\ 10^{-05}$ | 1.36 |
| 210606_x_at | 8, 9, 10, 11, 12 | KLRD1 | Killer cell lectin-like receptor subfamily D, member 1 | $1.57\ 10^{-05}$ | 1.23 |
| 205821_at | 13 | KLRK1 (NKG2D) | Killer cell lectin-like receptor subfamily K, member 1 | $5.22\ 10^{-06}$ | 1.22 |
| 210164_at | 14, 15, 16, 17 | GZMB | Granzyme B | $3.75\ 10^{-18}$ | 1.62 |
| 210031_at | 18, 19, 20 | CD247 (CD3-zeta) | CD247 molecule | $2.82\ 10^{-10}$ | 1.27 |
| 212589_at | 21, 22 | RRAS2 | Related RAS viral(r-ras) oncogene homolog 2 | $7.17\ 10^{-04}$ | 1.20 |

TABLE 3-continued

NK cell score: Selected genes, T-test p-value and fold change-related information

| Affymetrix Probeset ID | SEQ ID Nos: | Gene Name | Gene Description* | T-test p-value | Fold change CNC/CRC |
|---|---|---|---|---|---|
| 1553176_at | 23, 24 | SH2D1B | SH2 domain containing 1B | $2.11\ 10^{-10}$ | 1.47 |
| 204891_s_at | 25, 26, 27, 28, 29, 30 | LCK | Lymphocyte-specific protein tyrosine kinase | $1.93\ 10^{-11}$ | 1.22 |

*Gene description from NetAffx ™ and from Ingenuity Pathway Analysis ® version 8.5

For these 10 NK cell-related genes, lower expression levels have been observed in the CRC group, suggesting either a decrease in the number of circulating NK cells, or an efflux of such cells towards other organ/tissue compartments and particularly the tumor sites. The lower expression levels observed for GZMB is also remarkable, evocative of a major event occurring at the level of cellular cytotoxicity in CRC patients.

The top canonical pathways were related to T Cell Receptor Signaling, Communication between Innate and Adaptive Immune Cells, and iCOS-iCOSL Signaling in T Helper Cells, with p-values equal to $9.08\ 10^{-05}$, $2.85\ 10^{-04}$ and $5.78\ 10^{-04}$ respectively.

Interestingly, a low NK Cell Score under the first quarter, was observed for 51 out of the 119 CRC patients samples, and in only 4 out of the 101 CNC patients samples. Using such a straightforward cut-off, the performance of this discrimination can be expressed as 43% sensitivity and 96% specificity. Furthermore, when stratifying the CRC patients samples according to their tumor TNM staging (Stage I, II, III or IV), we observed that this NK Cell Score gradually decreased in CRC patients from Stage I to Stage IV (FIG. 1). Statistically significant differences were mainly observed between CNC and CRC Stage II, III and IV, and between CRC Stage I and CRC Stage II-III and IV.

This study shows the potential of transcriptomics in peripheral blood, to discover biomarkers, and provide new insight on immune response in colorectal cancer. In addition to prepare possible alternative/complement to current screening modalities, these results also show that the expression analysis of genes like those related to NK cells should allow to stratify patients with colorectal cancer, opening the door to personalized medicine.

REFERENCES

1. Irizarry R A, Hobbs B, Collin F, Beazer-Barclay Y D, Antonellis K J, Scherf U, Speed T P. Exploration, normalization, and summaries of high density oligonucleotide array probe level data. Biostatistics 2003; 4:249-64)
2. Johnson W E, Li C, Rabinovic A. Adjusting batch effects in microarray expression data using empirical Bayes methods. Biostatistics 2007; 8:118-27.
3. Tusher V G, Tibshirani R, Chu G. Significance analysis of microarrays applied to the ionizing radiation response. Proc Natl Acad Sci USA 2001; 98:5116-21.
4. Team RDC. R: A Language and Environment for Statistical Computing. Vienna, Austria, 2009.

The invention claimed is:

1. A method comprising:
extracting total RNA from a peripheral blood sample obtained from a patient suspected of having or having colorectal cancer;
contacting the total RNA, or cDNA or cRNA obtained from the total RNA, with one or more reagents specific for at least one target gene and no more than 100 target genes; and
measuring the expression level of the at least one target gene and no more than 100 target genes,
wherein the at least one target gene and no more than 100 target genes includes the NEAT1 gene.

2. The method as claimed in claim 1, wherein the one or more reagents comprise at least one hybridization probe.

3. The method as claimed in claim 1, wherein the one or more reagents comprise at least one hybridization probe and at least one primer.

4. The method as claimed in claim 1, wherein the one or more reagents comprise at least one hybridization probe and at least one pair of primers.

5. The method as claimed in claim 1, wherein:
the one or more reagents further include at least one reagent selected from the group consisting of reagents specific for the DUSP2, PDE4D, SH2D2A, GZMB, ITGAM, P2RY10, ITPRIPL2, and NUDT16 genes; and
the expression level of at least one of the DUSP2, PDE4D, SH2D2A, GZMB, ITGAM, P2RY10, ITPRIPL2, or NUDT16 genes is measured.

6. The method as claimed in claim 1, wherein:
the one or more reagents further include at least one reagent selected from the group consisting of reagents specific for the MRPS6, SPRY4, CYBB, DUSP2, PDE4D, SH2D2A, GZMB, INSR, ITGAM, VCAN, CD163, P2RY10, CD226, MRPL10, ITPRIPL2, CD2, and NUDT16 genes; and
the expression level of at least one of the MRPS6, SPRY4, CYBB, DUSP2, PDE4D, SH2D2A, GZMB, INSR, ITGAM, VCAN, CD163, P2RY10, CD226, MRPL10, ITPRIPL2, CD2, or NUDT16 genes is measured.

7. The method as claimed in claim 1, wherein:
the one or more reagents further include at least one reagent selected from the group consisting of reagents specific for the KLRB1, KLRC2, KLRC3, KLRD1, and KLRK1 genes; and
the expression level of at least one of the KLRB1, KLRC2, KLRC3, KLRD1, or KLRK1 genes is measured.

8. The method as claimed in claim 1, wherein:
the one or more reagents further include reagents specific for the KLRB1, KLRC2, KLRC3, KLRD1, and KLRK1 genes; and
the expression levels of the KLRB1, KLRC2, KLRC3, KLRD1, and KLRK1 genes are measured.

9. The method as claimed in claim 8, wherein:
the one or more reagents further include at least one reagent selected from the group consisting of reagents specific for the GZMB, CD247, RRAS2, SH2D1B, and LCK genes; and
the expression level of at least one of the GZMB, CD247, RRAS2, SH2D1B, or LCK genes is measured.

10. The method as claimed in claim 8, wherein:
the one or more reagents further include reagents specific for the GZMB, CD247, RRAS2, SH2D1B, and LCK genes; and
the expression levels of the GZMB, CD247, RRAS2, SH2D1B, and LCK genes are measured.

11. The method as claimed in claim 1, wherein:
the one or more reagents further include at least one reagent selected from the group consisting of reagents specific for the KLRB1, KLRC2, KLRC3, KLRD1, KLRK1, CD247, RRAS2, SH2D1B, LCK, MRPS6, SPRY4, CYBB, DUSP2, PDE4D, SH2D2A, GZMB, INSR, ITGAM, VCAN, CD163, P2RY10, CD226, MRPL10, ITPRIPL2, CD2, and NUDT16 genes; and the expression level of at least one of the KLRB1, KLRC2, KLRC3, KLRD1, KLRK1, CD247, RRAS2, SH2D1B, LCK, MRPS6, SPRY4, CYBB, DUSP2, PDE4D, SH2D2A, GZMB, INSR, ITGAM, VCAN, CD163, P2RY10, CD226, MRPL10, ITPRIPL2, CD2, or NUDT16 genes is measured.

12. The method as claimed in claim 1, wherein:

the one or more reagents further include reagents specific for the KLRB1, KLRC2, KLRC3, KLRD1, KLRK1, CD247, RRAS2, SH2D1B, LCK, MRPS6, SPRY4, CYBB, DUSP2, PDE4D, SH2D2A, GZMB, INSR, ITGAM, VCAN, CD163, P2RY10, CD226, MRPL10, ITPRIPL2, CD2, and NUDT16 genes; and the expression levels of the KLRB1, KLRC2, KLRC3, KLRD1, KLRK1, CD247, RRAS2, SH2D1B, LCK, MRPS6, SPRY4, CYBB, DUSP2, PDE4D, SH2D2A, GZMB, INSR, ITGAM, VCAN, CD163, P2RY10, CD226, MRPL10, ITPRIPL2, CD2, and NUDT16 genes are measured.

13. A method comprising:

extracting total RNA from a peripheral blood sample obtained from a patient suspected of having or having colorectal cancer;

contacting the total RNA, or cDNA or cRNA obtained from the total RNA, with reagents specific for a plurality of target genes and no more than 100 target genes; and measuring the expression levels of the plurality of target genes and no more than 100 target genes, wherein the plurality of target genes and no more than 100 target genes include the NEAT1, DUSP2, PDE4D, SH2D2A, GZMB, ITGAM, P2RY10, ITPRIPL2, and NUDT16 genes.

14. The method as claimed in claim 13, wherein the reagents comprise hybridization probes.

15. The method as claimed in claim 13, wherein the reagents comprise hybridization probes and primers.

* * * * *

SEQUENCE LISTING

```
<160> NUMBER OF SEQ ID NOS: 59

<210> SEQ ID NO 1
<211> LENGTH: 1447
<212> TYPE: DNA
<213> ORGANISM: human

<400> SEQUENCE: 1
gagtttgttc ttacacacaa gtttaatgcc accttcctct gtctgccatg gaccaacaag      60
caatatatgc tgagttaaac ttacccacag actcaggccc agaaagttct tcaccttcat     120
ctcttcctcg ggatgtctgt cagggttcac cttggcatca atttgccctg aaacttagct     180
gtgctgggat tattctcctt gtcttggttg ttactgggtt gagtgtttca gtgacatcct     240
taatacagaa atcatcaata gaaaaatgca gtgtggacat tcaacagagc aggaataaaa     300
caacagagag accgggtctc ttaaactgcc caatatattg gcagcaactc cgagagaaat     360
gcttgttatt ttctcacact gtcaacccct ggaataacag tctagctgat tgttccacca     420
aagaatccag cctgctgctt attcgagata aggatgaatt gatacacaca cagaacctga     480
tacgtgacaa agcaattctg ttttggattg gattaaattt ttcattatca gaaaagaact     540
ggaagtggat aaacggctct tttttaaatt ctaatgactt agaaattaga ggtgatgcta     600
```

| | |
|---|---|
| aagaaaacag ctgtatttcc atctcacaga catctgtgta ttctgagtac tgtagtacag | 660 |
| aaatcagatg gatctgccaa aaagaactaa cacctgtgag aaataaagtg tatcctgact | 720 |
| cttgactatg aatcccatct caatttattt gcttcccatt actgatctct gtacttgtag | 780 |
| ctgcacatac tattggtact acctaatagt gccacattta gtggcacaaa gtgaacaatt | 840 |
| ctgagaattg acaactgtta tgaatcttac agaagttcat gtttatcata ttcattctat | 900 |
| taaatgagga aacagagaca tagagaaaaa cgtgcatcgt tttaaagaaa cagtgatatt | 960 |
| ctatggtgaa ggagtgaagg atgtccccga atatgccaga ttggtatatg attgttttgt | 1020 |
| gtttaaaaca gtggagaaat tgtagattca gaaagggaga gctgacctgt ctcttcccgc | 1080 |
| acgcggcaag ccgtgaagat tcctctggga gggctatccg agtcatacaa gggcaagaaa | 1140 |
| atagctctta tcgccagaga cctgaattg gatgctgcaa tgaacctgaa taaagatact | 1200 |
| taataaacac ctatctttca cctatttac agccccccgc aaccaatata tctcctagtg | 1260 |
| actcctctag aaaatttatt gccctagcc agcttttctt catcctgtca tttcttttca | 1320 |
| aatttatcat tcttggtcta aaaagcataa aagcatcttg cttaggccac ttctatggat | 1380 |
| ttcactctct tgcgagttcc tcatgtacat gcaaaacgaa taaaatgtgt atactttat | 1440 |
| tttgttc | 1447 |

<210> SEQ ID NO 2
<211> LENGTH: 1209
<212> TYPE: DNA
<213> ORGANISM: human

<400> SEQUENCE: 2

| | |
|---|---|
| tgcagagatg aataaacaaa gaggaacctt ctcagaagtg agtctggccc aggacccaaa | 60 |
| gcggcagcaa aggaaaccta aaggcaataa aagctccatt tcaggaaccg aacaggaaat | 120 |
| attccaagta gaattaaatc ttcaaaatcc ttccctgaat catcaaggga ttgataaaat | 180 |
| atatgactgc caaggtttac tgccacctcc agagaagctc actgccgagg tcctaggaat | 240 |
| catttgcatt gtcctgatgg ccactgtgtt aaaaacaata gttcttattc ctttcctgga | 300 |
| gcagaacaat tcttccccaa atacaagaac ccagaaaaca cgtcattgtg gccattgtcc | 360 |
| tgaggagtgg attacatatt ccaacagttg ttattacatt ggtaaggaaa gaagaacttg | 420 |
| ggaagagagt ttgctggcct gtacttcgaa gaactccagt ctgctttcta tagataatga | 480 |
| agaagaaatg aaatttctgg ccagcatttt accttcctca tggattggtg tgtttcgtaa | 540 |
| cagcagtcat catccatggg tgacaataaa tggtttggct ttcaaacata agataaaaga | 600 |
| ctcagataat gctgaactta actgtgcagt gctacaagta aatcgactta aatcagccca | 660 |
| gtgtggatct tcaatgatat atcattgtaa gcataagctt tagaagtaaa gcatttgcgt | 720 |
| ttgcagtgca tcagatacat tttatatttc ttaaaataga aatattatga ttgcataaat | 780 |
| ctgaaaatga attatgttat ttgctctgat acaaaaattc taaatcaatt attgaaatag | 840 |
| gatgcacaca attactaaag tacagacatc ctagcatttg tgtcgggctc attttgctca | 900 |
| acatggtatt tgtggttttc agcctttcta aaagttgcat gttatgtgag tcagcttata | 960 |
| ggaagtacca agaacagtca aacccatgga gacagaaagt agaatagtgg ttgccaatgt | 1020 |
| ctcagggagg ttgaaatagg agatgaccac taattgatag aacgtttctt tgtgtcgtga | 1080 |
| tgaaaacttt ctaaatttca gtagtggtga tggttgtaac tctgcgaata tactaaacat | 1140 |
| cattgatttt taatcatttt aagtgcatga aatgtatgct ttgtacatga cacttcaata | 1200 |
| aagctatcc | 1209 |

<210> SEQ ID NO 3
<211> LENGTH: 1209
<212> TYPE: DNA
<213> ORGANISM: human

<400> SEQUENCE: 3

| | | | | | |
|---|---|---|---|---|---|
| tgcagagatg | aataaacaaa | gaggaacctt | ctcagaagtg | agtctggccc | aggacccaaa | 60
| gcggcagcaa | aggaaaccta | aaggcaataa | aagctccatt | tcaggaaccg | aacaggaaat | 120
| attccaagta | gaattaaatc | ttcaaaatcc | ttccctgaat | catcaaggga | ttgataaaat | 180
| atatgactgc | caaggtttac | tgccacctcc | agagaagctc | actgccgagg | tcctaggaat | 240
| catttgcatt | gtcctgatgg | ccactgtgtt | aaaaacaata | gttcttattc | ctttcctgga | 300
| gcagaacaat | ttttccccga | atacaagaac | gcagaaagca | cgtcattgtg | gccattgtcc | 360
| tgaggagtgg | attacatatt | ccaacagttg | ttattacatt | ggtaaggaaa | gaagaacttg | 420
| ggaagagagt | ttgctggcct | gtacttcgaa | gaactccagt | ctgctttcta | tagataatga | 480
| agaagaaatg | aaatttctgg | ccagcatttt | accttcctca | tggattggtg | tgtttcgtaa | 540
| cagcagtcat | catccatggg | tgacaataaa | tggtttggct | ttcaaacata | agataaaaga | 600
| ctcagataat | gctgaactta | actgtgcagt | gctacaagta | aatcgactta | aatcagccca | 660
| gtgtggatct | tcaatgatat | atcattgtaa | gcataagctt | tagaagtaaa | gcatttgcgt | 720
| ttgcagtgca | tcagatacat | tttatatttc | ttaaaataga | aatattatga | ttgcataaat | 780
| ctgaaaatga | attatgttat | ttgctctgat | acaaaaattc | taaatcaatt | attgaaaatag | 840
| gatgcacaca | attactaaag | tacagacatc | ctagcatttg | tgtcgggctc | attttgctca | 900
| acatggtatt | tgtggttttc | agcctttcta | aaagttgcat | gttatgtgag | tcagcttata | 960
| ggaagtacca | agaacagtca | aacccatgga | gacagaaagt | agaatagtgg | ttgccaatgt | 1020
| ctcagggagg | ttgaaatagg | agatgaccac | taattgatag | aacgtttctt | tgtgtcgtga | 1080
| tgaaaacttt | ctaaatttca | gtagtggtga | tggttgtaac | tctgcgaata | tactaaacat | 1140
| cattgatttt | taatcatttt | aagtgcatga | aatgtatgct | ttgtacatga | cacttcaata | 1200
| aagctatcc | | | | | 1209

<210> SEQ ID NO 4
<211> LENGTH: 881
<212> TYPE: DNA
<213> ORGANISM: human

<400> SEQUENCE: 4

| | | | | | |
|---|---|---|---|---|---|
| atgataccaa | cacgtcattg | tggccattgt | cctgaggagt | ggattacata | ttccaacagt | 60
| tgttattaca | ttggtaagga | aagaagaact | tgggaagaga | gtttgctggc | ctgtacttcg | 120
| aagaactcca | gtctgctttc | tatagataat | gaagaagaaa | tgaaatttct | ggccagcatt | 180
| ttaccttcct | catggattgg | tgtgtttcgt | aacagcagtc | atcatccatg | ggtgacaata | 240
| aatggtttgg | ctttcaaaca | taagataaaa | gactcagata | atgctgaact | taactgtgca | 300
| gtgctacaag | taaatcgact | taaatcagcc | cagtgtggat | cttcaatgat | atatcattgt | 360
| aagcataagc | tttagaagta | aagcatttgc | gtttgcagtg | catcagatac | attttatatt | 420
| tcttaaaata | gaaatattat | gattgcataa | atctgaaaat | gaattatgtt | atttgctctg | 480
| atacaaaaat | tctaaatcaa | ttattgaaat | aggatgcaca | caattactaa | agtacagaca | 540
| tcctagcatt | tgtgtcgggc | tcattttgct | caacatggta | tttgtggttt | tcagcctttc | 600

-continued

```
taaaagttgc atgttatgtg agtcagctta taggaagtac caagaacagt caaacccatg    660
gagacagaaa gtagaatagt ggttgccaat gtctcaggga ggttgaaata ggagatgacc    720
actaattgat agaacgtttc tttgtgtcgt gatgaaaact ttctaaattt cagtagtggt    780
gatggttgta actctgcgaa tatactaaac atcattgatt tttaatcatt ttaagtgcat    840
gaaatgtatg ctttgtacat gacacttcaa taaagctatc c                        881

<210> SEQ ID NO 5
<211> LENGTH: 843
<212> TYPE: DNA
<213> ORGANISM: human

<400> SEQUENCE: 5
gcagttatca tagagcacag tccctcacat cacacagctg cagagatgag taaacaaaga     60
ggaaccttct cagaagtgag tctggcccag gacccaaagt ggcagcaaag gaaacctaaa    120
ggcaataaaa gctccatttc aggaaccgaa caggaaatat tccaagtaga attaaacctt    180
caaaatgctt ctctgaatca tcaagggatt gataaaatat atgactgcca aggtttactg    240
ccacctccag aaaagctcac tgccgaggtc ctaggaatca tttgcattgt cctgatggcc    300
actgtgttaa aaacaatagt tcttattcct ttcctggagc agaacaattc ttccccgaat    360
gcaagaaccc agaaagcacg tcattgtggc cattgtcctg aggagtggat tacatattcc    420
aacagttgtt attacattgg taaggaaaga agaacttggg aagagagttt gcaggcctgt    480
gcttcaaaga actcttctag tctgctttgt atagataatg aagaagaaat gaatttctg     540 gccagcattt taccttcctc atggattggt gtgtttcgta acagcagtca tcatccatgg    600
gtgacaataa atggtttggc tttcaaacat gagataaaag actcagatca tgctgaacgt    660
aactgtgcaa tgctacatgt acgtggactt atatcagacc agtgtggatc ttcaagaatc    720
attgtgagca taagctttag aattaaagcg cttgagcttg cagtgcatca gataaaattt    780
tatatttgtt caaacagaaa tgatattatg attgcataag ccttaaaatg aattgtgtta    840
ttt                                                                  843

<210> SEQ ID NO 6
<211> LENGTH: 1018
<212> TYPE: DNA
<213> ORGANISM: human

<400> SEQUENCE: 6
gcagttatca tagagcacag tccctcacat cacacagctg cagagatgag taaacaaaga     60
ggaaccttct cagaagtgag tctggcccag gacccaaagt ggcagcaaag gaaacctaaa    120
ggcaataaaa gctccatttc aggaaccgaa caggaaatat tccaagtaga attaaacctt    180
caaaatgctt ctctgaatca tcaagggatt gataaaatat atgactgcca aggtttactg    240
ccacctccag aaaagctcac tgccgaggtc ctaggaatca tttgcattgt cctgatggcc    300
actgtgttaa aaacaatagt tcttattcct ttcctggagc agaacaattc ttccccaaat    360
acaagaaccc agaaaacacg tcattgtggc cattgtcctg aggagtggat tacatattcc    420
aacagttgtt attacattgg taaggaaaga agaacttggg aagagagttt gcaggcctgt    480
gcttcaaaga actcttctag tctgctttgt atagataatg aagaagaaat gaatttctg     540 gccagcattt taccttcctc atggattggt gtgtttcgta acagcagtca tcatccatgg    600
gtgacaataa atggtttggc tttcaaacat gagataaaag actcagatca tgctgaacgt    660
aactgtgcaa tgctacatgt acgtggactt atatcagacc agtgtggatc ttcaagaatc    720
```

```
attagacggg gtttcatcat gttgaccagg ctggtcttga actcctgagc tcaagaaatc    780
aacacatctt ggcctcccaa gttgctggga ttactgacac aagccaccgc ccctgagtgc    840
tcatgtacca tttagcttgt gttttaaaaa tctactttt ctgccctccc tattttaac     900 tagatgatgt tttaaaaatt acttttccct ctctatatag tttgatttaa gcattagtca    960
tttacaacaa atattaatat taaaatgcag accgttatga ttggaaaata aatcaatg    1018
```

<210> SEQ ID NO 7
<211> LENGTH: 1018
<212> TYPE: DNA
<213> ORGANISM: human

<400> SEQUENCE: 7

```
gcagttatca tagagcacag tccctcacat cacacagctg cagagatgag taaacaaaga     60
ggaaccttct cagaagtgag tctggcccag acccaaagt ggcagcaaag gaaacctaaa    120
ggcaataaaa gctccatttc aggaaccgaa caggaaatat tccaagtaga attaaacctt    180
caaaatgctt ctctgaatca tcaagggatt gataaaatat atgactgcca aggtttactg    240
ccacctccag aaaagctcac tgccgaggtc ctaggaatca tttgcattgt cctgatggcc    300
actgtgttaa aaacaatagt tcttattcct ttcctggagc agaacaattc ttccccgaat    360
gcaagaaccc agaaagcacg tcattgtggc cattgtcctg aggagtggat tacatattcc    420
aacagttgtt attacattgg taaggaaaga agaacttggg aagagagttt gcaggcctgt    480
gcttcaaaga actcttctag tctgctttgt atagataatg aagaagaaat gaaatttctg    540
gccagcattt taccttcctc atggattggt gtgtttcgta acagcagtca tcatccatgg    600
gtgacaataa atggtttggc tttcaaacat gagataaaag actcagatca tgctgaacgt    660
aactgtgcaa tgctacatgt acgtggactt atatcagacc agtgtggatc ttcaagaatc    720
attagacggg gtttcatcat gttgaccagg ctggtcttga actcctgagc tcaagaaatc    780
aacacatctt ggcctcccaa gttgctggga ttactgacac aagccaccgc ccctgagtgc    840
tcatgtacca tttagcttgt gttttaaaaa tctactttt ctgccctccc tattttaac     900 tagatgatgt tttaaaaatt acttttccct ctctatatag tttgatttaa gcattagtca    960
tttacaacaa atattaatat taaaatgcag accgttatga ttggaaaata aatcaatg    1018
```

<210> SEQ ID NO 8
<211> LENGTH: 3258
<212> TYPE: DNA
<213> ORGANISM: human

<400> SEQUENCE: 8

```
ctgtattgtg gttcctggaa cacttcagag gcttgtgatt ctactgcttc ttattcacac     60
tataatacat gtctcaccaa tagatgattc aagaacatca tttaaataca caattttca    120 ttctctattt ttgctaaatt tcttcatact caactttcag attctttaat ctccagctca    180
gcttcaacaa ttcaacgctg ttctttctga aaaagtacac atcgtgcctt ctctacttcg    240
ctcttggaac ataatttctc atggcagtgt ttaagaccac tctgtggagg ttaatttctg    300
ggaccttagg gataatatgc cttcgttga tgtctacgtt gggaattttg ttgaaaaatt    360
cttttactaa actgagtatt gagccagcat ttactccagg acccaacata gaactccaga    420
aagactctga ctgctgttct tgccaagaaa aatgggttgg gtaccggtgc aactgttact    480
tcatttccag tgaacagaaa acttggaacg aaagtcggca tctctgtgct tctcagaaat    540
```

```
ccagcctgct tcagcttcaa aacacagatg aactggattt tatgagctcc agtcaacaat    600
tttactggat tggactctct tacagtgagg agcacaccgc ctggttgtgg gagaatggct    660
ctgcactctc ccagtatcta tttccatcat ttgaaacttt taatacaaag aactgcatag    720
cgtataatcc aaatggaaat gctttagatg aatcctgtga agataaaaat cgttatatct    780
gtaagcaaca gctcatttaa atgtttcttg gggcagagaa ggtggagagt aaagacccaa    840
cattactaac aatgatacag ttgcatgtta tattattact aattgtctac ttctggagtc    900
tataaaatgt ttttaaacag tgtcatatac aattgtcatg tatgtgaaac aatgtgtttt    960
aaaattgatg aaattcgttc acctacattt gagaattata aaattaacat aaagaatttt   1020
gtattttcat ttaatgtata tatttaatgt taaattcaat gtagttttat tacacattta   1080
tgtaattttta tttacattct tgctaattct cagcagaaat ttaaataaga tttaattcac   1140
atcaaataaa atttagaaaa taaaatttaa ctcacactgc ccaggctgga gcatagtggc   1200
aagatcatag ctcattgcaa gctcaagtga tcctcctgac tcagcctccc aagtagctag   1260
gactgcaggc accatgtcac tatgcccgac taatttttaa ttttttaattt tttgtcaaga   1320
caaggtcttg ctatgttgcc caggctggtc ttgaactcct ggcctcaagg gattctccca   1380
ccttggattc ccaaagtgct gggattatag gtgtgaacca ccatccctgg ccctcttcac   1440
attcttgtat gaagattgat ttgggaaaaa tgcatttcag gtaactgaca aaagatatag   1500
gatgaaaaat aatatctttc aaatgtttaa tttgaactaa gagagcttat gcattgcact   1560
ttctggagat ttgtaatgtt ttggttttgt tgtccatgtg actacaaaat aatatatttt   1620
ttaattaaaa aatttaaaat aatacaggca agcatgtaat gattatcaat attttttttcc   1680
accaactatc ctatacccct gacctccttt cattaggcat tatcttctgt tttgatttta   1740
acacttagag tggttttctc tgttatgaat caaagctgat ctattttcat cattttttgtg   1800
atgaaaaaat taattttgat tgacttagga tggaaggatt tggactgggt gtggtggttt   1860
atgcctgtaa tcgcagcact ttgggaggcc aaggcgggtg gatcacttga ggtcaggagt   1920
ttgagaccag cctggccaac atggtgaaac cctgtctcta ctaaaaatac aaaaattggc   1980
tgggtgtggt agtgcacacc tgtaatccca gctatttggg aggctgagtc gagaggatcg   2040
cttgaaccta ggaggtggag gttgcagtga gtcgagattg caccactgca ctccagcctg   2100
ggtgacagag ccagactcct ctccaaaaaa aaaaaaaaa aaaaagatg aaaggatttg   2160
gaaccttaat tgcatctgaa aaactgcctc acctttgtta tttagtgtac tccaaccacg   2220
gagtaacatc ccatcataat cccaaatcct actcaaacaa aaggggaagg gattatgcag   2280
gtgtacacta ggccactggt gtaccaatta gaaaccactt tagagttatg cctactgtac   2340
ccacataatc ctaaaaatat gttacaactg ctacttcata gtttatgcca cttattttat   2400
tttttacttt tattatttttt ttttctgaga cacggtttca ttcccattgc ccaggctgta   2460
gtgcaatgat gcaatcatgg ttcactgcag cttcaacttc ccaggctcaa gggatcctcc   2520
cacctcagcc ttctgagtac ttgggactca ggtgcgagcc atcatgctca gctaatttt   2580
tgtatcattt gtagaaatgg ggttttgtat tgttgcccag gctgatcttg aactcctggg   2640
gtcaaggatt ctgcccgcct tggcctccta aagggctgga attacaggca taagccactg   2700
tgcccggcca gtttatataa tttaaacact gccttttggt tccttgattc ccatatgcta   2760
ggacaagtaa ttattatttt atttttatttt acttttaagtt ctgggttaca tgtgcagaac   2820
ctgcaggttt gttacatagg tatacatgtt ccaaggtggt ttgctgcacc tattgaccca   2880
tcatctaggt tttaagtccc acatgcatta ggtatttgtc ctaatgctct tcctcccctt   2940
```

-continued

| | |
|---|---|
| gccccccacc ccccgacagg ccttggtctg tgatgttcac ctccctgtgt ccatgtgttc | 3000 |
| tcattgttca actcccactt attagtaaga acatgtggtg tttggttttc tgttcctgtg | 3060 |
| ttagtttgct gagaatgatg gtttccagct tcatccatgt cgctgcaaag gacatgaact | 3120 |
| cattcttttt atggctgcat agtattccat ggtgtatatg tgccatattt tctttatcca | 3180 |
| gtctatcact gatgggcatt tgggttggtt ccaagtcttt gctatggtaa atagtgctgc | 3240 |
| aataaacata cgtgtgca | 3258 |

<210> SEQ ID NO 9
<211> LENGTH: 292
<212> TYPE: DNA
<213> ORGANISM: human

<400> SEQUENCE: 9

| | |
|---|---|
| caattcaacg ctgttctttc tgaaaaagta cacatcgtgc cttctctact tcgctcttgg | 60 |
| aacataattt ctcatggcag tgtttaagac cactctgtgg aggttaattt ctgggacctt | 120 |
| agggataata tgcctttcgt tgatgtctac gttgggaatt ttgttgaaaa attctttac | 180 |
| taaactgagt attgagccag catttactcc aggacccaac atagaactcc agaaagcagg | 240 |
| attttatgag ctccagtcaa caattttact ggattggact ctcttacagt ga | 292 |

<210> SEQ ID NO 10
<211> LENGTH: 3165
<212> TYPE: DNA
<213> ORGANISM: human

<400> SEQUENCE: 10

| | |
|---|---|
| ctgtattgtg gttcctggaa cacttcagag gcttgtgatt ctactgcttc ttattcacac | 60 |
| tataatacat gtctcaccaa tagatgattc aagaacatca tttaaataca caattttca | 120 |
| ttctctattt ttgctaaatt tcttcatact caactttcag attctttaat ctccagctca | 180 |
| gcttcaacaa ttcaacgctg ttcttttctga aaaagtacac atcgtgcctt ctctacttcg | 240 |
| ctcttggaac ataatttctc atggcagctt ttactaaact gagtattgag ccagcattta | 300 |
| ctccaggacc caacatagaa ctccagaaag actctgactg ctgttcttgc caagaaaaat | 360 |
| gggttgggta ccggtgcaac tgttacttca tttccagtga acagaaaact tggaacgaaa | 420 |
| gtcggcatct ctgtgcttct cagaaatcca gcctgcttca gcttcaaaac acagatgaac | 480 |
| tggattttat gagctccagt caacaatttt actggattgg actctcttac agtgaggagc | 540 |
| acaccgcctg gttgtgggag aatggctctg cactctccca gtatctattt ccatcatttg | 600 |
| aaactttaa tacaaagaac tgcatagcgt ataatccaaa tggaaatgct ttagatgaat | 660 |
| cctgtgaaga taaaaatcgt tatatctgta agcaacagct catttaaatg tttcttgggg | 720 |
| cagagaaggt ggagagtaaa gacccaacat tactaacaat gatacagttg catgttatat | 780 |
| tattactaat tgtctacttc tggagtctat aaaatgtttt taaacagtgt catatacaat | 840 |
| tgtcatgtat gtgaaacaat gtgttttaaa attgatgaaa ttcgttcacc tacatttgag | 900 |
| aattataaaa ttaacataaa gaattttgta ttttcattta atgtatatat ttaatgttaa | 960 |
| attcaatgta gttttattac acattatgt aatttattt acattcttgc taattctcag | 1020 |
| cagaaattta ataagatttt aattcacatc aaataaaatt tagaaaataa atttaactc | 1080 |
| acactgccca ggctggagca tagtggcaag atcatagctc attgcaagct caagtgatcc | 1140 |
| tcctgactca gcctcccaag tagctaggac tgcaggcacc atgtcactat gcccgactaa | 1200 |

```
tttttaattt ttaatttttt gtcaagacaa ggtcttgcta tgttgcccag gctggtcttg    1260
aactcctggc ctcaagggat tctcccacct tggattccca agtgctggg  attataggtg    1320 tgaaccacca tccctggccc tcttcacatt cttgtatgaa gattgatttg ggaaaaatgc    1380
atttcaggta actgacaaaa gatataggat gaaaaataat atcttccaaa tgtttaattt    1440
gaactaagag agcttatgca ttgcactttc tggagatttg taatgttttg gttttgttgt    1500
ccatgtgact acaaaataat atattttta  attaaaaaat ttaaaataat acaggcaagc    1560
atgtaatgat tatcaatatt ttttccacc  aactatccta taccctgac  ctcctttcat    1620 taggcattat cttctgtttt gattttaaca cttagagtgg ttttctctgt tatgaatcaa    1680
agctgatcta ttttcatcat ttttgtgatg aaaaaattaa ttttgattga cttaggatgg    1740
aaggatttgg actgggtgtg gtggtttatg cctgtaatcg cagcactttg ggaggccaag    1800
gcgggtggat cacttgaggt caggagtttg agaccagcct ggccaacatg gtgaaaccct    1860
gtctctacta aaaatacaaa aattggctgg gtgtggtagt gcacacctgt aatcccagct    1920
atttgggagg ctgagtcgag aggatcgctt gaacctagga ggtggaggtt gcagtgagtc    1980
gagattgcac cactgcactc cagcctgggt gacagagcca gactcctctc caaaaaaaaa    2040 aaaaaaaaa  aagatgaaa  ggatttggaa ccttaattgc atctgaaaaa ctgcctcacc    2100
tttgttattt agtgtactcc aaccacggag taacatccca tcataatccc aaatcctact    2160
caaacaaaag gggaagggat tatgcaggtg tacactaggc cactggtgta ccaattagaa    2220
accactttag agttatgcct actgtaccca cataatccta aaaatatgtt acaactgcta    2280
cttcatagtt tatgccactt attttatttt ttactttat  tatttttttt tctgagacac    2340
ggtttcattc ccattgccca ggctgtagtg caatgatgca atcatggttc actgcagctt    2400
caacttccca ggctcaaggg atcctcccac ctcagcctcc tgagtacttg ggactcaggt    2460
gcgagccatc atgctcagct aattttttgt atcatttgta gaaatggggt tttgtattgt    2520
tgcccaggct gatcttgaac tcctggggtc aaggattctg cccgccttgg cctcctaaag    2580
ggctggaatt acaggcataa gccactgtgc ccggccagtt tatataattt aaacactgcc    2640
ttttggttcc ttgattccca tatgctagga caagtaatta ttattttatt ttattttact    2700
ttaagttctg ggttacatgt gcagaacctg caggtttgtt acataggtat acatgttcca    2760
aggtggtttg ctgcacctat tgacccatca tctaggtttt aagtcccaca tgcattaggt    2820
atttgtccta atgctcttcc tcccttgcc  ccccacccc  cgacaggcct tggtctgtga    2880
tgttcacctc cctgtgtcca tgtgttctca ttgttcaact cccacttatt agtaagaaca    2940
tgtggtgttt ggttttctgt tcctgtgtta gtttgctgag aatgatggtt ccagcttca    3000 tccatgtcgc tgcaaaggac atgaactcat tcttttatg  gctgcatagt attccatggt    3060
gtatatgtgc catattttct ttatccagtc tatcactgat gggcatttgg gttggttcca    3120
agtctttgct atggtaaata gtgctgcaat aaacatacgt gtgca                    3165
```

<210> SEQ ID NO 11
<211> LENGTH: 3195
<212> TYPE: DNA
<213> ORGANISM: human

<400> SEQUENCE: 11

```
ctgtattgtg gttcctggaa cacttcagag gcttgtgatt ctactgcttc ttattcacac      60
tataatacat gtctcaccaa tagatgattc aagaacatca tttaaataca caattttca     120 ttctctattt ttgctaaatt tcttcatact caactttcag attctttaat ctccagctca    180
```

```
gcttcaacaa ttcaacgctg ttctttctga aaaagtacac atcgtgcctt ctctacttcg    240
ctcttggaac ataatttctc atggcagtgt ttaagaccac tctgtggagg ttaatttctg    300 ggacctagg gataatatgc ctttcgttga tgtctacgtt gggaattttg ttgaaaaatt     360
actctgactg ctgttcttgc caagaaaaat gggttgggta ccggtgcaac tgttacttca    420
tttccagtga acagaaaact tggaacgaaa gtcggcatct ctgtgcttct cagaaatcca    480
gcctgcttca gcttcaaaac acagatgaac tggattttat gagctccagt caacaatttt    540
actggattgg actctcttac agtgaggagc acaccgcctg gttgtgggag aatggctctg    600
cactctccca gtatctattt ccatcatttg aaacttttaa tacaaagaac tgcatagcgt    660
ataatccaaa tggaaatgct ttagatgaat cctgtgaaga taaaaatcgt tatatctgta    720
agcaacagct catttaaatg tttcttgggg cagagaaggt ggagagtaaa gacccaacat    780
tactaacaat gatacagttg catgttatat tattactaat tgtctacttc tggagtctat    840
aaaatgtttt taaacagtgt catatacaat tgtcatgtat gtgaaacaat gtgttttaaa    900
attgatgaaa ttcgttcacc tacatttgag aattataaaa ttaacataaa gaattttgta    960
ttttcattta atgtatatat ttaatgttaa attcaatgta gttttattac acatttatgt   1020
aattttattt acattcttgc taattctcag cagaaattta ataagatttt aattcacatc   1080
aaataaaatt tagaaaataa aatttaactc acactgccca ggctggagca tagtggcaag   1140
atcatagctc attgcaagct caagtgatcc tcctgactca gcctcccaag tagctaggac   1200
tgcaggcacc atgtcactat gcccgactaa tttttaattt ttaattttt gtcaagacaa    1260 ggtcttgcta tgttgcccag gctggtcttg aactcctggc tcaagggat tctcccacct    1320 tggattccca aagtgctggg attataggtg tgaaccacca tccctggccc tcttcacatt   1380
cttgtatgaa gattgatttg ggaaaaatgc atttcaggta actgacaaaa gatataggat   1440 gaaaataat atcttttcaaa tgtttaattt gaactaagag agcttatgca ttgcactttc   1500
tggagatttg taatgttttg gttttgttgt ccatgtgact acaaaataat atatttttta   1560
attaaaaaat ttaaataat acaggcaagc atgtaatgat tatcaatatt tttttccacc   1620
aactatccta taccctgac ctcctttcat taggcattat cttctgttt gattttaaca    1680 cttagagtgg ttttctctgt tatgaatcaa agctgatcta ttttcatcat ttttgtgatg   1740
aaaaaattaa ttttgattga cttaggatgg aaggatttgg actgggtgtg gtggtttatg   1800
cctgtaatcg cagcactttg ggaggccaag gcgggtggat cacttgaggt caggagtttg   1860
agaccagcct ggccaacatg gtgaaaccct gtctctacta aaaatacaaa aattggctgg   1920
gtgtggtagt gcacacctgt aatcccagct atttgggagg ctgagtcgag aggatcgctt   1980
gaacctagga ggtggaggtt gcagtgagtc gagattgcac cactgcactc cagcctgggt   2040
gacagagcca gactcctctc aaaaaaaaaa aaaaaaaaa aaagatgaaa ggatttggaa    2100
ccttaattgc atctgaaaaa ctgcctcacc tttgttattt agtgtactcc aaccacggag   2160
taacatccca tcataatccc aaatcctact caaacaaaag gggaagggat tatgcaggtg   2220
tacactaggc cactggtgta ccaattagaa accactttag agttatgcct actgtaccca   2280
cataatccta aaaatatgtt acaactgcta cttcatagtt tatgccactt attttatttt   2340
ttacttttat tatttttttt tctgagacac ggtttcattc ccattgccca ggctgtagtg   2400
caatgatgca atcatggttc actgcagctt caacttccca ggctcaaggg atcctcccac   2460
ctcagccttc tgagtacttg ggactcaggt gcgagccatc atgctcagct aatttttttgt  2520
```

| | |
|---|---:|
| atcatttgta gaaatggggt tttgtattgt tgcccaggct gatcttgaac tcctggggtc | 2580 |
| aaggattctg cccgccttgg cctcctaaag ggctggaatt acaggcataa gccactgtgc | 2640 |
| ccggccagtt tatataattt aaacactgcc ttttggttcc ttgattccca tatgctagga | 2700 |
| caagtaatta ttatttatt ttatttact ttaagttctg ggttacatgt gcagaacctg | 2760 |
| caggtttgtt acataggtat acatgttcca aggtggtttg ctgcacctat tgacccatca | 2820 |
| tctaggtttt aagtcccaca tgcattaggt atttgtccta atgctcttcc tcccttgcc | 2880 |
| ccccacccc cgacaggcct tggtctgtga tgttcacctc cctgtgtcca tgtgttctca | 2940 |
| ttgttcaact cccacttatt agtaagaaca tgtggtgttt ggttttctgt tcctgtgtta | 3000 |
| gtttgctgag aatgatggtt tccagcttca tccatgtcgc tgcaaaggac atgaactcat | 3060 |
| tcttttatg gctgcatagt attccatggt gtatatgtgc catattttct ttatccagtc | 3120 |
| tatcactgat gggcatttgg gttggttcca agtctttgct atggtaaata gtgctgcaat | 3180 |
| aaacatacgt gtgca | 3195 |

<210> SEQ ID NO 12
<211> LENGTH: 3261
<212> TYPE: DNA
<213> ORGANISM: human

<400> SEQUENCE: 12

| | |
|---|---:|
| ctgtattgtg gttcctggaa cacttcagag gcttgtgatt ctactgcttc ttattcacac | 60 |
| tataatacat gtctcaccaa tagatgattc aagaacatca tttaaataca caattttttca | 120 |
| ttctctattt ttgctaaatt tcttcatact caactttcag attctttaat ctccagctca | 180 |
| gcttcaacaa ttcaacgctg ttcttttctga aaagtacac atcgtgcctt ctctacttcg | 240 |
| ctcttggaac ataatttctc atggcagtgt ttaagaccac tctgtggagg ttaatttctg | 300 |
| ggaccttagg gataatatgc ctttcgttga tgtctacgtt gggaattttg ttgaaaaatt | 360 |
| cttttactaa actgagtatt gagccagcat ttactccagg acccaacata gaactccaga | 420 |
| aagactctga ctgctgttct tgccaagaaa atgggttgg gtaccggtgc aactgttact | 480 |
| tcatttccag tgaacagaaa acttggaacg aaagtcggca tctctgtgct tctcagaaat | 540 |
| ccagcctgct tcagcttcaa aacacagatg aactgcagga ttttatgagc tccagtcaac | 600 |
| aattttactg gattggactc tcttacagtg aggagcacac cgcctggttg tgggagaatg | 660 |
| gctctgcact ctcccagtat ctatttccat catttgaaac tttaatacaa agaactgca | 720 |
| tagcgtataa tccaaatgga aatgctttag atgaatcctg tgaagataaa atcgttata | 780 |
| tctgtaagca acagctcatt taaatgtttc ttggggcaga gaaggtggag agtaaagacc | 840 |
| caacattact aacaatgata cagttgcatg ttatattatt actaattgtc tacttctgga | 900 |
| gtctataaaa tgttttaaa cagtgtcata tacaattgtc atgtatgtga aacaatgtgt | 960 |
| tttaaaattg atgaaattcg ttcacctaca tttgagaatt ataaaattaa cataaagaat | 1020 |
| tttgtatttt catttaatgt atatatttaa tgttaaattc aatgtagttt tattacacat | 1080 |
| ttatgtaatt ttatttacat tcttgctaat tctcagcaga aatttaaata agatttaatt | 1140 |
| cacatcaaat aaaatttaga aaataaaatt taactcacac tgcccaggct ggagcatagt | 1200 |
| ggcaagatca tagctcattg caagctcaag tgatcctcct gactcagcct cccaagtagc | 1260 |
| taggactgca ggcaccatgt cactatgccc gactaatttt taatttttaa ttttttgtca | 1320 |
| agacaaggtc ttgctatgtt gcccaggctg gtcttgaact cctggcctca agggattctc | 1380 |
| ccaccttgga ttcccaaagt gctgggatta taggtgtgaa ccaccatccc tggccctctt | 1440 |

-continued

```
cacattcttg tatgaagatt gatttgggaa aaatgcattt caggtaactg acaaaagata    1500
taggatgaaa aataatatct ttcaaatgtt taatttgaac taagagagct tatgcattgc    1560
actttctgga gatttgtaat gttttggttt tgttgtccat gtgactacaa aataatatat    1620
tttttaatta aaaaatttaa aataatacag gcaagcatgt aatgattatc aatatttttt    1680
tccaccaact atcctatacc cctgacctcc tttcattagg cattatcttc tgttttgatt    1740
ttaacactta gagtggtttt ctctgttatg aatcaaagct gatctatttt catcattttt    1800
gtgatgaaaa aattaatttt gattgactta ggatggaagg atttggactg ggtgtggtgg    1860
tttatgcctg taatcgcagc actttgggag gccaaggcgg gtggatcact tgaggtcagg    1920
agtttgagac cagcctggcc aacatggtga accctgtctc tactaaaaa tacaaaaatt    1980 ggctgggtgt ggtagtgcac acctgtaatc ccagctattt gggaggctga gtcgagagga    2040
tcgcttgaac ctaggaggtg gaggttgcag tgagtcgaga ttgcaccact gcactccagc    2100
ctgggtgaca gagccagact cctctccaaa aaaaaaaaa aaaaaaaaag atgaaaggat    2160
ttggaacctt aattgcatct gaaaaactgc ctcacctttg ttatttagtg tactccaacc    2220
acggagtaac atcccatcat aatcccaaat cctactcaaa caaaggggga agggattatg    2280
caggtgtaca ctaggccact ggtgtaccaa ttagaaacca ctttagagtt atgcctactg    2340
tacccacata atcctaaaaa tatgttcaaa ctgctacttc atagtttatg ccacttattt    2400 tatttttac ttttattatt tttttttctg agacacggtt tcattcccat tgcccaggct    2460
gtagtgcaat gatgcaatca tggttcactg cagcttcaac ttcccaggct caagggatcc    2520
tcccacctca gccttctgag tacttgggac tcaggtgcga gccatcatgc tcagctaatt    2580
ttttgtatca tttgtagaaa tggggttttg tattgttgcc caggctgatc ttgaactcct    2640
ggggtcaagg attctgcccg ccttggcctc ctaaagggct ggaattacag cataagcca    2700 ctgtgcccgg ccagtttata taatttaaac actgcctttt ggttccttga ttcccatatg    2760
ctaggacaag taattattat tttatttat tttactttaa gttctgggtt acatgtgcag    2820
aacctgcagg tttgttacat aggtatacat gttccaaggt ggtttgctgc acctattgac    2880
ccatcatcta ggttttaagt cccacatgca ttaggtattt gtcctaatgc tcttcctccc    2940
cttgcccccc acccccgac aggccttggt ctgtgatgtt cacctccctg tgtccatgtg    3000
ttctcattgt tcaactccca cttattagta agaacatgtg gtgtttggtt ttctgttcct    3060
gtgttagttt gctgagaatg atggtttcca gcttcatcca tgtcgctgca aaggacatga    3120
actcattctt tttatggctg catagtattc catggtgtat atgtgccata ttttctttat    3180
ccagtctatc actgatgggc atttgggttg gttccaagtc tttgctatgg taaatagtgc    3240
tgcaataaac atacgtgtgc a                                              3261
```

<210> SEQ ID NO 13
<211> LENGTH: 1575
<212> TYPE: DNA
<213> ORGANISM: human

<400> SEQUENCE: 13

```
actttcaatt ctagatcagg aactgaggac atatctaaat tttctagttt tatagaaggc      60
ttttatccac aagaatcaag atcttccctc tctgagcagg aatcctttgt gcattgaaga    120
ctttagattc ctctctgcgg tagacgtgca cttataagta tttgatgggg tggattcgtg    180
gtcggaggtc tcgacacagc tgggagatga gtgaatttca taattataac ttggatctga    240
```

| | | |
|---|---|---|
| agaagagtga tttttcaaca cgatggcaaa agcaaagatg tccagtagtc aaaagcaaat | 300 | |
| gtagagaaaa tgcatctcca ttttttttct gctgcttcat cgctgtagcc atgggaatcc | 360 | |
| gtttcattat tatggtaaca atatggagtg ctgtattcct aaactcatta ttcaaccaag | 420 | |
| aagttcaaat tcccttgacc gaaagttact gtggcccatg tcctaaaaac tggatatgtt | 480 | |
| acaaaaataa ctgctaccaa ttttttgatg agagtaaaaa ctggtatgag agccaggctt | 540 | |
| cttgtatgtc tcaaaatgcc agccttctga agtatacag caaagaggac caggatttac | 600 | |
| ttaaactggt gaagtcatat cattggatgg gactagtaca cattccaaca aatggatctt | 660 | |
| ggcagtggga agatggctcc attctctcac ccaacctact aacataatt gaaatgcaga | 720 | |
| agggagactg tgcactctat gcctcgagct ttaaaggcta tatagaaaac tgttcaactc | 780 | |
| caaatacgta catctgcatg caaaggacta tgtaaagatg atcaaccatc tcaataaaag | 840 | |
| ccaggaacag agaagagatt acaccagcgg taacactgcc aactgagact aaaggaaaca | 900 | |
| aacaaaaaca ggacaaaatg accaaagact gtcagatttc ttagactcca caggaccaaa | 960 | |
| ccatagaaca atttcactgc aaacatgcat gattctccaa gacaaagaa gagagatcct | 1020 | |
| aaaggcaatt cagatatccc caaggctgcc tctcccacca caagcccaga gtggatgggc | 1080 | |
| tgggggaggg gtgctgtttt aatttctaaa ggtaggacca cacccaggg gatcagtgaa | 1140 | |
| ggaagagaag gccagcagat cactgagagt gcaaccccac cctccacagg aaattgcctc | 1200 | |
| atgggcaggg ccacagcaga gagacacagc atgggcagtg ccttccctgc ctgtgggggt | 1260 | |
| catgctgcca cttttaatgg gtcctccacc caacggggtc agggaggtgg tgctgcccca | 1320 | |
| gtgggccatg attatcttaa aggcattatt ctccagcctt aagtaagatc ttaggacgtt | 1380 | |
| tcctttgcta tgatttgtac ttgcttgagt cccatgactg tttctcttcc tctctttctt | 1440 | |
| ccttttggaa tagtaatatc catcctatgt ttgtcccact attgtatttt ggaagcacat | 1500 | |
| aacttgtttg gtttcacagg ttcacagtta agaaggaatt ttgcctctga ataaatagaa | 1560 | |
| tcttgagtct catgc | 1575 | |

<210> SEQ ID NO 14
<211> LENGTH: 967
<212> TYPE: DNA
<213> ORGANISM: human

<400> SEQUENCE: 14

| | | |
|---|---|---|
| ggaacatgaa gtcactgagc ctgctccacc tctttcctct cccaagagct aaaagagagc | 60 | |
| aaggaggaaa caacagcagc tccaaccagg gcagccttcc tgagaagatg caaccaatcc | 120 | |
| tgcttctgct ggccttcctc ctgctgccca gggcagatgc aggggagatc atcggggac | 180 | |
| atgaggccaa gccccactcc cgcccctaca tggcttatct tatgatctgg gatcagaagt | 240 | |
| ctctgaagag gtgcggtggc ttcctgatac gagacgactt cgtgctgaca gctgctcact | 300 | |
| gttgggggaag ctccataaat gtcaccttgg gggcccacaa tatcaaagaa caggagccga | 360 | |
| cccagcagtt tatccctgtg aaaagaccca tcccccatcc agcctataat cctaagaact | 420 | |
| tctccaacga catcatgcta ctgcagctgg agagaaaggc caagcggacc agagctgtgc | 480 | |
| agcccctcag gctacctagc aacaaggccc aggtgaagcc agggcagaca tgcagtgtgg | 540 | |
| ccggctgggg gcagacggcc cccctgggaa acactcaca cacactacaa gaggtgaaga | 600 | |
| tgacagtgca ggaagatcga agtgcgaat ctgacttacg ccattattac gacagtacca | 660 | |
| ttgagttgtg cgtgggggac ccagagatta aaaagacttc ctttaagggg gactctggag | 720 | |
| gccctcttgt gtgtaacaag gtgcccagg gcattgtctc ctatggacga aacaatggca | 780 | |

```
tgcctccacg agcctgcacc aaagtctcaa gctttgtaca ctggataaag aaaaccatga    840
aacgctacta actacaggaa gcaaactaag cccccgctgt aatgaaacac cttctctgga    900
gccaagtcca gatttacact gggagaggtg ccagcaactg aataaatacc tcttagctga    960
gtggaaa                                                              967

<210> SEQ ID NO 15
<211> LENGTH: 559
<212> TYPE: DNA
<213> ORGANISM: human

<400> SEQUENCE: 15
atgcaaccaa tcctgcttct gctggccttc ctcctgctgc ccagggcaga tcagctggag     60
agaaaggcca gcggaccag agctgtgcag cccctcaggc tacctagcaa caaggcccag    120
gtgaagccag gcagacatg cagtgtggcc ggctggggc agacggcccc cctgggaaaa    180
cactcacaca cactacaaga ggtgaagatg acagtgcagg aagatcgaaa gtgcgaatct    240
gacttacgcc attattacga cagtaccatt gagttgtgcg tggggggccc agagattaaa    300
aagacttcct ttaagggga ctctggaggc cctcttgtgt gtaacaaggt ggcccagggc    360
attgtctcct atggacgaaa caatggcatg cctccacgag cctgcaccaa agtctcaagc    420
tttgtacact ggataaagaa aaccatgaaa cgctactaac tacaggaagc aaactaagcc    480
cccgctgtaa tgaaacacct tctctggagc caagtccaga tttacactgg agaggtgcc    540 agcaactgaa taaataccct                                                559

<210> SEQ ID NO 16
<211> LENGTH: 816
<212> TYPE: DNA
<213> ORGANISM: human

<400> SEQUENCE: 16
ggaacatgaa gtcactgagc ctgctccacc tctttcctct cccaagagct aaagagagc      60 aaggaggaaa caacagcagc tccaaccagg gcagccttcc tgagaagatg caaccaatcc    120
tgcttctgct ggccttcctc ctgctgccca gggcagatgc aggggagatc atcggggac    180 atgaggccaa gccccactcc cgcccctaca tggcttatct tatgatctgg gatcagaagt    240
ctctgaagag gtgcggtggc ttcctgatac gagacgactt cgtgctgaca gctgctcact    300
gttggggaag actggagaga aaggccaagc ggaccagagc tgtgcagccc ctcaggctac    360
ctagcaacaa ggcccaggtg aagccagggc agacatgcag tgtggccggc tgggggcaga    420
cggcccccct gggaaaacac tcacacacac tacaagaggt gaagatgaca gtgcaggaag    480
atcgaaagtg cgaatctgac ttacgccatt attacgacag taccattgag ttgtgcgtgg    540 ggacccaga gattaaaaag acttccttta aggggactc tggaggccct cttgtgtgta    600
acaaggtggc ccagggcatt gtctcctatg gacgaaacaa tggcatgcct ccacgagcct    660
gcaccaaagt ctcaagcttt gtacactgga taaagaaaac catgaaacgc tactaactac    720
aggaagcaaa ctaagccccc gctgtaatga aacaccttct ctggagccaa gtccagattt    780 acactggag aggtgccagc aactgaataa ataccT                               816

<210> SEQ ID NO 17
<211> LENGTH: 951
<212> TYPE: DNA
<213> ORGANISM: human
```

```
<400> SEQUENCE: 17
ggaacatgaa gtcactgagc ctgctccacc tctttcctct cccaagagct aaaagagagc      60
aaggaggaaa caacagcagc tccaaccagg gcagccttcc tgagaagatg caaccaatcc     120
tgcttctgct ggccttcctc ctgctgccca gggcagatgc aggggagatc atcggggac      180 atgaggccaa gccccactcc cgcccctaca tggcttatct tatgatctgg gatcagaagt     240
ctctgaagag gtgcggtggc ttcctgatac gagacgactt cgtgctgaca gctgctcact     300
gttggggaag ctccataaat gtcaccttgg gggcccacaa tatcaaagaa caggagccga     360
cccagcagtt tatccctgtg aaaagaccca tcccccatcc agcctataat cctaagaact     420
tctccaacga catcatgcta ctgcagctgg agagaaaggc caagcggacc agagctgtgc     480 agccccctcag gctacctagc aacaaggccc aggtgaagcc agggcagaca tgcagtgtgg    540
ccggctgggg gcagacggcc cccctgggaa acactcaca cacactacaa gaggtgaaga      600
tgacagtgca ggaagatcga aagtgcgaat ctgacttacg ccattattac gacagtacca    660
ttgagttgtg cgtgggggac ccagagatta aaaagacttc ctttaagggg gactctggag    720
gccctcttgt gtgtaacaag gtggcccagg gcattgtctc ctatggacga acaatggca     780 tgcctccacg agcctgcacc aaagtctcaa gctttgtaca ctggataaag aaaaccatga    840
aacgctacta actacaggaa gcaaactaag ccccgctgt aatgaaacac cttctctgga     900
gccaagtcca gatttacact gggagaggtg ccagcaactg aataaatacc t             951

<210> SEQ ID NO 18
<211> LENGTH: 6854
<212> TYPE: DNA
<213> ORGANISM: human

<400> SEQUENCE: 18
agtgctgaag aaagagggca ctagtgtaca gcccagatcg catccttgca ccgtctggat      60
tagagctgag gcgtctgcaa gccgagcgtg gccacggtcc tctggccccg ggaccatagc     120
gctgtctacc ccgactcagg tactcagcag catctagctc accgctgcca acacgacttc     180
cactgtactc ttgatcaatt taccttgatg cactaccggt gaagaacggg gactcgaatt     240 ccccttacaaa cgcctccagc ttgtagaggc ggtcgtggag gacccagagg aggagacgaa     300
ggggaaggag gcgtggtgg aggaggcaaa ggccttggac gaccattgtt ggcgaggggc     360
accactccgg gagaggcggc gctgggcgtc ttgggggtgc gcgccgggag cctgcagcgg    420
gaccagcgtg ggaacgcggc tgcaggctg tggacctcgt cctcaccacc atggtcgggc     480
tccttttgtt ttttttccca gcgatctttt tggaggtgtc ccttctcccc agaagccccg     540
gcaggaaagt gttgctggca ggagcgtcgt ctcagcgctc ggtggccaga atggacggag    600
atgtcatcat tggagccctc ttctcagtcc atcaccagcc tccggccgag aaagtgcccg    660
agaggaagtg tggggagatc agggagcagt atggcatcca gagggtggag gccatgttcc    720
acacgttgga taagatcaac gcggacccgg tcctcctgcc caacatcacc ctgggcagtg    780
agatccggga ctcctgctgg cactcttccg tggctctgga acagagcatt gagttcatta    840
gggactctct gatttccatt cgagatgaga aggatgggat caaccggtgt ctgcctgacg    900
gccagtccct ccccccaggc aggactaaga agcccattgc gggagtgatc ggtcccggct     960
ccagctctgt agccattcaa gtgcagaacc tgctccagct cttcgacatc ccccagatcg    1020
cttattcagc cacaagcatc gacctgagtg acaaaacttt gtacaaatac ttcctgaggg    1080
ttgtcccttc tgacactttg caggcaaggg ccatgcttga catagtcaaa cgttacaatt    1140
```

```
ggacctatgt ctctgcagtc cacacggaag ggaattatgg ggagagcgga atggacgctt   1200
tcaaagagct ggctgcccag gaaggcctct gtatcgccca ttctgacaaa atctacagca   1260
acgctgggga gaagagcttt gaccgactct tgcgcaaact ccgagagagg cttcccaagg   1320
ctagagtggt ggtctgcttc tgtgaaggca tgacagtgcg aggactcctg agcgccatgc   1380
ggcgccttgg cgtcgtgggc gagttctcac tcattggaag tgatggatgg gcagacagag   1440
atgaagtcat tgaaggttat gaggtggaag ccaacggggg aatcacgata aagctgcagt   1500
ctccagaggt caggtcattt gatgattatt cctgaaact gaggctggac actaacacga   1560
ggaatccctg gttccctgag ttctggcaac atcggttcca gtgccgcctt ccaggacacc   1620
ttctggaaaa tcccaacttt aaacgaatct gcacaggcaa tgaaagctta agagaaaact   1680
atgtccagga cagtaagatg gggttttgtca tcaatgccat ctatgccatg gcacatgggc   1740
tgcagaacat gcaccatgcc ctctgccctg ccacgtggg cctctgcgat gccatgaagc   1800
ccatcgacgg cagcaagctg ctggacttcc tcatcaagtc ctcattcatt ggagtatctg   1860
gagaggaggt gtggtttgat gagaaaggag acgctcctgg aaggtatgat atcatgaatc   1920
tgcagtacac tgaagctaat cgctatgact atgtgcacgt tggaacctgg catgaaggag   1980
tgctgaacat tgatgattac aaaatccaga tgaacaagag tggagtggtg cggtctgtgt   2040
gcagtgagcc ttgcttaaag gccagatta aggttatacg gaaaggagaa gtgagctgct   2100
gctggatttg cacggcctgc aaagagaatg aatatgtgca agatgagttc acctgcaaag   2160
cttgtgactt gggatggtgg cccaatgcag atctaacagg ctgtgagccc attcctgtgc   2220
gctatcttga gtggagcaac atcgaatcca ttatagccat cgccttttca tgcctgggaa   2280
tccttgttac cttgtttgtc accctaatct ttgtactgta ccgggacaca ccagtggtca   2340
aatcctccag tcgggagctc tgctacatca tcctagctgg catcttcctt ggttatgtgt   2400
gcccattcac tctcattgcc aaacctacta ccacctcctg ctacctccag cgcctcttgg   2460
ttggcctctc ctctgcgatg tgctactctg ctttagtgac taaaaccaat cgtattgcac   2520
gcatcctggc tggcagcaag aagaagatct gcacccggaa gcccaggttc atgagtgcct   2580
gggctcaggt gatcattgcc tcaattctga ttagtgtgca actaacctg gtggtaaccc   2640 tgatcatcat ggaacccct atgcccattc tgtcctaccc aagtatcaag gaagtctacc   2700
ttatctgcaa taccagcaac ctgggtgtgg tggccccttt gggctacaat ggactcctca   2760
tcatgagctg tacctactat gccttcaaga cccgcaacgt gcccgccaac ttcaacgagg   2820
ccaaatatat cgcgttcacc atgtacacca cctgtatcat ctggctagct tttgtgccca   2880
tttactttgg gagcaactac aagatcatca aacttgctt tgcagtgagt ctcagtgtaa   2940
cagtggctct ggggtgcatg ttcactccca agatgtacat cattattgcc aagcctgaga   3000
ggaatgtccg cagtgccttc accacctctg atgttgtccg catgcatgtt ggcgatggca   3060
agctgccctg ccgctccaac actttcctca acatcttccg aagaaagaag caggggcag   3120 ggaatgccaa ttctaatggc aagtctgtgt catggtctga accaggtgga ggacaggtgc   3180
ccaagggaca gcatatgtgg caccgcctct ctgtgcacgt gaagaccaat gagacggcct   3240
gcaaccaaac agccgtcatc aagccctca ctaaaagtta ccaaggctct ggcaagagcc   3300 tgacctttc agataccagc accaagaccc tttacaacgt agaggaggag gaggatgccc   3360
agccgattcg ctttagcccg cctggtagcc ttccatggt ggtgcacagg cgcgtgccaa   3420
gcgcggcgac cactccgcct ctgccgtccc acctgaccgc agaggagacc cccctcttcc   3480
```

```
tggccgaacc agccctcccc aagggcttgc cccctcctct ccagcagcag cagcaacccc    3540
ctccacagca gaaatcgctg atggaccagc tccaggagt ggtcagcaac ttcagtaccg     3600
cgatcccgga ttttcacgcg gtgctggcag gccccgtgg tcccgggaac gggctgcggt     3660
ccctgtaccc gccccgcca cctccgcagc acctgcagat gctgccgctg cagctgagca     3720
cctttgggga ggagctggtc tccccgcccg cggacgacga cgacgacagc gagaggttta    3780
agctcctcca ggagtacgtg tatgagcacg agcgggaagg gaacacggaa gaagacgaac    3840
tggaagagga ggaggaggac ctgcaggcgg ccagcaaact gaccccggat gattcgcctg    3900
cgctgacgcc tccgtcgcct ttccgcgact cggtggcctc gggcagctcg gtgcccagct    3960
cccccgtgtc cgagtcggtg ctctgcaccc ctcccaacgt atcctacgcc tctgtcattc    4020
tgcgggacta caagcaaagc tcttccaccc tgtaagggg aagggtccac atagaaaagc     4080
aagacaagcc agagatctcc cacacctcca gagatgtgca acagctggg aggaaaagcc     4140 tgggagtggg gggcctcgtc gggaggacag gagaccgctg ctgctgctgc cgctactgct    4200
gctgctgcct taagtaggaa gagagggaag gacaccaagc aaaaaatgtt ccaggccagg    4260
attcggattc ttgaattact cgaagccttc tctgggaaga agggaattc tgacaaagca     4320 caattccata tggtatgtaa cttttatcac aaatcaaata gtgacatcac aaacataatg    4380
tcctcttttg cacaattgtg catagatata tatatgccca cacacactgg gccatgcttg    4440
ccaaggaaca gcccacgtgg acatgccagt cggatcatga gttcacctga tggcattcgg    4500
agtgagctgg tggagccaga cagagcaggt gcggggaagg gaagggccca ggccagaccc    4560
atcccaaacg gatgatggga tgatgggaca gcagctcctt gctcagaagc ccttctcccc    4620
gctgggctga cagactcctc atcttcagga gactcaggaa tggagcggca caggggtctc    4680
tcttcatcca ctgcaacccca tccagtgcca gctttgagat tgcacttgaa gaaaggtgca    4740
tggaccccct gctgctctgc agattccctt tatttaggaa acaggaata agagcaaaat     4800 tatcaccaaa aagtgcttca tcaggcgtgc tacaggagga aggagctaga aatagaacaa    4860
tccatcagca tgagactttg aaaaaaaaac acatgatcag cttctcatgt tccatattca    4920
cttattggcg atttggggaa aaggccggaa caagagattg ttacgagagt ggcagaaacc    4980
cttttgtaga ttgacttgtg tttgtgccaa gcgggctttc cattgaccttt cagttaaaga    5040 acaaaccatg tgacaaaatt gttaccttcc acttactgta gcaaataata cctacaagtt    5100
gaacttctaa gatgcgtata tgtacaattt ggtgccatta tttctcctac gtattagaga    5160
aacaaatcca tctttgaatc taatggtgta ctcatagcaa ctattactgg tttaaatgac    5220
aaataattct atcctattgt cactgaagtc cttgtaacta gcgagtgaat gtgttcctgt    5280
gtccttgtat atgtgcgatc gtaaaatttg tgcaatgtaa tgtcaaattg actggtcaat    5340
gtcaacctag tagtcaatct aactgcaatt agaaattgtc ttttgaatat actatatata    5400
ttttttatgt tccaataatg ttttgtacat cattgtcatc aatatctaca gaagctcttt    5460
gacggtttga atactatggc tcaaggtttt catatgcagc tcggatggac attttcttc     5520 taagatggaa cttatttttc agatattttc tgatgtggag atatgttatt aatgaagtgg    5580
tttgaaaatt tgttatatta aaagtgcaca aaaactgaga gtgaaaataa aaggtacatt    5640
ttataagctt gcacacatta ttaacacata agattgaaca aagcatttag attattccag    5700
gttatatcat ttttttaaag attttccaca gctacttgag tgtctaacat acagtaacat    5760
ctaactcagc taataaatttg taaaatcttt atcaatcaca ttttgccttc ttttaatttt    5820
tatgttcatg gacttttatt cctgtgtctt ggctgtcata acttttatt tctgctatttt     5880
```

```
gctgttgtgt aatatccatg gacatgtaat ccacttactc catctttaca atccctttt      5940 accaccaata aaaggatttt tcttgctgtt ttgatttctt ctattatttg tggaatgaat      6000 tataccccc  ttaaatatct tgtttatgc  cttatgttca gtcatatttt aatatgcttc      6060
cttcatattg aagctgctga tttctcagcc aaaaatcatc ttagaatctt taaatatcca      6120
ttgcatcatt tgttcagaat ttaacatcca ttccaatgtt ggaggcttgt attacttata      6180
tttcatcata ttctattgcc aagtttagtc agttccacac caagaatgaa ctgcatttcc      6240
tttaaaaatt attttaaaac acctttattg aaaagatctc atgactgaga tgtggacttt      6300
ggttccatgt tttcattgta agaaagcaga gagcggaaaa tcaatggctc cagtgattaa      6360
tagatgggtt tttagtaatt gacaaattca tgagggaaag catatgatct ctttattagt      6420
gaatcatgct tattttttac tcttaatgcc actaatatac atccctaata tcacagggct      6480
tgtgcattca gattttaaa  aaattaggat agataaggaa acaacttata ttcaagtgta      6540
agatgatatc aggttggtct aagacttttg gtgaacacgt tcattcaact gtgatcactt      6600
tattactctg aatgcctact attatcctga ttatgggtc  tcctgaataa atagagtatt      6660
agtccttatg tcatcattgt tcaaaattgg agatgtacac atacataccc tataccaaga      6720
gggccgaaac tcttcacctt gatgtatgtt ctgatacaag ttgttcagct tcttgtaaat      6780
gtgttttcct tcggcttgtt actgcctttt gtcaaataat cttgacaatg ctgtataata      6840
aatattttct attt                                                       6854

<210> SEQ ID NO 19
<211> LENGTH: 1609
<212> TYPE: DNA
<213> ORGANISM: human

<400> SEQUENCE: 19
ttttctccta accgtcccgg ccaccgctgc ctcagcctct gcctcccagc ctctttctga       60
gggaaaggac aagatgaagt ggaaggcgct tttcaccgcg ccatcctgc  aggcacagtt      120 gccgattaca gaggcacaga gctttggcct gctggatccc aaactctgct acctgctgga      180
tggaatcctc ttcatctatg gtgtcattct cactgccttg ttcctgagag tgaagttcag      240
caggagcgca gacgccccg  cgtaccagca gggccagaac cagctctata acgagctcaa      300
tctaggacga agagaggagt acgatgtttt ggacaagaga cgtggccggg accctgagat      360
ggggggaaag ccgcagagaa ggaagaaccc tcaggaaggc ctgtacaatg aactgcagaa      420
agataagatg gcggaggcct acagtgagat tgggatgaaa ggcgagcgcc ggaggggcaa      480
ggggcacgat ggcctttacc agggtctcag tacagccacc aaggacacct cgacgccct       540 tcacatgcag gccctgcccc ctcgctaaca gccaggggat ttcaccactc aaaggccaga      600
cctgcagacg cccagattat gagacacagg atgaagcatt tacaacccgg ttcactcttc      660
tcagccactg aagtattccc ctttatgtac aggatgcttt ggttatattt agctccaaac      720
cttcacacac agactgttgt ccctgcactc tttaagggag tgtactccca gggcttacgg      780
ccctggcctt gggccctctg gtttgccggt ggtgcaggta gacctgtctc ctggcggttc      840
ctcgttctcc ctgggaggcg ggcgcactgc ctctcacagc tgagttgttg agtctgtttt      900
gtaaagtccc cagagaaagc gcagatgcta gcacatgccc taatgtctgt atcactctgt      960
gtctgagtgg cttcactcct gctgtaaatt tggcttctgt tgtcaccttc acctcctttc     1020
aaggtaactg tactgggcca tgttgtgcct ccctggtgag agggccgggc agaggggcag     1080
```

| | |
|---|---|
| atggaaagga gcctaggcca ggtgcaacca gggagctgca ggggcatggg aaggtgggcg | 1140 |
| ggcaggggag ggtcagccag ggcctgcgag ggcagcggga gcctccctgc ctcaggcctc | 1200 |
| tgtgccgcac cattgaactg taccatgtgc tacaggggcc agaagatgaa cagactgacc | 1260 |
| ttgatgagct gtgcacaaag tggcataaaa acatgtggt tacacagtgt gaataaagtg | 1320 |
| ctgcggagca agaggaggcc gttgattcac ttcacgcttt cagcgaatga caaaatcatc | 1380 |
| tttgtgaagg cctcgcagga agacccaaca catgggacct ataactgccc agcggacagt | 1440 |
| ggcaggacag gaaaaacccg tcaatgtact aggatactgc tgcgtcatta cagggcacag | 1500 |
| gccatggatg gaaaacgctc tctactctgc ttttttcta ctgttttaat ttatactggc | 1560 |
| atgctaaagc cttcctattt tgcataataa atgcttcagt gaaaatgca | 1609 |

<210> SEQ ID NO 20
<211> LENGTH: 1678
<212> TYPE: DNA
<213> ORGANISM: human

<400> SEQUENCE: 20

| | |
|---|---|
| tgctttctca aaggccccac agtcctccac ttcctgggga ggtagctgca gaataaaacc | 60 |
| agcagagact ccttttctcc taaccgtccc ggccaccgct gcctcagcct ctgcctccca | 120 |
| gcctctttct gagggaaagg acaagatgaa gtggaaggcg cttttcaccg cggccatcct | 180 |
| gcaggcacag ttgccgatta cagaggcaca gagctttggc ctgctggatc ccaaactctg | 240 |
| ctacctgctg gatggaatcc tcttcatcta tggtgtcatt ctcactgcct tgttcctgag | 300 |
| agtgaagttc agcaggagcg cagacgcccc cgcgtaccag cagggccaga ccagctcta | 360 |
| taacgagctc aatctaggac aagagagga gtacgatgtt ttggacaaga gacgtggccg | 420 |
| ggaccctgag atgggggaa agccgagaag gaagaaccct caggaaggcc tgtacaatga | 480 |
| actgcagaaa gataagatgg cggaggccta cagtgagatt gggatgaaag gcgagcgccg | 540 |
| gaggggcaag gggcacgatg gccttttacca gggtctcagt acagccacca aggacaccta | 600 |
| cgacgccctt cacatgcagg ccctgccccc tcgctaacag ccagggggatt tcaccactca | 660 |
| aaggccagac ctgcagacgc ccagattatg agacacagga tgaagcattt acaacccggt | 720 |
| tcactcttct cagccactga agtattcccc tttatgtaca ggatgctttg gttatattta | 780 |
| gctccaaacc ttcacacaca gactgttgtc cctgcactct ttaagggagt gtactcccag | 840 |
| ggcttacggc cctggccttg ggccctctgg tttgccggtg gtgcaggtag acctgtctcc | 900 |
| tggcggttcc tcgttctccc tgggaggcgg gcgcactgcc tctcacagct gagttgttga | 960 |
| gtctgttttg taaagtcccc agagaaagcg cagatgctag cacatgccct aatgtctgta | 1020 |
| tcactctgtg tctgagtggc ttcactcctg ctgtaaattt ggcttctgtt gtcaccttca | 1080 |
| cctcctttca aggtaactgt actgggccat gttgtgcctc cctggtgaga gggccgggca | 1140 |
| gaggggcaga tggaaaggag cctaggccag gtgcaaccag ggagctgcag gggcatggga | 1200 |
| aggtgggcgg gcaggggagg gtcagccagg gcctgcgagg gcagcgggag cctccctgcc | 1260 |
| tcaggcctct gtgccgcacc attgaactgt accatgtgct acaggggcca gaagatgaac | 1320 |
| agactgacct tgatgagctg tgcacaaagt ggcataaaaa acatgtggtt acacagtgtg | 1380 |
| aataaagtgc tgcggagcaa gaggaggccg ttgattcact tcacgctttc agcgaatgac | 1440 |
| aaaatcatct ttgtgaaggc ctcgcaggaa gacccaacac atgggaccta taactgccca | 1500 |
| gcggacagtg gcaggacagg aaaaacccgt caatgtacta ggatactgct gcgtcattac | 1560 |
| agggcacagg ccatggatgg aaaacgctct ctactctgct ttttttctac tgtttaatt | 1620 |

```
tatactggca tgctaaagcc ttcctatttt gcataataaa tgcttcagtg aaaatgca      1678
```

<210> SEQ ID NO 21
<211> LENGTH: 2209
<212> TYPE: DNA
<213> ORGANISM: human

<400> SEQUENCE: 21

```
gggagggcgg agctggaagg gtgggaagca ccgatccacc ttattgctct ggccgaggcc      60
agagacctcc gggagaggct gggccaccga gccgggcttt actgctccga gggtccgggc     120
gtggggctgg agctggagcc ccgcgcgctg cttttccagc cgcctgcggc cgcgccttca     180
ccgtcgggc gatagcggtg caacttggc cgcggctccg cgtggtctcc gggcttcccc       240
gcgccgcctg agccggagct gcccgcttca atcctatttt gtaacggatt atgatccaac     300
cattgaagat tcttacacaa agcagtgtgt gatagatgac agagcagccc ggctagatat     360
tttggataca gcaggacaag aagagtttgg agccatgaga gaacagtata tgaggactgg     420
cgaaggcttc ctgttggtct tttcagtcac agatagaggc agttttgaag aaatctataa     480
gtttcaaaga cagattctca gagtaaagga tcgtgatgag ttcccaatga ttttaattgg     540
taataaagca gatctggatc atcaaagaca ggtaacacag aagaaggac aacagttagc      600
acggcagctt aaggtaacat acatggaggc atcagcaaag attaggatga atgtagatca     660
agctttccat gaacttgtcc gggttatcag gaaatttcaa gagcaggaat gtcctccttc     720
accagaacca cacgaaag aaaagacaa gaaaggctgc cattgtgtca ttttctagaa        780
tcccttcagt tttagctacc aacggccagg aaaagccctc atcttctctt tctctcctca     840
gtttacatct tgttggtacc tttctagcct tagacaaatg atcaccatgt tagccttaga     900
cgaagaagct ggctagtcct ttctgtgaag ctaatacaat ggtcatttcc agacaaattt     960
aaaggaaaca ctaaggctgc ttcaaagatt atctgattcc tttaaaatat atgtctatat    1020
acacagacat gctctttttt taagtgctta cattttaata gagatgaatc agttttggaa    1080
tctaagctgt ttgccaagct gaagctacag gttgtgaaat aattttttaac ttttggaatc   1140
atactgccta ctgttactct aaatagaaat atagggtttt ttttaatgtg aattttttgcc   1200
tatctttaaa catttcaatg tcagcctttg ttaaccttaa atacactgaa ttgaatctac    1260
aaaagtgaac catctcagac ctttactgat actacaactt ttgttttctg atggccaaaa    1320
taccaaatgc ctgttgtatt tatggattaa aaactgctta taaaaccctg tgttactact    1380
cctactcttg gagatgataa tattctatgt ggtcaaatat ttggactcat ttaggactta    1440
gatatttcag tgtacttgat ttttttaattt aactcttttt cacagccacg ctaagggtaa   1500
aaaggaataa tttccttctg tcttccttt caagtatttc tgggtaaggg attcaaaaaa      1560
ctaaaactgt ttttgtttgt aatataaaat atggaattga tctttccagg gtcagagatg    1620
attaatgttt ttgctatata cttttataca ttattttctt atcaaactag ttaacaagta    1680
tttttatatg tttgtaagca gatatgcttt catagcatac cttgtgtata tgtaaagata    1740
agtatttaat tctcactgtt cacttttaac tgacaaagaa aaacaagtgg aaactacaga    1800
aactgtggta gaacttttac ttgctggtct ggtcttggtt gtaccatct ttggccagtc     1860
acataactac tcaagaaacc ttcccaatag agtacaacag gatgagactc tgaaatcact    1920
ttcagtattc cctgctagat attgattgtt atttcaagta ttaagtgtaa gcttttaatg    1980
gataattagt ataactgtgg atggcatctg attttgtttt taattctgtg gattgtgttt    2040
```

| aagcaattca ataqtatgtt cctgattttg agatgctaag tggtattgca cagttgtcac | 2100 |
| tttatcaagt gtgtacaaca gtcccatgaa gtttatagag catacccttg tatagcttca | 2160 |
| ggtgctagaa ttaaaattga tctgttatca aagaaaaaa aaaaaaaaa | 2209 |

<210> SEQ ID NO 22
<211> LENGTH: 2360
<212> TYPE: DNA
<213> ORGANISM: human

<400> SEQUENCE: 22

| cagacggcca tttgtggcgg cgctggaggc tgcgttcggc aggcgctgcg gagacgcgta | 60 |
| gaggagcgcg cccccggcc gctgccgccc ctggcccgtg ccgtcacccc gcttctccgc | 120 |
| gcctcgggcg gtacccagcc agtccccagc gccgcgctac cgcgctgacc ggccctccag | 180 |
| acgcctcccg gtacccggga ccccagcccg gccgctcgcc cgcagcccgc cggccgcaca | 240 |
| cgtccccgga gccgggccta gggcgggcgg cagcggcggc tcggcgcagt caggctgggc | 300 |
| tctgtagcgt ccccatggcc gcggccggct ggcgggacgg ctccggccag gagaagtacc | 360 |
| ggctcgtggt ggtcggcggg ggcggcgtgg gcaagtcggc gctcaccatc cagttcatcc | 420 |
| agtcctattt tgtaacggat tatgatccaa ccattgaaga ttcttacaca aagcagtgtg | 480 |
| tgatagatga cagagcagcc cggctagata ttttggatac agcaggacaa gaagagtttg | 540 |
| gagccatgag agaacagtat atgaggactg gcgaaggctt cctgttggtc ttttcagtca | 600 |
| cagatagagg cagttttgaa gaaatctata gtttcaaag acagattctc agagtaaagg | 660 |
| atcgtgatga gttcccaatg attttaattg gtaataaagc agatctggat catcaaagac | 720 |
| aggtaacaca ggaagaagga caacagttag cacggcagct taaggtaaca tacatggagg | 780 |
| catcagcaaa gattaggatg aatgtagatc aagcttttca tgaacttgtc cgggttatca | 840 |
| ggaaattca agagcaggaa tgtcctcctt caccagaacc aacacggaaa gaaaaagaca | 900 |
| agaaaggctg ccattgtgtc attttctaga atcccttcag ttttagctac caacggccag | 960 |
| gaaaagccct catcttctct ttctctcctc agtttacatc ttgttggtac ctttctagcc | 1020 |
| ttagacaaat gatcaccatg ttagccttag acgaagaagc tggctagtcc tttctgtgaa | 1080 |
| gctaatacaa tggtcatttc cagacaaatt taaggaaaac actaaggctg cttcaaagat | 1140 |
| tatctgattc ctttaaaata tatgtctata tacacagaca tgctcttttt ttaagtgctt | 1200 |
| acatttaat agagatgaat cagttttgga atctaagctg tttgccaagc tgaagctaca | 1260 |
| ggttgtgaaa taattttaa cttttggaat catactgcct actgttactc taaatagaaa | 1320 |
| tatagggttt tttttaatgt gaattttgc ctatctttaa acatttcaat gtcagccttt | 1380 |
| gttaacctta aatacactga attgaatcta caaaagtgaa ccatctcaga cctttactga | 1440 |
| tactacaact tttgttttct gatggccaaa ataccaaatg cctgttgtat ttatggatta | 1500 |
| aaaactgctt ataaaaccct gtgttactac tcctactctt ggagatgata atattctatg | 1560 |
| tggtcaaata tttggactca tttaggactt agatattca gtgtacttga tttttaatt | 1620 |
| taactctttt tcacagccac gctaagggta aaaggaata atttccttct gtcttccttt | 1680 |
| tcaagtattt ctgggtaagg gattcaaaaa actaaaactg tttttgtttg taatataaaa | 1740 |
| tatgaattg atctttccag ggtcagagat gattaatgtt tttgctatat acttttatac | 1800 |
| attattttct tatcaaacta gttaacaagt attttatat gtttgtaagc agatatgctt | 1860 |
| tcatagcata ccttgtgtat atgtaaagat aagtatttaa ttctcactgt tcacttttaa | 1920 |
| ctgacaaaga aaaacaagtg gaaactacag aaactgtggt agaacttttta cttgctggtc | 1980 |

| | |
|---|---:|
| tggtcttggt tgtacccatc tttggccagt cacataacta ctcaagaaac cttcccaata | 2040 |
| gagtacaaca ggatgagact ctgaaatcac tttcagtatt ccctgctaga tattgattgt | 2100 |
| tatttcaagt attaagtgta agctttaat ggataattag tataactgtg datggcatct | 2160 |
| gattttgttt ttaattctgt ggattgtgtt taagcaattc aatagtatgt tcctgatttt | 2220 |
| gagatgctaa gtggtattgc acagttgtca ctttatcaag tgtgtacaac agtcccatga | 2280 |
| agtttataga gcatacccctt gtatagcttc aggtgctaga attaaaattg atctgttatc | 2340 |
| acaagaaaaa aaaaaaaaaa | 2360 |

<210> SEQ ID NO 23
<211> LENGTH: 2041
<212> TYPE: DNA
<213> ORGANISM: human

<400> SEQUENCE: 23

| | |
|---|---:|
| gtagctccac aggaggtaca gctgcttaca catctctcct cagagctgtc ccttgacttg | 60 |
| ggggtgaatt tcaggccaac agggcttcct gggatacaag agcgttctcc atggatctgc | 120 |
| cttactacca tggacgtctg accaagcaag actgtgagac cttgctgctc aaggaagggg | 180 |
| tggatggcaa ctttctttta agagacagcg agtcgatacc aggagtcctg tgcctctgtg | 240 |
| tctcgtttaa aaatattgtc tacacatacc gaatcttcag agagaaacac gggtattaca | 300 |
| ggatacagaa cagtaacagc gattatgtgg atgtcttgcc ttgaagataa ggctgccgga | 360 |
| caaagcaagt tgaagagatg agtaacagtt ctcactgatg acccacttct gcaggcatag | 420 |
| gtccagagca ccaaactcta gtggacaatt cagactctcc tggttgtgta actgaagatg | 480 |
| ttctgcccac cagcaccaga ggtcactctc cacatcccccg cctcccagac ataaccagg | 540 |
| agcaatttca aaccctctc cagtttcact cttcttctt ggaatgggac agcctgaaca | 600 |
| tttccccttt gacttgttaa aggtaccacc ctacatcatg gttgacaccc tcctttggac | 660 |
| catgcagtca gaggggcagc tttatacaga ggaggggcac acttgtctgt gagtttgaag | 720 |
| ccctgagttc cagtcctgtg gctgtgtgac tttgaacacg tttctgccca tctccaggtc | 780 |
| ttagttctt tgtctctgtg gttgggtggg atgataaaca ttgccccagt ctctctgttg | 840 |
| agcctgcttg tgtcaggtga aggtgaggga tcgggagtga tggagatgca tacagatcag | 900 |
| caccttctct gtacctgctg gacccccatg tgcacccttc tccctccagc ctgggctact | 960 |
| ctcctcctgg ttctttctaa tcttaaactt cctggtgagc attgccccag ccacactttc | 1020 |
| tccctggttt tgcttaattc cacttatgca tcagtcattt caacagcatg aatgtggttc | 1080 |
| tgtacagtga tgtatgtgga gatttctaaa atattctatg tgtgatttct gttcccaact | 1140 |
| aggttctaag tgccatcaaa gcacggttgg gtctcccttg tatcttccac agtgtgtaga | 1200 |
| aatttgtgct gcccagagct gtgcctagtt catagaaact gactggaagc acattgctga | 1260 |
| gggaggtttg ttgaattggt ttttaaggtt tactgaaatt gatttgctga attttttctgc | 1320 |
| tagttcaaaa tgtgaattag gacctggtca gtttgaaata taccaaattc tatgcccttt | 1380 |
| ctcttaccta tcatcaaatt gtagtaatgt atttcacccc actggactta tcttcagagt | 1440 |
| tttaaaagag aggagctctc gacttagagg taatatgaac agatgaacag acactgtggc | 1500 |
| tggagcccca agtgtggag cattgtgaga tttggggtca cagcaattta tggctactat | 1560 |
| tccctgggtc tggtaggtag gacaaatgtc ctctttttact tttcaaaact ggcttaggta | 1620 |
| ttcatggacc ttgattcttc tatatacatt ttataataaa tacgtgaaat tgcttaaaac | 1680 |

| | |
|---|---|
| ctcttttgg aatttttaat gaacttgcaa caaatttgta aataggagag aactgacgtt | 1740 |
| cttgtgatgt tttcccatgc ataaacatgc cacatccatg ttcttgggtc atcttttttg | 1800 |
| cccttcatg gagtcataaa ttttcccaac tgaagtcttg tatattctgt tagattaatt | 1860 |
| cctatttcta gttgctgtaa atgatatctt atgttttatt acatttctaa taggatatgg | 1920 |
| tgttggtgaa atgttaaccc tctcattaga tctactagtt tacctgttga ttctattgtg | 1980 |
| ttttctatgt aaatgatttt gtcagctata aataataaca ttttattttc tctttccttg | 2040 |
| c | 2041 |

<210> SEQ ID NO 24
<211> LENGTH: 2523
<212> TYPE: DNA
<213> ORGANISM: human

<400> SEQUENCE: 24

| | |
|---|---|
| gtagctccac aggaggtaca gctgcttaca catctctcct cagagctgtc ccttgacttg | 60 |
| ggggtgaatt tcaggccaac agggcttcct gggatacaag agcgttctcc atggatctgc | 120 |
| cttactacca tggacgtctg accaagcaag actgtgagac cttgctgctc aaggaagggg | 180 |
| tggatggcaa ctttcttta agagacagcg agtcgatacc aggagtcctg tgcctctgtg | 240 |
| tctcgtttaa aaatattgtc tacacatacc gaatcttcag agagaaacac gggtattaca | 300 |
| ggatacagac tgcagaaggt tctccaaaac aggtctttcc aagcctaaag gaactgatct | 360 |
| ccaaatttga aaaccaaat caggggatgg tggttcacct tttaaagcca ataaagagaa | 420 |
| ccagccccag cttgagatgg agaggattga aattagagtt ggaaacattt gtgaacagta | 480 |
| acagcgatta tgtggatgtc ttgccttgaa gataaggctg ccggacaaag caagttgaag | 540 |
| agatgagtaa cagttctcac tgatgaccca cttctgcagg cataggtcca gagcaccaaa | 600 |
| ctctagtgga caattcagac tctcctggtt gtgtaactga agatgttctg cccaccagca | 660 |
| ccagaggtca ctctccacat ccccgcctcc cagacatata ccaggagcaa tttcaaaacc | 720 |
| ctctccagtt tcactcttct ttcttggaat gggacagcct gaacattttc cctttgactt | 780 |
| gttaaaggta ccaccctaca tcatggttga caccctcctt tggaccatgc agtcagaggg | 840 |
| gcagctttat acagaggagg ggcacacttg tctgtgagtt tgaagccctg agttccagtc | 900 |
| ctgtggctgt gtgactttga acacgtttct gcccatctcc aggtcttagt ttctttgtct | 960 |
| ctgtggttgg gtgggatgat aaacattgcc ccagtctctc tgttgagcct gcttgtgtca | 1020 |
| ggtgaaggtg agggatcggg agtgatggag atgcatacag atcagcacct tctctgtacc | 1080 |
| tgctggaccc ccatgtgcac ccttctccct ccagcctggg ctactctcct cctggttctt | 1140 |
| tctaatctta aacttcctgg tgagcattgc cccagccaca cttctccct ggttttgctt | 1200 |
| aattccactt atgcatcagt catttcaaca gcatgaatgt ggttctgtac agtgatgtat | 1260 |
| gtggagattt ctaaaatatt ctatgtgtga tttctgttcc caactaggtt ctaagtgcca | 1320 |
| tcaaagcacg gtttgggtctc ccttgtatct tccacagtgt gtagaaattt gtgctgccca | 1380 |
| gagctgtgcc tagttcatag aaactgactg gaagcacatt gctgagggag gtttgttgaa | 1440 |
| ttggttttta aggtttactg aaattgattt gctgaatttt tctgctagtt caaaatgtga | 1500 |
| attaggacct ggtcagtttg aaatatacca aattctatgc cctttctctt acctatcatc | 1560 |
| aaattgtagt aatgtatttc accccactgg acttatcttc agagttttaa aagagaggag | 1620 |
| ctctcgactt agaggtaata tgaacagatg aacagacact gtggctggag ccccaaagtg | 1680 |
| tggagcattg tgagatttgg ggtcacagca atttatggct actattccct gggtctggta | 1740 |

```
ggtaggacaa atgtcctctt ttacttttca aaactggctt aggtattcat ggaccttgat    1800
tcttctatat acattttata ataaatacgt gaaattgctt aaaacctctt tttggaattt    1860
ttaatgaact tgcaacaaat tgtaaatag gagagaactg acgttcttgt gatgttttcc    1920
catgcataaa catgccacat ccatgttctt gggtcatctt ttttgcccttt tcatggagtc   1980 ataaatttttc ccaactgaag tcttgtatat tctgttagat taattcctat ttctagttgc   2040
tgtaaatgat atcttatgtt ttattacatt tctaatagga tatggtgttg gtgaaatgtt    2100
aaccctctca ttagatctac tagtttacct gttgattcta ttgtgttttc tatgtaaatg    2160
attttgtcag ctataaataa taacatttta ttttctcttt ccttgcaata cctatgctca    2220 tttattttttt atgtttaccc attggttagg gcctcctgta tacattaaac agttcatagt    2280
catgatagtg agtattctta cactgttccc agtattacag ggaatgctta gaaattttct    2340
ttatttaaac attatgtttg ttgtagccctt gttaaaggct attttataat ttttactaga    2400
aatattttga catttattgt gattttttc tatctctaat ctattgagat agtcacattc     2460
cttttgtctt cactccatta taaaggtaag ttaccttaat aaaattgttg atatcatttc    2520
atc                                                                   2523

<210> SEQ ID NO 25
<211> LENGTH: 2166
<212> TYPE: DNA
<213> ORGANISM: human

<400> SEQUENCE: 25
gagggctcag agggagcacc ggtttggagc tgggaccccc tattttagct tttctgtggc      60
tggtgaatgg ggatcccagg atctcacaat ctcagggacc atgggctgtg gctgcagctc    120
acacccggaa gatgactgga tggaaaacat cgatgtgtgt gagaactgcc attatcccat    180
agtcccactg gatggcaagg gcacgctgct catccgaaat ggctctgagg tgcgggaccc    240
actggttacc tacgaaggct ccaatccgcc ggcttcccca ctgcaagaca acctggttat    300
cgctctgcac agctatgagc cctctcacga cggagatctg ggctttgaga aggggaaca    360 gctccgcatc ctggagcaga gcggcgagtg gtggaaggcg cagtccctga ccacgggcca    420
ggaaggcttc atccccttca attttgtggc caaagcgaac agcctggagc ccgaaccctg    480
gttcttcaag aacctgagcc gcaaggacgc ggagcggcag ctcctggcgc ccgggaacac    540
tcacggctcc ttcctcatcc gggagagcga gagcaccgcg ggatcgtttt cactgtcggt    600
ccgggacttc gaccagaacc agggagaggt ggtgaaacat tacaagatcc gtaatctgga    660
caacggtggc ttctacatct cccctcgaat cacttttccc ggcctgcatg aactggtccg    720
ccattacacc aatgcttcag atgggctgtg cacacgttg agccgcccct gccagaccca    780
gaagccccag aagccgtggt gggaggacga gtgggaggtt cccagggaga cgctgaagct    840
ggtggagcgg ctgggggctg gacagttcgg ggaggtgtgg atgggggtact acaacgggca    900 cacgaaggtg gcggtgaaga gcctgaagca gggcagcatg tccccggacg ccttcctggc    960
cgaggccaac ctcatgaagc agctgcaaca ccagcggctg gttcggctct acgctgtggt   1020
cacccaggag cccatctaca tcatcactga atacatggag aatgacacac ttctagactc    1080
ccagttggag gagaaaggtc tgggggcctc cccctgggc aacttgggcc agcaactctt    1140
gcttctgccc acagggagtc tagtggattt tctcaagacc ccttcaggca tcaagttgac   1200
catcaacaaa ctcctggaca tggcagccca aattgcagaa ggcatggcat tcattgaaga    1260
```

| | |
|---|---:|
| gcggaattat attcatcgtg accttcgggc tgccaacatt ctggtgtctg acaccctgag | 1320 |
| ctgcaagatt gcagactttg cctagcacg cctcattgag gacaacgagt acacagccag | 1380 |
| ggagggggcc aagtttccca ttaagtggac agcgccagaa gccattaact acgggacatt | 1440 |
| caccatcaag tcagatgtgt ggtcttttgg gatcctgctg acggaaattg tcacccacgg | 1500 |
| ccgcatccct tacccaggga tgaccaaccc ggaggtgatt cagaacctgg agcgaggcta | 1560 |
| ccgcatggtg cgccctgaca actgtccaga ggagctgtac caactcatga ggctgtgctg | 1620 |
| gaaggagcgc ccagaggacc ggcccacctt tgactacctg cgcagtgtgc tggaggactt | 1680 |
| cttcacggcc acagagggcc agtaccagcc tcagccttga gaggccttga gaggccctgg | 1740 |
| ggttctcccc ctttctctcc agcctgactt ggggagatgg agttcttgtg ccatagtcac | 1800 |
| atggcctatg cacatatgga ctctgcacat gaatcccacc cacatgtgac acatatgcac | 1860 |
| cttgtgtctg tacacgtgtc ctgtagttgc gtggactctg cacatgtctt gtacatgtgt | 1920 |
| agcctgtgca tgtatgtctt ggacactgta caaggtaccc cttctggct ctcccatttc | 1980 |
| ctgagaccac agagagaggg gagaagcctg ggattgacag aagcttctgc ccacctactt | 2040 |
| ttcttcctc agatcatcca gaagttcctc aagggccagg actttatcta atacctctgt | 2100 |
| gtgctcctcc ttggtgcctg gcctggcaca catcaggagt tcaataaatg tctgttgatg | 2160 |
| actgtt | 2166 |

<210> SEQ ID NO 26
<211> LENGTH: 2116
<212> TYPE: DNA
<213> ORGANISM: human

<400> SEQUENCE: 26

| | |
|---|---:|
| aagtcagggt gggacgtggg cgcggggaga caggtggtgg ctacgacggc gaagggagct | 60 |
| gagactgtcc aggcagccag gttaggccag gaggaccatg tgaatggggc cagagggctc | 120 |
| ccgggctggg cagggaccat gggctgtggc tgcagctcac acccggaaga tgactggatg | 180 |
| gaaaacatcg atgtgtgtga gaactgccat tatcccatag tcccactgga tggcaagggc | 240 |
| acgctgctca tccgaaatgg ctctgaggtg cggaccccac tggttaccta cgaaggctcc | 300 |
| aatccgccgg cttccccact gcaagacaac ctggttatcg ctctgcacag ctatgagccc | 360 |
| tctcacgacg gagatctggg cttttgagaag ggggaacagc tccgcatcct ggagcagagc | 420 |
| ggcgagtggt ggaaggcgca gtccctgacc acgggccagg aaggcttcat ccccttcaat | 480 |
| tttgtggcca aagcgaacag cctggagccc gaaccctggt tcttcaagaa cctgagccgc | 540 |
| aaggacgcgg agcggcagct cctggcgccc gggaacactc acggctcctt cctcatccgg | 600 |
| gagagcgaga gcaccgcggg atcgttttca ctgtcggtcc gggacttcga ccagaaccag | 660 |
| ggagaggtgg tgaaacatta caagatccgt aatctggaca acggtggctt ctacatctcc | 720 |
| cctcgaatca cttttccccgg cctgcatgaa ctggtccgcc attacaccaa tgcttcagat | 780 |
| gggctgtgca cacggttgag ccgcccctgc cagacccaga agcccagaa gccgtggtgg | 840 |
| gaggacgagt gggaggttcc cagggagacg ctgaagctgg tggagcggct gggggctgga | 900 |
| cagttcgggg aggtgtggat ggggtactac aacgggcaca cgaaggtggc ggtgaagagc | 960 |
| ctgaagcagg gcagcatgtc cccggacgcc ttcctggccg aggccaacct catgaagcag | 1020 |
| ctgcaacacc agcggctggt tcggctctac gctgtggtca cccaggagcc catctacatc | 1080 |
| atcactgaat acatggagaa tgggagtcta gtggattttc tcaagacccc ttcaggcatc | 1140 |
| aagttgacca tcaacaaact cctggacatg gcagcccaaa ttgcagaagg catggcattc | 1200 |

```
attgaagagc ggaattatat tcatcgtgac cttcgggctg ccaacattct ggtgtctgac    1260
accctgagct gcaagattgc agactttggc ctagcacgcc tcattgagga caacgagtac    1320
acagccaggg aggggccaa gtttcccatt aagtggacag cgccagaagc cattaactac     1380
gggacattca ccatcaagtc agatgtgtgg tcttttggga tcctgctgac ggaaattgtc    1440
acccacggcc gcatccctta cccagggatg accaacccgg aggtgattca gaacctggag    1500
cgaggctacc gcatggtgcg ccctgacaac tgtccagagg agctgtacca actcatgagg    1560
ctgtgctgga aggagcgccc agaggaccgg cccacctttg actacctgcg cagtgtgctg    1620
gaggacttct tcacgccac agagggccag taccagcctc agccttgaga ggccttgaga     1680
ggccctgggg ttctcccct ttctctccag cctgacttgg ggagatggag ttcttgtgcc     1740
atagtcacat ggcctatgca catatggact ctgcacatga atcccaccca catgtgacac    1800
atatgcacct tgtgtctgta cacgtgtcct gtagttgcgt ggactctgca catgtcttgt    1860
acatgtgtag cctgtgcatg tatgtcttgg acactgtaca aggtacccct ttctggctct    1920
cccatttcct gagaccacag agagggga gaagcctggg attgacagaa gcttctgccc      1980 acctacttttt ctttcctcag atcatccaga agttcctcaa gggccaggac tttatctaat   2040
acctctgtgt gctcctcctt ggtgcctggc ctggcacaca tcaggagttc aataaatgtc    2100
tgttgatgac tgttgt                                                    2116

<210> SEQ ID NO 27
<211> LENGTH: 2064
<212> TYPE: DNA
<213> ORGANISM: human

<400> SEQUENCE: 27
gggagctgag actgtccagg cagccaggtt aggccaggag gaccatgtga atggggccag       60
agggctcccg ggctgggcag ggaccatggg ctgtggctgc agctcacacc cggaagatga      120
ctggatggaa acatcgatg tgtgtgagaa ctgccattat cccatagtcc cactggatgg       180
caagggcacg ctgctcatcc gaaatggctc tgaggtgcgg gacccactgg ttacctacga      240
aggctccaat ccgccggctt ccccactgca agacaacctg gttatcgctc tgcacagcta      300
tgagccctct cacgacggag atctgggctt tgagaagggg gaacagctcc gcatcctgga      360
gcagagcggc gagtggtgga aggcgcagtc cctgaccacg ggccaggaag gcttcatccc      420 cttcaattt gtggccaaag cgaacagcct ggagcccgaa ccctggttct tcaagaacct      480
gagccgcaag gacgcggagc ggcagctcct ggcgcccggg aacactcacg gctccttcct     540
catccgggag agcgagagca ccgcgggatc gttttcactg tcggtccggg acttcgacca     600
gaaccaggga gaggtggtga acattacaa gatccgtaat ctggacaacg gtggcttcta     660
catctcccct cgaatcactt tcccggcct gcatgaactg gtccgccatt acaccaatgc     720
ttcagatggg ctgtgcacac ggttgagccg ccctgccag acccagaagc cccagaagcc     780
gtggtgggag gacgagtggg aggttcccag ggagacgctg aagctggtgg agcggctggg     840
ggctggacag ttcgggggagg tgtggatggg gtactacaac gggcacacga aggtggcggt    900
gaagagcctg aagcagggca gcatgtcccc ggacgccttc ctggccgagg ccaacctcat    960
gaagcagctg caacaccagc ggctggttcg gctctacgct gtggtcaccc aggagcccat  1020
ctacatcatc actgaataca tggagaatgg gagtctagtg gatttttctca agaccccttc  1080 aggcatcaag ttgaccatca acaaactcct ggacatggca gcccaaattg cagaaggcat  1140
```

```
ggcattcatt gaagagcgga attatattca tcgtgacctt cgggctgcca acattctggt    1200
gtctgacacc ctgagctgca agattgcaga ctttggccta gcacgcctca ttgaggacaa    1260
cgagtacaca gccagggagg gggccaagtt tcccattaag tggacagcgc cagaagccat    1320
taactacggg acattcacca tcaagtcaga tgtgtggtct tttgggatcc tgctgacgga    1380
aattgtcacc cacggccgca tcccttaccc agggatgacc aacccggagg tgattcagaa    1440
cctggagcga ggctaccgca tggtgcgccc tgacaactgt ccagaggagc tgtaccaact    1500
catgaggctg tgctggaagg agcgcccaga ggaccggccc acctttgact acctgcgcag    1560
tgtgctggag gacttcttca cggccacaga gggccagtac cagcctcagc cttgagaggc    1620
cttgagaggc cctgggggttc tcccccttttc tctccagcct gacttgggga gatggagttc    1680
ttgtgccata gtcacatggc ctatgcacat atggactctg cacatgaatc ccacccacat    1740
gtgacacata tgcaccttgt gtctgtacac gtgtcctgta gttgcgtgga ctctgcacat    1800
gtcttgtaca tgtgtagcct gtgcatgtat gtcttggaca ctgtacaagg tacccctttc    1860
tggctctccc atttcctgag accacagaga gaggggagaa gcctgggatt gacagaagct    1920
tctgcccacc tacttttctt tcctcagatc atccagaagt tcctcaaggg ccaggacttt    1980
atctaatacc tctgtgtgct cctccttggt gcctggcctg gcacacatca ggagttcaat    2040
aaatgtctgt tgatgactgt tgta                                           2064

<210> SEQ ID NO 28
<211> LENGTH: 2189
<212> TYPE: DNA
<213> ORGANISM: human

<400> SEQUENCE: 28
gtgtgaattt acttgtagcc tgagggctca gagggagcac cggtttggag ctgggacccc      60
ctattttagc ttttctgtgg ctggtgaatg gggatcccag gatctcacaa tctcagggac     120
catgggctgt ggctgcagct cacacccgga agatgactgg atggaaaaca tcgatgtgtg     180
tgagaactgc cattatccca tagtcccact ggatggcaag ggcacgctgc tcatccgaaa     240
tggctctgag gtgcgggacc cactggttac ctacgaaggc tccaatccgc cggcttcccc     300
actgcaagac aacctggtta tcgctctgca cagctatgag ccctctcacg acggagatct     360
gggctttgag aagggggaac agctccgcat cctggagcag agcggcgagt ggtgaaggc     420 gcagtccctg accacgggcc aggaaggctt catcccttc aattttgtgg ccaaagcgaa     480
cagcctggag cccgaaccct ggttcttcaa gaacctgagc cgcaaggacg cggagcggca     540
gctcctggcg cccgggaaca ctcacggctc cttcctcatc cgggagagcg agagcaccgc     600
gggatcgttt tcactgtcgg tccgggactt cgaccagaac cagggagagg tggtgaaaca     660
ttacaagatc cgtaatctgg acaacggtgg cttctacatc tcccctcgaa tcactttttcc     720 cggcctgcat gaactggtcc gccattacac caatgcttca gatgggctgt gcacacggtt     780
gagccgcccc tgccagaccc agaagcccca gaagccgtgg tgggaggacg agtgggaggt     840
tcccagggag acgctgaagc tggtggagcg gctgggggct ggacagttcg ggaggtgtg     900 gatggggtac tacaacggg cacgaaggt ggcggtgaag agcctgaagc agggcagcat    960
gtccccggac gccttcctgg ccgaggccaa cctcatgaag cagctgcaac accagcggct    1020
ggttcggctc tacgctgtgg tcacccagga gccatctac atcatcactg aatacatgga    1080
gaatgacaca cttctagact cccagttgga ggagaaggt ctgggggcct cccctgggg     1140 caacttgggc cagcaactct tgcttctgcc cacagggagt ctagtggatt ttctcaagac    1200
```

-continued

```
cccttcaggc atcaagttga ccatcaacaa actcctggac atggcagccc aaattgcaga    1260
aggcatggca ttcattgaag agcggaatta tattcatcgt gaccttcggg ctgccaacat    1320
tctggtgtct gacaccctga gctgcaagat tgcagacttt ggcctagcac gcctcattga    1380
ggacaacgag tacacagcca gggaggggc caagtttccc attaagtgga cagcgccaga    1440
agccattaac tacgggacat tcaccatcaa gtcagatgtg tggtcttttg ggatcctgct    1500
gacggaaatt gtcacccacg gccgcatccc ttacccaggg atgaccaacc ggaggtgat    1560 tcagaacctg gagcgaggct accgcatggt gcgccctgac aactgtccag aggagctgta    1620
ccaactcatg aggctgtgct ggaaggagcg cccagaggac cggcccacct ttgactacct    1680
gcgcagtgtg ctggaggact tcttcacggc cacagagggc cagtaccagc tcagccttg    1740 agaggccttg agaggccctg ggttctcccc cttctctc cagcctgact ggggagatg     1800 gagttcttgt gccatagtca catggcctat gcacatatgg actctgcaca tgaatcccac    1860
ccacatgtga cacatatgca ccttgtgtct gtacacgtgt cctgtagttg cgtggactct    1920
gcacatgtct tgtacatgtg tagcctgtgc atgtatgtct tggacactgt acaaggtacc    1980
cctttctggc tctcccattt cctgagacca cagagagagg ggagaagcct gggattgaca    2040
gaagcttctg cccacctact tttctttcct cagatcatcc agaagttcct caagggccag    2100
gactttatct aataccctg tgtgctcctc cttggtgcct ggcctggcac acatcaggag    2160
ttcaataaat gtctgttgat gactgttgt                                      2189

<210> SEQ ID NO 29
<211> LENGTH: 2120
<212> TYPE: DNA
<213> ORGANISM: human

<400> SEQUENCE: 29
gtgtgaattt acttgtagcc tgagggctca gagggagcac cggtttggag ctggaccc       60 ctattttagc ttttctgtgg ctggtgaatg gggatcccag gatctcacaa tctcagggac    120
catgggctgt ggctgcagct cacacccgga agatgactgg atggaaaaca tcgatgtgtg    180
tgagaactgc cattatccca tagtcccact ggatggcaag ggcacgctgc tcatccgaaa    240
tggctctgag gtgcgggacc cactggttac ctacgaaggc tccaatccgc cggcttcccc    300
actgcaaggt gaccccaggc agcagggcct gaaagacaag gctgcggat ccctggctgt    360 tggcttccac ctctccccca cctactttct ccccggtctt gccttccttg tccccccaccc   420 tgtaactcca ggcttcctgc cgatcccagc tcggttctcc ctgatgcccc ttgtctttac    480
agacaacctg gttatcgctc tgcacagcta tgagccctct cacgacggag atctgggctt    540
tgagaagggg aacagctcc gcatcctgga gcagagcggc gagtggtgga aggcgcagtc    600
cctgaccacg ggccaggaag gcttcatccc cttcaatttt gtggccaaag cgaacagcct    660
ggagcccgaa ccctggttct tcaagaacct gagccgcaag gacgcggagc ggcagctcct    720
ggcgcccggg aacactcacg gctccttcct catccgggag agcgagagca ccgcgggatc    780
gttttcactg tcggtccggg acttcgacca gaaccaggga gaggtggtga acattacaa     840 gatccgtaat ctggacaacg gtggcttcta catctcccct cgaatcactt ttcccggcct    900
gcatgaactg gtccgccatt acaccaggta ctacaacggg cacacgaagg tggcggtgaa    960
gagcctgaag cagggcagca gtccccgga cgccttcctg gccgaggcca acctcatgaa    1020
gcagctgcaa caccagcggc tggttcggct ctacgctgtg gtcacccagg agcccatcta   1080
```

| | |
|---|---|
| catcatcact gaatacatgg agaatgggag tctagtggat tttctcaaga cccccttcagg | 1140 |
| catcaagttg accatcaaca aactcctgga catggcagcc caaattgcag aaggcatggc | 1200 |
| attcattgaa gagcggaatt atattcatcg tgaccttcgg gctgccaaca ttctggtgtc | 1260 |
| tgacaccctg agctgcaaga ttgcagactt tggcctagca cgcctcattg aggacaacga | 1320 |
| gtacacagcc agggaggggg ccaagtttcc cattaagtgg acagcgccag aagccattaa | 1380 |
| ctacgggaca ttcaccatca agtcagatgt gtggtctttt gggatcctgc tgacggaaat | 1440 |
| tgtcacccac ggccgcatcc cttacccagg gatgaccaac ccggaggtga ttcagaacct | 1500 |
| ggagcgaggc taccgcatgg tgcgccctga caactgtcca gaggagctgt accaactcat | 1560 |
| gaggctgtgc tggaaggagc gcccagagga ccggcccacc tttgactacc tgcgcagtgt | 1620 |
| gctggaggac ttcttcacgg ccacagaggg ccagtaccag cctcagcctt gagaggcctt | 1680 |
| gagaggccct ggggttctcc ccctttctct ccagcctgac ttggggagat ggagttcttg | 1740 |
| tgccatagtc acatggccta tgcacatatg gactctgcac atgaatccca cccacatgtg | 1800 |
| acacatatgc accttgtgtc tgtacacgtg tcctgtagtt gcgtggactc tgcacatgtc | 1860 |
| ttgtacatgt gtagcctgtg catgtatgtc ttggacactg tacaaggtac cccttttctgg | 1920 |
| ctctcccatt tcctgagacc acagagagag gggagaagcc tgggattgac agaagcttct | 1980 |
| gcccacctac ttttctttcc tcagatcatc cagaagttcc tcaagggcca ggactttatc | 2040 |
| taatacctct gtgtgctcct ccttggtgcc tggcctggca cacatcagga gttcaataaa | 2100 |
| tgtctgttga tgactgttgt | 2120 |

<210> SEQ ID NO 30
<211> LENGTH: 2099
<212> TYPE: DNA
<213> ORGANISM: human

<400> SEQUENCE: 30

| | |
|---|---|
| gtgtgaattt acttgtagcc tgagggctca gagggagcac cggtttggag ctgggacccc | 60 |
| ctattttagc ttttctgtgg ctggtgaatg gggatcccag gatctcacaa tctcagggac | 120 |
| catgggctgt ggctgcagct cacacccgga agatgactgg atggaaaaca tcgatgtgtg | 180 |
| tgagaactgc cattatccca tagtcccact ggatggcaag ggcacgctgc tcatccgaaa | 240 |
| tggctctgag gtgcgggacc cactggttac ctacgaaggc tccaatccgc cggcttcccc | 300 |
| actgcaagac aacctggtta cgctctgca cagctatgag ccctctcacg acggagatct | 360 |
| gggctttgag aaggggaac agctccgcat cctggagcag agcggcgagt ggtgaaggc | 420 |
| gcagtccctg accacgggcc aggaaggctt catccccttc aattttgtgg ccaaagcgaa | 480 |
| cagcctggag cccgaaccct ggttcttcaa gaacctgagc cgcaaggacg cggagcggca | 540 |
| gctcctggcg cccgggaaca ctcacggctc cttcctcatc cgggagagcg agagcaccgc | 600 |
| gggatcgttt tcactgtcgg tccgggactt cgaccagaac cagggagagg tggtgaaaca | 660 |
| ttacaagatc cgtaatctgg acaacggtgg cttctacatc tcccctcgaa tcactttttcc | 720 |
| cggcctgcat gaactggtcc gccattacac caatgcttca gatgggctgt gcacacggtt | 780 |
| gagccgcccc tgccagaccc agaagcccca gaagccgtgg tgggaggacg agtgggaggt | 840 |
| tcccagggag acgctgaagc tggtggagcg gctgggggct ggacagttcg ggaggtgtg | 900 |
| gatggggtac tacaacgggc acacgaaggt ggcggtgaag agcctgaagc agggcagcat | 960 |
| gtccccggac gccttcctgg ccgaggccaa cctcatgaag cagctgcaac accagcggct | 1020 |
| ggttcggctc tacgctgtgg tcacccagga gcccatctac atcatcactg aatacatgga | 1080 |

```
gaatgggagt ctagtggatt ttctcaagac cccttcaggc atcaagttga ccatcaacaa    1140
actcctggac atggcagccc aaattgcaga aggcatggca ttcattgaag agcggaatta    1200
tattcatcgt gaccttcggg ctgccaacat tctggtgtct gacaccctga gctgcaagat    1260
tgcagacttt ggcctagcac gcctcattga ggacaacgag tacacagcca ggaggggggc    1320
caagtttccc attaagtgga cagcgccaga agccattaac tacgggacat tcaccatcaa    1380
gtcagatgtg tggtcttttg ggatcctgct gacggaaatt gtcacccacg ccgcatccc    1440 ttacccaggg atgaccaacc cggaggtgat tcagaacctg gagcgaggct accgcatggt    1500
gcgccctgac aactgtccag aggagctgta ccaactcatg aggctgtgct ggaaggagcg    1560
cccagaggac cggcccacct ttgactacct gcgcagtgtg ctggaggact cttcacggc    1620 cacagagggc cagtaccagc ctcagccttg agaggcttg agaggccctg gggttctccc    1680
cctttctctc cagcctgact tggggagatg gagttcttgt gccatagtca catggcctat    1740
gcacatatgg actctgcaca tgaatcccac ccacatgtga cacatatgca ccttgtgtct    1800
gtacacgtgt cctgtagttg cgtggactct gcacatgtct tgtacatgtg tagcctgtgc    1860
atgtatgtct tggacactgt acaaggtacc cctttctggc tctcccattt cctgagacca    1920
cagagagagg ggagaagcct gggattgaca gaagcttctg cccacctact tttctttcct    1980
cagatcatcc agaagttcct caagggccag gactttatct aatacctctg tgtgctcctc    2040
cttggtgcct ggcctggcac acatcaggag ttcaataaat gtctgttgat gactgttgt    2099

<210> SEQ ID NO 31
<211> LENGTH: 641
<212> TYPE: DNA
<213> ORGANISM: human

<400> SEQUENCE: 31
ggagccgtcc ggcgcagcag tttctaggtc cccactgtcc ccgccgtccc gcccttcgc      60 gtcccgggaa ccggctggct tccgagccgc actcgccgat cctccaggca tgccccgcta    120
cgagctggct ttaatcctga aagccatgca gcggccagag actgctgcta ctttgaaacg    180
tacgatagag gccctgatgg acagaggagc aatagtgagg gacttggaaa acctgggtga    240
acgagcgctt ccttatagga tctctgccca cagtcagcag cacaacagag gcggttgcaa    300
gtggatggca agcttccttg tgacttctca tcctggcaat tttctggagt gtttgtgact    360
ggactttaac atttccaaaa tgtggcgaca gtgactgtta agtcttccca aagacgaggg    420
ttcctgggag cccagggct gcaagcatca ggacagcaga gaccaaattc atcattgaat    480
cctcaacatc tagcacaata tgcctggcat aagatatatc aaggtgtaca gactatattt    540
ttgctgattt ataattcaac tgcattgtag taatggaacc cagtctacat aaagctgata    600
tttaaaaatt tggttggact tcttttgtga cccagcacat g                         641

<210> SEQ ID NO 32
<211> LENGTH: 370
<212> TYPE: DNA
<213> ORGANISM: human

<400> SEQUENCE: 32
catgccccgc tataagctgg ctttaatcct gaaagccatg ccgcggccag actgctgctg      60 cttttgaaaca tacgatagag gttctgatgg aaaaaggagc aatagtgagg aacttggaaa    120
acctgggtga gtgagcgctt ccttgtaaga tctccaccca caatcagtgg cacaacagag    180
```

| gcgggtattt | cctggtgaat | ttttatgcac | caaccacaac | tgttgaaagc | atgatggagc | 240 |
| acttctccaa | acgtagatgt | gattagaccg | aatattgtca | aacaccctct | gacccaggaa | 300 |
| ctaaaagaat | gtgaagggat | tgtcccaatc | ccacttaaag | gaaaattata | ttacacaaag | 360 |
| aagaggaaga | | | | | | 370 |

<210> SEQ ID NO 33
<211> LENGTH: 990
<212> TYPE: DNA
<213> ORGANISM: human

<400> SEQUENCE: 33

| cggcgtctgc | gcagctgcca | gcgcctttaa | gcccgggctc | gcgctctcgg | accgtgcttt | 60 |
| cgccgcctgg | gagccgtccg | gcgcagcagt | ttctaggtcc | ccactgtccc | cgccgtcccg | 120 |
| cccccttcgcg | tcccgggaac | cggctggctt | ccgagccgca | ctcgccgatc | ctccaggcat | 180 |
| gccccgctac | gagctggctt | taatcctgaa | agccatgcag | cggccagaga | ctgctgctac | 240 |
| tttgaaacgt | acgatagagg | ccctgatgga | cagaggagca | atagtgaggg | acttggaaaa | 300 |
| cctgggtgaa | cgagcgcttc | cttataggat | ctctgcccac | agtcagcagc | acaacagagg | 360 |
| cgggtatttc | ttggtggatt | tttatgcacc | caccgcagct | gttgaaagca | tggtggagca | 420 |
| cttgtctcga | gatatagatg | tgattagagg | gaatattgtc | aaacaccctc | tgacccagga | 480 |
| actaaaagaa | tgtgaaggga | ttgtcccagt | cccactcgca | gaaaaattat | attccacaaa | 540 |
| gaagaggaag | aagtgagaag | attcgccaga | ttttagcctt | atatgtaatt | ccttcacatt | 600 |
| tgggcagcat | ggacgagaag | gaagaatttg | caagtttggc | ctttatataa | gcatgtgttg | 660 |
| caggtgctgt | ttgattttc | taaggtattt | ttagcccttg | atccccttg | cttgcgagag | 720 |
| gtggggaact | gctcactgac | agcttctctg | taacctgcag | taccagtgga | tcgttcttga | 780 |
| ttttgttttc | attagtgtca | tttctttgtc | attgaggact | ttccccctta | caacagtaac | 840 |
| accatttttt | gaagagcaaa | acttataata | cctcctggga | ttgtgagcta | gtcattcagc | 900 |
| ctgtgtaacc | atgtggaaat | aaaaattgac | gaccaatgta | ttatatggac | aacttttgct | 960 |
| ttgagtaata | aacttgattg | taggaatgtg | | | | 990 |

<210> SEQ ID NO 34
<211> LENGTH: 7053
<212> TYPE: DNA
<213> ORGANISM: human

<400> SEQUENCE: 34

| gcgagctgag | ctgacagcgc | ggagctggcg | ctgtggagcg | cagggagcct | tgccggttcc | 60 |
| tccgaccggc | gtctgcgagt | acagcggcgg | ctaacctgcc | ccggcttcag | gatttacaca | 120 |
| gacgtggggc | gatgcttgtg | accctgcagc | tcctcaaagg | cccctagaag | cctgtttctc | 180 |
| cgtacagtcc | aggacctcca | gccccatgga | gcccccgatc | ccacagagcg | ccccccttgac | 240 |
| tcccaactca | gtcatggtcc | agccccttct | tgacagccgg | atgtcccaca | gccggctcca | 300 |
| gcacccactc | accatcctac | ccattgacca | ggtgaagacc | agccatgtgg | agaatgacta | 360 |
| catagacaac | cctagcctgg | ccctgaccac | cggcccaaag | cggacccggg | gcggggcccc | 420 |
| agagctggcc | ccgacgcccg | cccgctgtga | ccaggatgtc | acccaccatt | ggatctcctt | 480 |
| cagcggcgc | ccctgctctg | ctacctgcct | gccaccggct | gcgtgaagct | ggcccagcgt | 540 |
| ggctacgacc | gtctgcgccg | ccctggttgc | cgctgcaagc | acacgaacag | cgtcatctgc | 600 |
| aaagcagcca | gcggggatgc | caagaccagc | aggcccgaca | agcctttctg | acagtttgtg | 660 |

```
tcgaagcccc agtgctctgc ctggaaacct ggttctcttc tgacatctaa gaagactgca    720
gcaaggtcag aggttttagc ctcctgaggc tgaccttgct agtctgccca ctccctaccc    780
ccagcttcgg aaaatacaga gaccaccacc acgtaccctg tattcccaa ggtgatgaag     840 aagcactttg gggcttttt tcagggtcct gaaactttgt gtcaaacaga caatgcaggg     900
gcagggtgtg gtttggggg aaattttct ttttcagaag acagaacaca gatgtggaca      960
catatccgga aactgcagct gcttgaatgc cttcccagcc cctccttctc cctccctccc   1020 tccgccccc ccttcctctt ttccattgtc tttggctctc acaggagcta gctgcctggg    1080
aggaattgtt aactgagtac cagggtacct ttaaagaaga cccttggagt cttctatacc   1140
ttcttctcct tccccatctc actccacccc actttgtccc tgatgtcttg gggaaggtgt   1200
agaacaccct agcagttcct attgtatata cttgggagcc actgagaaca gaggacggcc   1260
agtgagtcca agcctcgttc ctccttctgc ctccccggag ccacaggatg gatttaggag   1320
ccactgctca gtgcacttct cccttccaac tgcatcaact aactctcggg ggtgttctgc   1380
tcaccacacc gtccttcggt tcttactgag tcacagactc gcctgcccac tacgtgtcct   1440
gggttctcta ctcagatccc ttccagaaac tttatatggg tagaggaagc cagggcggca   1500
aatgcgagac caaatatcat tttgccaatg agtctgaggc tgtggtctct ggatccagtc   1560
attatgtttt tatagaataa ttaaaccgga tgctaacggt gttttaaaaa ataataataa   1620
aacaacttgt ttccttttgg ccaccccag gaagggctga tttcaaaatc tggggggcgag   1680 caacctcaag gaacacaatt tccctcccta tcaacaagag gatttaaaca gcaaagaaga   1740
gaggcagcac ctcccattgg cagaatgacc gctgagccag gctgggtttg ggtttcttct   1800
cttctgattc tgctgctcac tgtcatagcc ttttgtgtat agtgatgtgt ctgtatcttt   1860
aatgtaaata gagagatgat gaaaaagag tctatttag tgttaggaag ccccagcagg    1920
ggagtcggaa gagcttggaa gagctgggga gagggtaggg gaaaggtttt tccaggggcc   1980
actgggtttg agccctgctt ctgtgcacag ccacaccacc ctctcccgac agccctcaaa   2040
gacgtagcaa ctctttctct caaggtgcta aaggactcag aaggtgcagc acgtccagtg   2100
ggtaggtact tgttgcatgc aaaagctgta gtgtatctgg tccttcctcc ccagcttttg   2160
tgtggggttc ttgctttgtg tggtattttg ttttcccctc taatgagagg gcatggcctg   2220
agtcagaaga gctaccccag gtgaaactgg aagtgcatga ggcagagcgt ccgtagcatt   2280
tccagtttgt tctgtatagg acagaggtgc ctccgggaag gaggcagcga ggtaggtagc   2340
tatgataggc acctaatgct tctcaaggac ttattttttc cttcttgaag actagtagta   2400
acatcttatg atttagagta agttgattgt aaccataggt atttattgat tggaggaagg   2460
gagggtcata ttattttcgg ctttatttat gtaacatttg ctagcttata aaaggcgaat   2520
gtgaaatatt gcatctgcat tttccaaggc tgattcgtgt agctaccctt gccacagttg   2580
tgacggatgt atggatgttc ttgaacattt cagaaggagt ggtagaaaaa acacacatt    2640 cagccaacca cttatatgaa ttgaatgtat cagaagtgta ctgaagggac tggagatggt   2700
tttcctcaga tgagggggcc ccaaaattga tagtgcacat ctgcacgctt tctgcgaggc   2760
ctcagaactt ttcccagggc ccctccctca aattgtctcc atgggaaact tgacccagtg   2820
gcaagttgca ctttggtgat cttggtggtc tacacaccg ttctgtggag agtcgattta    2880
cataagctgt gtatacacac acacacacac acacacacac acacacacac acaccctac    2940 cccacactga ctgtctaccg acagagaccc tatttcctgg caaacggcct cctgaaccct   3000
```

```
gacttttttgt gtacatactt gtaaacacgg attttttctgg gttttggttt gctttttcct   3060
tttttccccc tgccctgtt ctagcttgtt cttcttggtt tgctttcaac ctgcttgatg   3120
gatgtctgca gagtgctctc taagagtcca cctcagtgcc tcgtgtgctc agtggtcatg   3180
ggaaggagcg aaggaaccat ccttggttct cccagcttgg ttgtgtagca atccctcagc   3240
attgttttc tcagcttctt ggcaaaaatt aaaacaacaa caacaacaac aacaacaaca   3300
acaaacagaa ggataaactg gcttgcctgt ggaccctccc cggctctggg gccagtcgag   3360
agccactgag ggacccagca ctcagagaca caacacacat gtgtagctgc ttctggctga   3420
gtgtgtttcc tgtcaccaat ggcctgtttg gctggacgat gcctcggctt gacctttttt   3480
gaaaagtgct ggttagttcc cgccccctgg taaacctggg gtaggtgggg gttctgtctt   3540
aactcgaggg gcacctggga tccaggacgc ttctagggggg ctctggctgc ccgtgttaat   3600
gaaggacagc gcttccgcga gcaccctggg aactgggtct tgggtagcaa agccctccca   3660
gagaaaagat gggcacaact aaggcttttcc tgagcaggaa gggggtgaag accaatccct   3720
tcctttggtc ctttggtacg cacccccctca gagctgagat ggaagacatg gctagttctt   3780
ttcagccttg tggagcctgt cagtcgccat catacctcga gtgaggccca gctagataat   3840
gacttgtcca agatggcaca cgtggaaagt tgatctgcac cagaacccgg atgactgtca   3900
ccttgaagcg tcctgttctc cttctgtgct gtcccaggaa gtgtctggcg ggcgtgggca   3960
gcacagctct acactgtacg attcactagg gcatcctgcg agcctcacta gccttctggt   4020
tcatgccttt gacaagcatt tttgtgcccc ctctgcttac tgtgacagtc gatgatgaat   4080
cttgcgttgc cattttctgc tgtgggtaac tgcgtgcagt gtcttgcctt gctttctctt   4140
cttactgtcc cacagcttgg tttcatgtta caaacagaaa agctcgaggc tcccaccccg   4200
ccacatccca acttcatttc cccctcactg tagcccatt ccaccccacc acaaagttgc   4260
cacaggtttt ctttgtatag aatatttatt ttgaagctct atttttaatag tatttatttt   4320
agaaagtcta ctattgtaag agttcttctg tttgtgaaga aaaaaacaag ttaaaaactg   4380
aatgtactga tttagaaaat atatataaat atatattgtt aaatatactt tgattgcgcc   4440
actgcactcc agccttggcg accagactaa gacgctgtct caaaaaaaaa caaaaacgac   4500
aaaaaaaaaa caaaacagaa aaaataaact aaggcaatga cagtccctgg caaatgctgg   4560
gagggaggca gcagtggtca gggaaggtaa ccctgaagca ggacttgtaa agcaaataag   4620
attgggaggc caaggtgggt ggatcacgag gtcaggagtt cgagaccagc ctggccaaca   4680
tagtgaaacc ccgtctttac taaaaataca aaaaaattag ccaggtgtgg tggtgggtgc   4740
ctgtagtccc agctacttgg gaggctgagg caggagaatc tcgaacccag gaggcggagg   4800
ttacagtcag ctgagaccgc accattgcac tccagcctgg gtgacagagc aagattccgt   4860
ctcaaaaaaa aaaaaaaaa aaaaaccaa gaagaaaagg aatgaattag aacttcttct   4920
gcttggactt aagggcatca tcaggcaggt tttgggtagg atagcagggg aggcagagac   4980
atagtcgggg tcagtggtca tgagtgtggc tttgagccca aaaacttggt ttctgttccc   5040
tactttgcca ctcagtagtg catgactttg gccaaatttc ttaaattcat gaagcaagtt   5100
tccgggtgaa tgaaatgggg ataaaaatag tgttcaaacc tatccgttgg tttgtgtgaa   5160
actgaaatga atagtatcgt gcaggtactt gtgagcaagg ggagctgctg tttcctgtcc   5220
ctttatgatg ggaaatatct agacaagttc ccaaccctct gcactgcagg ctgcatggca   5280
cggagggtct tgtaacacag ctggggctgg ccttctttta ggagcttcag tggttctgaa   5340
aacttttatt tgtttgtttg ttttagtaga tgtggggtct ttctgtgttg tccggactgg   5400
```

```
tctcaaactt ctggactcaa gtgatcctcc cccgctcaac ctcccaaagt gttgggatta    5460
caggtgtgag ccactgtgcc cagccttgaa aacttttttca ggttcttcca gggttactgg   5520
gcaattaaat atttctattt cattataagt cagtttttca aagttatatt atcttaatta    5580
ccttttttat atgtattagt gtagagtagc attttatatt ttgatatcct ccttatgcat    5640 agttttttcac ttttttattcc tagttttttcg ttttttaataa gactttcaag aaatttattt 5700
tattggcctt ttgaaaaaag cagctttaga taaagtaagc agttctgctt tcattttata    5760
atttatttct acttttgttt cattaatctt ttcctccggc atgccttgga ttttgttgtg    5820 ttactcttttt tctagaggct cgcattgtgt gtctggttca cttatgatca cgcttgccta   5880
cttttaagaa tggaagaggg gaggtggagg gtggctgcac agtcgagggt gtgaggcagt    5940
cttgctctag ccccaccatg ccctcagccc gctgtggcca cgctggttcc tcaattgctg    6000
gggcgtgcag tgtctgtaag ggaggctact gatgccatcc gaggaagatg taaggtttcg    6060
tgtgggcagc gagagcctag caggcatgtg gggtgcccag caaagggtaa cagtggacag    6120
ttgttgcctc attccacaga gttttgattt tttttttttt tttaatggtc actccatcaa    6180
catcccccat ggccagagcc tgagctggtc cccagagaca caggcattca gctgacagcc    6240
tcgccttcac gctgctgctg ttctcatggg ggacaggcct caggtggcaa tgcacaaatc    6300
attagttaag ggcagttgtg acagttacca aggagtgtag cccccgcccg agtgaaaaca    6360
gccctaacca ggggtgggga ccttgggcct ctgacccgaa gggtaggaga agctggaagg    6420
acagcattcc tgtctgcgaa ggcaggagca aagctgccag gctatgaagg aaatggctgg    6480
agcctgaagt catgcaagct ggggctggca gggacagggc caacttccag gcctgggggc    6540
caccatgagg attcaggacg tgaccccccag ggcacatgaa ggccttccat ctgtatttaa    6600
gaaaagactt tatcagacga gtatggtgct cacgcctgta atcttagcac tttgggaggc    6660
tgaggcaggt ggatcacgag gtcaggagtt caagaccagc ctggccaata tggtaaaccc    6720
catctctact aaactacaaa atagccaggc atggtggcgc acgcctgtag tcccagctac    6780
tcgggaggct gaggcagaag aatcacttga acccgggagg tggaggttac agtgagccaa    6840
gatcgcgcca ctacactcca gcctgggtga cagagtgaga ctccgtctca aaaaaaccaa    6900
aagactttat cttatttcct atatgtttgt ggtttcagtc ctgatgtata atttgaccct    6960
agttagaatg gttatctgag gaagtggcct gtacgatttc tgctttttta aatgtgtggc    7020 tcccttttctt cattgattaa cgtatgatta ttt                                7053

<210> SEQ ID NO 35
<211> LENGTH: 3756
<212> TYPE: DNA
<213> ORGANISM: human

<400> SEQUENCE: 35
ggagttagcg acagggaggg atgcgcgcct gggtgtagtt gtggggaggg aagtggctag      60
ctcagggctt caggggacag acagggagag atgactgagt tagatgagac gaggggggcgg   120 gctgggggtg cgagaaggaa gcttggcaag gagactaggt ctaggggac  cacagtgggg     180 caggctgcat ggaaaatatc cgcagggtcc cccaggcaga acagccacgc tccaggccag    240
gctgtcccta ctgcctggtg gaggggggaac ttgacctctg ggagggcgcc gctcttgcat    300
agctgagcga gcccgggtgc gctggtctgt gtggaaggag gaaggcaggg agaggtagaa    360
ggggtggagg agtcaggagg aataggccgc agcagccctg gaaatgatca ggaaggcagg    420
```

```
cagtgggtgc agggctgcag gagggccggg agggctaatc ttcaacttgt ccatgccagc    480 agccccttt tttccagacc aagggctgtg aacccgcctg gggatgaggc ctggtcttgt    540
ggaactgaac ttagctcgac ggggctgacc gctctggccc agggtggtat gtaattttcg    600
ctcggcctgg acggggccc aggccggcc cagcctggtg gagcgtccag gtctgggtgc    660
gaagccaggc ccctgggcgg aggtgagggg tggtctgagg agtgatgtgg agttaaggcg    720
ccatcctcac cggtgactgg tgcggcacct agcatgtttg acaggcgggg actgcgaggc    780
acgctgctcg ggtgttgggg acaacattga ccaacgcttt attttccagg tggcagtgct    840
ccttttggac ttttctctag gtttggcgct aaactcttct tgtgagctca ctccacccct    900
tcttcctccc tttaacttat ccattcactt aaaacattac ctggtcatct ggtaagcccg    960
ggacagtaag ccgagtggct gttggagtcg gtattgttgg taatggtgga ggaagagagg   1020
ccttcccgct gaggctgggg tggggcggat cggtgttgct tgcctgcaga gagggtgggg   1080
agtgaatgtg caccctggg tgggcctgca gccatccagc tgaaagttac aaaaatgctt   1140
catggaccgt ggtttgttac tatagtgttc ctcatggcga gcagatggaa ccggagaca    1200 tggagtccct ggccagtgtg agtcctagca ttgcaggagg ggagaccctg gaggagagag   1260
cccgcctcaa ttgatgcctg cagattgaat ttccagaggc ttaggaggag gaagttctcc   1320
aatgttctgt ttccaggcct tgctcaggaa gccctgtatt caggaggcta ccatttaaag   1380
tttgcagatg agcttatggg gggcaatctt aaaaagtcca cagcagatgc atccggctcg   1440
aggggccatc agctttgaat aaatgcttgt tccagagccc atgaatgcca gcaggcaccc   1500
ctcctttcct ggggtaaagg ttttcagatg ctgcatcttc taaattgagc ctccggtcat   1560
actagttttg tgcttggaac cttgcttcaa gaagatccct aagctgtaga acattttaac   1620
gttgatgcca caacgcagat tgatgccttg tagatggagc ttgcagatgg agccccgtga   1680
cctctcacct acccacctgt ttgcctgcct tcttgtgcgt ttctcggaga agttcttagc   1740
ctgatgaaat aacttgggc gttgaagagc tgtttaattt taaatgcctt agactgggga   1800
tatattagag gaagcagatt gtcaaattaa gggtgtcatt gtgttgtgct aaacgctggg   1860
agggtacaag ttggtcattc ctaaatctgt gtgtgagaaa tggcaggtct agtttgggca   1920
ttgtgattgc attgcagatt actaggagaa gggaatggtg ggtacaccgg tagtgctctt   1980
ttgttcttgc ttcgtttttt taaacttgaa ctttacttcg ttagatttca taatactttc   2040
ttggcattct agtaagagga ccctgaggtg ggagttgtgg gggacgggga aaggggaca   2100 gcttggcacc ggtcccgtgg gcgttgcagt gtggggatg ggggtatgca gcttggcact   2160
ggtactggga gggatgaggg tgaagaaggg gagagggttg gttagagata cagtgtgggt   2220
ggtgggggtg gtaggaaatg caggttgaag ggaattctct ggggctttgg ggaatttagt   2280
gcgtgggtga gccaagaaaa tactaattaa taatagtaag ttgttagtgt tggttaagtt   2340
gttgcttgga agtgagaagt tgcttagaaa ctttccaaag tgcttagaac tttaagtgca   2400
aacagacaaa ctaacaaaca aaaattgttt tgctttgcta caaggtgggg aagactgaag   2460
aagtgttaac tgaaaacagg tgacacagag tcaccagttt tccgagaacc aaagggaggg   2520
gtgtgtgatg ccatctcaca ggcaggggaa atgtctttac cagcttcctc ctggtggcca   2580
agacagcctg tttcagaggg ttgttttgtt tggggtgtgg gtgttatcaa gtgaattagt   2640
cacttgaaag atgggcgtca gacttgcata cgcagcagat cagcatcctt cgctgcccct   2700
tagcaactta ggtggttgat ttgaaactgt gaaggtgtga ttttttcagg agctggaagt   2760
cttagaaaag ccttgtaaat gcctatattg tgggcttta acgtatttaa gggaccactt   2820
```

```
aagacgagat tagatgggct cttctggatt tgttcctcat ttgtcacagg tgtcttgtga    2880
ttgaaaatca tgagcgaagt gaaattgcat tgaatttcaa gggaatttag tatgtaaatc    2940
gtgccttaga aacacatctg ttgtcttttc tgtgtttggt cgatattaat aatggcaaaa    3000
tttttgccta tctagtatct tcaaattgta gtctttgtaa caaccaaata accttttgtg    3060
gtcactgtaa aattaatatt tggtagacag aatccatgta cctttgctaa ggttagaatg    3120
aataatttat tgtattttta atttgaatgt ttgtgctttt taaatgagcc aagactagag    3180
gggaaactat cacctaaaat cagtttggaa acaagacctt aaaagggaa ggggatgggg     3240 attgtgggga gagagtgggc gaggtgcctt tactacatgt gtgatctgaa aaccctgctt    3300
ggttctgagc tgcgtctatt gaattggtaa agtaatacca atggcttttt atcatttcct    3360
tcttcccttt aagtttcact tgaaatttta aaaatcatgg ttattttat cgttgggatc     3420 tttctgtctt ctgggttcca ttttttaaat gtttaaaaat atgttgacat ggtagttcag    3480
ttcttaacca atgactttggg gatgatgcaa acaattactg tcgttgggat ttagagtgta   3540
ttagtcacgc atgtatgggg aagtagtctc gggtatgctg ttgtgaaatt gaaactgtaa   3600
aagtagatgg ttgaaagtac tggtatgttg ctctgtatgg taagaactaa ttctgttacg    3660
tcatgtacat aattactaat cactttttctt cccctttaca gcacaaataa agtttgagtt   3720
ctaaactcat tagaaaaaaa aaaaaaaaaa aaaaaa                              3756

<210> SEQ ID NO 36
<211> LENGTH: 4324
<212> TYPE: DNA
<213> ORGANISM: human

<400> SEQUENCE: 36
ttcctcattg gaagaagaag catagtatag aagaaaggca aacacaacac attcaacctc     60
tgccaccatg gggaactggg ctgtgaatga ggggctctcc attttttgtca ttctggtttg   120 gctggggttg aacgtcttcc tctttgtctg gtattaccgg gtttatgata ttccacctaa    180
gttcttttac acaagaaaac ttcttgggtc agcactggca ctggccaggg ccctgcagc    240 ctgcctgaat ttcaactgca tgctgattct cttgccagtc tgtcgaaatc tgctgtcctt   300
cctcaggggt tccagtgcgt gctgctcaac aagagttcga agacaactgg acaggaatct   360
cacctttcat aaaaatggtgg catggatgat tgcacttcac tctgcgattc acaccattgc   420 acatctatttt aatgtggaat ggtgtgtgaa tgcccgagtc aataattctg atccttattc   480
agtagcactc tctgaacttg gagacaggca aaatgaaagt tatctcaatt ttgctcgaaa    540
gagaataaag aaccctgaag gaggcctgta cctggctgtg accctgttgg caggcatcac    600
tggagttgtc atcacgctgt gcctcatatt aattatcact tcctccacca aaaccatccg    660
gaggtcttac tttgaagtct tttggtacac acatcatctc tttgtgatct tcttcattgg    720
ccttgccatc catggagctg aacgaattgt acgtgggcag accgcagaga gtttggctgt   780
gcataatata acagtttgtg aacaaaaaat ctcagaatgg ggaaaaataa aggaatgccc    840
aatccctcag tttgctggaa accctcctat gacttggaaa tggatagtgg gtcccatgtt    900
tctgtatctc tgtgagaggt tggtgcggtt ttggcgatct caacgaaagg tggtcatcac    960
caaggtggtc actcaccctt tcaaaaccat cgagctacag atgaagaaga aggggttcaa   1020 aatgaagtg ggacaataca ttttttgtcaa gtgcccaaag gtgtccaagc tggagtggca   1080
cccttttaca ctgacatccg ccctgagga agacttcttt agtatccata tccgcatcgt    1140
```

```
tggggactgg acagaggggc tgttcaatgc ttgtggctgt gataagcagg agtttcaaga    1200
tgcgtggaaa ctacctaaga tagcggttga tgggcccttt ggcactgcca gtgaagatgt    1260
gttcagctat gaggtggtga tgttagtggg agcagggatt ggggtcacac ccttcgcatc    1320
cattctcaag tcagtctggt acaaatattg caataacgcc accaatctga agctcaaaaa    1380
gatctacttc tactggctgt gccgggacac acatgccttt gagtggtttg cagatctgct    1440
gcaactgctg gagagccaga tgcaggaaag gaacaatgcc ggcttcctca gctacaacat    1500
ctacctcact ggctgggatg agtctcaggc caatcacttt gctgtgcacc atgatgagga    1560
gaaagatgtg atcacaggcc tgaaacaaaa gactttgtat ggacggccca actgggataa    1620
tgaattcaag acaattgcaa gtcaacaccc taataccaga ataggagttt tcctctgtgg    1680
acctgaagcc ttggctgaaa ccctgagtaa acaaagcatc tccaactctg agtctggccc    1740
tcggggagtg catttcattt tcaacaagga aaacttctaa cttgtctctt ccatgaggaa    1800
ataaatgtgg gttgtgctgc caaatgctca ataatgcta attgataata taaataccc    1860 ctgcttaaaa atggacaaaa agaaactata atgtaatggt tttcccttaa aggaatgtca    1920
aagattgttt gatagtgata agttacattt atgtggagct ctatggtttt gagagcactt    1980
ttacaaacat tatttcattt ttttcctctc agtaatgtca gtggaagtta gggaaaagat    2040
tcttggactc aattttagaa tcaaaaggga aaggatcaaa aggttcagta acttccctaa    2100
gattatgaaa ctgtgaccag atctagccca tcttactcca ggtttgatac tctttccaca    2160
atactgagct gcctcagaat cctcaaaatc agtttttata ttccccaaaa gaagaaggaa    2220
accaaggagt agctatatat ttctactttg tgtcattttt gccatcatta ttatcatact    2280
gaaggaaatt ttccagatca ttaggacata atacatgttg agagtgtctc aacacttatt    2340
agtgacagta ttgacatctg agcatactcc agtttactaa tacagcaggg taactgggcc    2400
agatgttctt tctacagaag aatattggat tgattggagt taatgtaata ctcatcattt    2460
accactgtgc ttggcagaga gcggatactc aagtaagttt tgttaaatga atgaatgaat    2520
ttagaaccac acaatgccaa gatagaatta atttaaagcc ttaaacaaaa tttatctaaa    2580
gaaataactt ctattactgt catagaccaa aggaatctga ttctccctag ggtcaagaac    2640
aggctaagga tactaaccaa taggattgcc tgaagggttc tgcacattct tatttgaagc    2700
atgaaaaaag agggttggag gtggagaatt aacctcctgc catgactctg gctcatctag    2760
tcctgctcct tgtgctataa aataaatgca gactaatttc ctgcccaaag tggtcttctc    2820
cagctagccc ttatgaatat tgaacttagg aattgtgaca aatatgtatc tgatatggtc    2880
atttgtttta aataacaccc acccttatt ttccgtaaat acacacacaa aatggatcgc    2940
atctgtgtga ctaatggttt atttgtatta tatcatcatc atcatcctaa aattaacaac    3000
ccagaaacaa aaatctctat acagagatca aattcacact caatagtatg ttctgaatat    3060
atgttcaaga gagagtctct aaatcactgt tagtgtggcc aagagcaggg ttttcttttt    3120
gttcttagaa ctgctcccat ttctgggaac taaaaccagt tttatttgcc ccaccccttg    3180
gagccacaaa tgtttagaac tcttcaactt cggtaatgag gaagaaggag aaagagctgg    3240
gggaagggca aagactggt ttaggaggaa aggaaataa ggagaaaaga gaatgggaga    3300
gtgagagaaa ataaaaaagg caaagggag agagagggga agggggtctc atattggtca    3360
ttccctgccc cagatttctt aaagtttgat atgtatagaa tataattgaa ggaggtatac    3420
acatattgat gttgttttga ttatctatgg tattgaatct tttaaaatct ggtcacaaat    3480
tttgatgctg aggggattta ttcaagggac taggatgaac taaataagaa ctcagttgtt    3540
```

```
ctttgtcata ctactattcc tttcgtctcc cagaatcctc agggcactga gggtaggtct    3600
gacaaataag gcctgctgtg cgaatatagc ctttctgaaa tgtaccagga tggtttctgc    3660
ttagagacac ttaggtccag cctgttcaca ctgcacctca ggtatcaatt catctattca    3720
acagatattt attgtgttat tactatgagt caggctctgt ttattgtttc aattctttac    3780
accaaagtat gaactggaga gggtacctca gttataagga gtctgagaat attggcccct    3840
tctaacctat gtgcataatt aaaaccagct tcatttgttg ctccgagagt gtttctccaa    3900
ggttttctat cttcaaaacc aactaagtta tgaaagtaga gagatctgcc ctgtgttatc    3960
cagtatgag ataaaaaatg aatataagag tgcttgtcat tataaaagtt tcctttttta    4020
ttctctcaag ccaccagctg ccagccacca gcagccagct gccagcctag ctttttttt     4080
tttttttttt tttagcact tagtatttag cattattaa caggtactct aagaatgatg     4140
aagcattgtt tttaatctta agactatgaa ggttttctt agttcttctg cttttgcaat    4200
tgtgtttgtg aaatttgaat acttgcaggc tttgtatgtg aataattcta gcggggacc     4260
tgggagataa ttcctacggg gaattcttaa aactgtgctc aactattaaa atgaatgagc    4320
tttc                                                                 4324

<210> SEQ ID NO 37
<211> LENGTH: 1688
<212> TYPE: DNA
<213> ORGANISM: human

<400> SEQUENCE: 37
ggagtcgacc gctcgggcag cgccaccgcc acgagagccc gggacgcggg aaagaccgaa      60
aggaagagga agaggcaccg gtggccatgg ggctggaggc ggcgcgcgag ctggagtgcg     120
cggcgctggg cacgctgctg cgggatccgc gggaggcgga acgcacgctg ctgctggact     180
gccgccccct tcctggcctt ctgccggcgc acgtgcgcgc cgcgcggcca gtgccttgga     240
acgcgctgct gcggcgccgc gcgcgcggcc ctcctgccgc cgttctcgcc tgcctgctgc     300
ccgaccgcgc gctgcggacg cgcctggtcc gcggggagct ggcgcgggcc gtggtgctgg     360
acgagggcag tgcctcggtg gcggagctcc ggcccgacag cccggctcat gtgctgctgg     420
ccgcgctgct gcacgagacc cgcgcggggc ccactgccgt gtacttcctg cgaggaggct     480
tcgacggctt ccagggctgc tgtcccgatc tgtgctctga ggcccccgcc cctgcgctgc     540
cgccaacagg ggacaaaacc agccgctccg actccagggc tcctgtctac gaccagggtg     600
gccctgtgga gatcttgccc tacctgttcc tgggcagctg cagtcactcg tcagacctgc     660
aggggctgca ggcctgtggc atcacagccg tcctcaacgt gtccgccagc tgccccaacc     720
actttgaggg cctttttccgc tacaagagta tccctgtgga ggacaaccag atggtggaga    780
tcagtgcctg gttccaggag gccataggct tcattgactg ggtgaagaac agcggaggcc    840
gggtgctggt gcactgccag gcgggtatct cgcgctctgc caccatctgt ctggcatacc    900
tcatgcagag tcgccgtgtg cggctggacg aggcctttga cttcgttaag cagcgccggg    960
gggtcatctc ccccaacttc agtttcatgg ggcagctgct gcagtttgag acccaggtgc   1020
tgtgtcactg aggtggtgcc cctctgcctg cctgccccac tgtgctggca ggagctgact   1080
gtggactggt gggctcccct ctgggccagc acagtccct cacctctggc agggctgcta    1140
cctcctcaga gtttcagaag cccccacatg ggggctctag gaatgccggc atgctggtct   1200
ttccgacctg gtgctcttct gctggggggac tgaggctggc cctcattcgg ggtcgggaac   1260
```

| | |
|---|---|
| caagggtgtg tctgctcttt ccctccccat cctctggcag aaatcagcta gacgctatac | 1320 |
| cgtggactct ccctggtcca ccaccatgtt gaagcccttg gcagcctgag agctccaagg | 1380 |
| aacaagctgt gacaaccagg agccctgtct gtgggttcgt ctgcccaggg cctggagccc | 1440 |
| aagccctgtg ttcctgggga agctggggac ttgggaagtg atgggtgtgt catgttgcgt | 1500 |
| gtgtctgtct gtgagccttt cacacctgtg ctggcgctgg aaaattattt gtgctcagct | 1560 |
| gacatttaac actccctccc ccgcttcctc ctagccctgt gggcagggggt tggaaactta | 1620 |
| gcactttata tttatacaga acattcagga tatgtcaata aaatattgtt atatttaaaa | 1680 |
| aacaacaa | 1688 |

<210> SEQ ID NO 38
<211> LENGTH: 7783
<212> TYPE: DNA
<213> ORGANISM: human

<400> SEQUENCE: 38

| | |
|---|---|
| aatacttgtt gcaataattg cccacgatag ctgctcaaac aagagagttg gaattcatct | 60 |
| gtaaaaatca ctacatgtaa cgtaggagac aagaaaaata ttaatgacag aagatctgcg | 120 |
| aacatgatgc acgtgaataa ttttcccttt agaaggcatt cctggatatg ttttgatgtg | 180 |
| gacaatggca catctgcggg acggagtccc ttggatccca tgaccagccc aggatccggg | 240 |
| ctaattctcc aagcaaattt tgtccacagt caacgacggg agtccttcct gtatcgatcc | 300 |
| gacagcgatt atgacctctc tccaaagtct atgtcccgga actcctccat gccagtgat | 360 |
| atacacggag atgacttgat tgtgactcca tttgctcagg tcttggccag tctgcgaact | 420 |
| gtacgaaaca actttgctgc attaactaat ttgcaagatc gagcacctag caaaagatca | 480 |
| cccatgtgca accaaccatc catcaacaaa gccaccataa cagaggaggc ctaccagaaa | 540 |
| ctggccagcg agaccctgga ggagctggac tggtgtctgg accagctaga gaccctacag | 600 |
| accaggcact ccgtcagtga gatggcctcc aacaagtta aaaggatgct taatcgggag | 660 |
| ctcacccatc tctctgaaat gagtcggtct ggaaatcaag tgtcagagtt tatatcaaac | 720 |
| acattcttag ataagcaaca tgaagtgaa attccttctc caactcagaa ggaaaaggag | 780 |
| aaaaagaaaa gaccaatgtc tcagatcagt ggagtcaaga aattgatgca cagctctagt | 840 |
| ctgactaatt caagtatccc aaggtttgga gttaaaactg aacaagaaga tgtccttgcc | 900 |
| aaggaactag aagatgtgaa caaatggggt cttcatgttt tcagaatagc agagttgtct | 960 |
| ggtaaccggc ccttgactgt tatcatgcac accattttc aggaacggga tttattaaaa | 1020 |
| acatttaaaa ttccagtaga tactttaatt acatatctta tgactctcga agaccattac | 1080 |
| catgctgatg tggcctatca caacaatatc catgctgcag atgttgtcca gtctactcat | 1140 |
| gtgctattat ctacacctgc tttggaggct gtgtttacag atttggagat tcttgcagca | 1200 |
| attttttgcca gtgcaataca tgatgtgat catcctggtg tgtccaatca atttctgatc | 1260 |
| aatacaaact ctgaacttgc cttgatgtac aatgattcct cagtcttaga gaaccatcat | 1320 |
| ttggctgtgg gctttaaatt gcttcaggaa gaaaactgtg acattttcca gaatttgacc | 1380 |
| aaaaaacaaa gacaatcttt aaggaaaatg gtcattgaca tcgtacttgc aacagatatg | 1440 |
| tcaaaacaca tgaatctact ggctgatttg aagactatgg ttgaaactaa gaaagtgaca | 1500 |
| agctctggag ttcttcttct tgataattat tccgatagga ttcaggttct tcagaatatg | 1560 |
| gtgcactgtg cagatctgag caacccaaca aagcctctcc agctgtaccg ccagtggacg | 1620 |
| gaccggataa tggaggagtt cttccgccaa ggagaccgag agagggaacg tggcatggag | 1680 |

```
ataagcccca tgtgtgacaa gcacaatgct tccgtggaaa aatcacaggt gggcttcata    1740
gactatattg ttcatcccct ctgggagaca tgggcagacc tcgtccaccc tgacgcccag    1800
gatattttgg acactttgga ggacaatcgt gaatggtacc agagcacaat ccctcagagc    1860
ccctctcctg cacctgatga cccagaggag ggccggcagg gtcaaactga gaaattccag    1920
tttgaactaa ctttagagga agatggtgag tcagacacgg aaaaggacag tggcagtcaa    1980
gtggaagaag acactagctg cagtgactcc aagactcttt gtactcaaga ctcagagtct    2040
actgaaattc cccttgatga acaggttgaa gaggaggcag taggggaaga agaggaaagc    2100
cagcctgaag cctgtgtcat agatgatcgt tctcctgaca cgtaacagtg caaaaacttt    2160
catgcctttt tttttttttaa gtagaaaaat tgtttccaaa gtgcatgtca catgccacaa    2220
ccacggtcac acctcactgt catctgccag gacgtttgtt gaacaaaact gaccttgact    2280
actcagtcca gcgctcagga atatcgtaac cagttttttc acctccatgt catccgagca    2340
aggtggacat cttcacgaac agcgttttta acaagatttc agcttggtag agctgacaaa    2400
gcagataaaa tctactccaa attattttca agagagtgtg actcatcagg cagcccaaaa    2460
gtttattgga cttggggttt ctattccttt ttatttgttt gcaatatttt cagaagaaag    2520
gcattgcaca gagtgaactt aatggacgaa gcaacaaata tgtcaagaac aggacatagc    2580
acgaatctgt taccagtagg aggaggatga gccacagaaa ttgcataatt ttctaatttc    2640
aagtcttcct gatacatgac tgaatagtgt ggttcagtga gctgcactga cctctacatt    2700
ttgtatgata tgtaaaacag attttttgta gagcttactt ttattattaa atgtattgag    2760
gtattatatt taaaaaaaac tatgttcaga acttcatctg ccactggtta tttttttcta    2820
aggagtaact tgcaagtttt cagtacaaat ctgtgctaca ctggataaaa atctaattta    2880
tgaattttac ttgcaccta tagttcatag caattaactg atttgtagtg attcattgtt    2940
tgttttatat accaatgact tccatatttt aaaagagaaa aacaacttta tgttgcagga    3000
aacccttttt gtaagtcttt attatttact ttgcattttg tttcactctt tccagataag    3060
cagagttgct cttcaccagt gttttttcttc atgtgcaaag tgactatttg ttctataata    3120
cttttatgtg tgttatatca aatgtgtctt aagcttcatg caaactcagt catcagttcg    3180
tgttgtctga agcaagtggg agatatataa atacccagta gctaaaatgg tcagtctttt    3240
ttagatgttt tcctacttag tatctcctaa taacgttttg ctgtgtcact agatgttcat    3300
ttcacaagtg catgtctttc taataatcca cacatttcat gctctaataa tccacacatt    3360
tcatgctcat tttattgtt tttacagcca gttatagtaa gaaaaaggtt tttccccttg    3420
tgctgcttta taatttagcg tgtgtctgaa ccttatccat gtttgctaga tgaggtcttg    3480
tcaaatatat cactaccatt gtcaccggtg aaaagaaaca ggtagttaag ttagggttaa    3540
cattcatttc aaccacgagg ttgtatatca tgactagctt ttactcttgg tttacagaga    3600
aaagttaaac agccaactag gcagttttta agaatattaa caatatatta acaaacacca    3660
atacaactaa tcctatttgg ttttaatgat ttcaccatgg gattaagaac tatatcagga    3720
acatccctga gaaacggttt taagtgtagc aactactctt ccttaatgga cagccacata    3780
acgtgtagga agtcctttat cacttatcct cgatccataa gcatatcttg cagaggggaa    3840
ctacttcttt aaacacatgg agggaaagaa gatgatgcca ctggcaccag agggttagta    3900
ctgtgatgca tcctaaaata tttattatat tggtaaaaat tctggttaaa taaaaaatta    3960
gagatcactc ttggctgatt tcagcaccag gaactgtatt acagttttag agattaattc    4020
```

```
ctagtgttta cctgattata gcagttggca tcatggggca tttaattctg actttatccc    4080
cacgtcagcc ttaataaagt cttctttacc ttctctatga agactttaaa gcccaaataa    4140 tcattttca cattgatatt caagaattga gatagataga agccaaagtg ggtatctgac    4200
aagtggaaaa tcaaacgttt aagaagaatt acaactctga aaagcattta tatgtggaac    4260
ttctcaagga gcctcctggg gactggaaag taagtcatca gccaggcaaa tgactcatgc    4320
tgaagagagt ccccatttca gtcccctgag atctagctga tgcttagatc ctttgaaata    4380
aaaattatgt ctttataact ctgatctttt acataaagca gaagaggaat caactagtta    4440
attgcaaggt ttctactctg tttcctctgt aaagatcaga tggtaatctt tcaaataaga    4500
aaaaaataaa gacgtatgtt tgaccaagta gtttcacaag aatatttggg aacttgtttc    4560
ttttaatttt atttgtccct gagtgaagtc tagaaagaaa ggtaaagagt ctagagttta    4620
ttcctctttc caaaacattc tcattcctct cctccctaca cttagtattt cccccacaga    4680
gtgcctagaa tcttaataat gaataaaata aaaagcagca atatgtcatt aacaaatcca    4740
gacctgaaag ggtaaagggt ttataactgc actaataaag agaggctctt ttttttttctt    4800 ccagtttgtt ggttttttaat ggtaccgtgt tgtaaagata cccactaatg gacaatcaaa    4860
ttgcagaaaa ggctcaatat ccaagagaca gggactaatg cactgtacaa tctgcttatc    4920
cttgcccttc tctcttgcca aagtgtgctt cagaaatata tactgcttta aaaagaata    4980 aagaatatc cttttacaag tggctttaca tttcctaaaa tgccataaga aaatgcaata    5040
tctgggtact gtatggggaa aaaatgtcc aagtttgtgt aaaaccagtg catttcagct    5100
tgcaagttac tgaacacaat aatgctgttt taattttgtt ttatatcagt taaaattcac    5160
aataatgtag atagaacaaa ttacagacaa ggaaagaaaa aacttgaatg aaatggattt    5220
tacagaaagc tttatgataa ttttttgaatg cattatttat tttttgtgcc atgcattttt    5280
tttctcacca aatgacctta cctgtaatac agtcttgttt gtctgtttac aaccatgtat    5340
ttattgcaat gtacatactg taatgttaat tgtaaattat ctgttcttat taaaacatca    5400
tcccatgatg ggatggtgtt gatatatttg gaaactcttg gtgagagaat gaatggtgtg    5460
tatacatact ctgtacattt ttcttttctc ctgtaatata gtcttgtcac cttagagctt    5520
gtttatggaa gattcaagaa aactataaaa tacttaaaga tatataaatt taaaaaaaca    5580
tagctgcagg tctttggtcc cagggctgtg ccttaacttt aaccaatatt tcttctgtt    5640 ttgctgcatt tgaaaggtaa cagtggagct agggctgggc attttacatc caggctttta    5700
attgattaga attctgccaa taggtggatt ttacaaaacc acagacaacc tctgaaagat    5760
tctgagaccc ttttgagaca gaagctctta agtacttctt gccagggagc agcactgcat    5820
gtgtgatggt tgtttgccat ctgttgatca ggaactactt cagctacttg catttgatta    5880 ttttccttttt tttttttttt aactcggaaa cacaactggg gaaatatatt ctttcccagt    5940
gattataaac aatctttttc tttttttttaa gtccttttgg cttctagagc tcataggaaa    6000
atggacttga tttgaaattg gagccagagt ttactcgtgt tggttatcta ttcatcagct    6060
tcctgacatg ttaagagaat acattaaaga gaaaatactg ttttttaatc ctaaaatttt    6120
tcttccacta agataaacca aatgtcctta catatatgta aacccatcta tttaaacgca    6180
aaggtgggtt gatgtcagtt tacatagcag aaagcattca ctatcctcta agatttgttt    6240
ctgcaaaact ttcattgctt tagaattttta aaatttcacc ttgtacaatg gccagcccct    6300
aaagcaggaa acatttataa tggattatat ggaaacatcc tcccagtact tgcccagccc    6360
ttgaatcatg tggcttttca gtgaaaggaa agattctttt tctaggaaaa atgagcctat    6420
```

```
tttattttat ttttattttat tttttgacac aaactgtaga ttttagcagc cctggcccaa    6480
aggaatttga ttacttttgt tttaaacagt acaaagggga cactataatt acaaaaacat    6540
ccttaactga tttgagttgt ttttatttct ttggatatat tttcagagtg gtaaattgtg    6600
tgtgagaatt acaaatgatt attcttttag tggtttctta gcctctctta cagcccacgg    6660
ggatagtact gtacatcaat accttcatat gaatttttta tatgcaatga aaataaaagc    6720
atgggttgat tctgcctatt tatgactcaa tcttttacaa ataaaagatt attcatttta    6780
aattatagtt caatcagcat gtctcttagg atactgaacg tggttgaaat gaaaggatag    6840
tgacatcata agttagtact gatattcata accaaataaa gccaacttga gtaattttgc    6900
tacattaaaa attaccaaaa ttacttagat ggcctataag attaagcatg gtgttttcta    6960
agcaagcttt gaagggggcc ttccatactt acttaattga atattctggg atattgaaaa    7020
ttattcagat acttgacaat tatttttggt tacctactcc gcaaactaca agttttaag    7080 gactcaacaa taagttaatg agacacagtg tttgctttca tggagcttac agtctggagg    7140
ggacaaaggc ttaaacaata ctcatataat tatatatgtg atcagtacaa tgaaggagct    7200
cagtggggta aataagcagg aacctgaact tgatctgttc cggagggcca cagaaggctt    7260
ccttgaggcc ttgagaaagt gatttgcatc tgagttctga aggattgtaa gaggtaacta    7320
gggaaaaagt tgacaggaag aggaagggga tccagacaag aaacatttgc aaagatcttg    7380
aggcataaat gagcttgaga catctggaga aactgaggaa aagtgagaga gtaggcaggg    7440
cctggagccg cagagccatt gctaaccatc ctgtgtgaga tatcccccat tctgtagctt    7500
tattctcata accctgctca attttcttta taacacttct cacagattta tatacgtgtt    7560 tgttttttgtt atctgtctct cccaccagac cacagctcca tgagagcaag gtctttgctt    7620
accaatatat cactagcact taaaactatg cctggtacac agtaggttct taatatgtgt    7680
tgaatatagc catcaaattg atattggata taattcaatc tgataagata ttttgagata    7740
ttaaagagtt tttaacttga taccataaaa aaaaaaaaaa aaa                      7783
```

<210> SEQ ID NO 39
<211> LENGTH: 8240
<212> TYPE: DNA
<213> ORGANISM: human

<400> SEQUENCE: 39

```
cccctctcgg tagccctgag gctctggcgc cttcaagtga gaagctaagc accagcctct     60
gctgggctgc agaagcggcg gcggcggcag cagcagcagc agcatcagga aggcgctcgg    120
gccagcgcgg tgaacccggg ctgggcagca ggtcgcggag ccgcgagcca ggatggaggc    180
agagggcagc agcgcgccgg cccggcgggg cagcggagag ggcagcgaca cgcgcggcgg    240
ggccacgctc aaagccccca agcatctctg gaggcacgag cagcaccacc agtacccgct    300
ccggcagccc cagttccgcc tcctgcatcc ccatcaccac ctgccccgc cgccgccacc    360 ctcgccccag ccccagcccc agtgtccgct acagccgccg ccgccgcccc cctgccgcc    420 gccccgccg ccgcccgggg ctgcccgcgg ccgctacgcc tcgagcgggg ccaccggccg    480
cgtccggcat cgcggctact cggacaccga gcgctacctg tactgtcgcg ccatggaccg    540
cacctcctac gcggtggaga ccggccaccg gcccggcctg aagaaatcca ggatgtcctg    600
gccctcctcg ttccagggac tcaggcgttt tgatgtggac aatggcacat ctgcgggacg    660 gagtccttg gatcccatga ccagcccagg atccgggcta attctccaag caaatttgt     720
```

```
ccacagtcaa cgacgggagt ccttcctgta tcgatccgac agcgattatg acctctctcc    780
aaagtctatg tcccggaact cctccattgc cagtgatata cacggagatg acttgattgt    840
gactccattt gctcaggtct tggccagtct gcgaactgta cgaaacaact ttgctgcatt    900
aactaatttg caagatcgag cacctagcaa aagatcaccc atgtgcaacc aaccatccat    960
caacaaagcc accataacag aggaggccta ccagaaactg ccagcgaga ccctggagga    1020
gctggactgg tgtctggacc agctagagac cctacagacc aggcactccg tcagtgagat   1080
ggcctccaac aagtttaaaa ggatgcttaa tcgggagctc acccatctct ctgaaatgag   1140
tcggtctgga aatcaagtgt cagagtttat atcaaacaca ttcttagata agcaacatga   1200
agtggaaatt ccttctccaa ctcagaagga aaaggagaaa aagaaaagac caatgtctca   1260
gatcagtgga gtcaagaaat tgatgcacag ctctagtctg actaattcaa gtatcccaag   1320
gtttggagtt aaaactgaac aagaagatgt ccttgccaag gaactagaag atgtgaacaa   1380
atggggtctt catgttttca gaatagcaga gttgtctggt aaccggccct tgactgttat   1440
catgcacacc attttcagg aacgggattt attaaaaaca tttaaaattc cagtagatac    1500
tttaattaca tatcttatga ctctcgaaga ccattaccat gctgatgtgg cctatcacaa   1560
caatatccat gctgcagatg ttgtccagtc tactcatgtg ctattatcta cacctgcttt   1620
ggaggctgtg tttacagatt tggagattct tgcagcaatt tttgccagtg caatacatga   1680
tgtagatcat cctggtgtgt ccaatcaatt tctgatcaat acaaactctg aacttgcctt   1740
gatgtacaat gattcctcag tcttagagaa ccatcatttg gctgtgggct ttaaattgct   1800
tcaggaagaa aactgtgaca ttttccagaa tttgaccaaa aaacaaagac aatctttaag   1860
gaaaatggtc attgacatcg tacttgcaac agatatgtca aaacacatga atctactggc   1920
tgatttgaag actatggttg aaactaagaa agtgacaagc tctggagttc ttcttcttga   1980
taattattcc gataggattc aggttcttca gaatatggtg cactgtgcag atctgagcaa   2040
cccaacaaag cctctccagc tgtaccgcca gtggacggac cggataatgg aggagttctt   2100
ccgccaagga gaccgagaga gggaacgtgg catggagata agccccatgt gtgacaagca   2160
caatgcttcc gtggaaaaat cacaggtggg cttcatagac tatattgttc atccctctg    2220
ggagacatgg gcagacctcg tccaccctga cgcccaggat attttggaca ctttggagga   2280
caatcgtgaa tggtaccaga gcacaatccc tcagagcccc tctcctgcac ctgatgaccc   2340
agaggagggc cggcagggtc aaactgagaa attccagttt gaactaactt tagaggaaga   2400
tggtgagtca gacacggaaa aggacagtgg cagtcaagtg gaagaagaca ctagctgcag   2460
tgactccaag actctttgta ctcaagactc agagtctact gaaattcccc ttgatgaaca   2520
ggttgaagag gaggcagtag gggaagaaga ggaaagccag cctgaagcct gtgtcataga   2580
tgatcgttct cctgacacgt aacagtgcaa aaactttcat gcctttttt ttttttaagta   2640
gaaaaattgt ttccaaagtg catgtcacat gccacaacca cggtcacacc tcactgtcat   2700
ctgccaggac gtttgttgaa caaaactgac cttgactact cagtccagcg ctcaggaata   2760
tcgtaaccag tttttcacc tccatgtcat ccgagcaagg tggacatctt cacgaacagc    2820
gttttttaaca agatttcagc ttggtagagc tgacaaagca gataaaatct actccaaatt   2880
attttcaaga gagtgtgact catcaggcag cccaaaagtt tattggactt ggggtttcta   2940
ttccttttta tttgtttgca atattttcag aagaaaggca ttgcacagag tgaacttaat   3000
ggacgaagca acaaatatgt caagaacagg acatagcacg aatctgttac cagtaggagg   3060
aggatgagcc acagaaattg cataattttc taatttcaag tcttcctgat acatgactga   3120
```

```
atagtgtggt tcagtgagct gcactgacct ctacattttg tatgatatgt aaaacagatt    3180
ttttgtagag cttactttta ttattaaatg tattgaggta ttatatttaa aaaaaactat    3240
gttcagaact tcatctgcca ctggttattt ttttctaagg agtaacttgc aagttttcag    3300
tacaaatctg tgctacactg gataaaaatc taatttatga attttacttg caccttatag    3360
ttcatagcaa ttaactgatt tgtagtgatt cattgtttgt tttatatacc aatgacttcc    3420
atattttaaa agagaaaaac aactttatgt tgcaggaaac ccttttttgta agtctttatt    3480 atttactttg cattttgttt cactcttttcc agataagcag agttgctctt caccagtgtt    3540
tttcttcatg tgcaaagtga ctatttgttc tataatactt ttatgtgtgt tatatcaaat    3600
gtgtcttaag cttcatgcaa actcagtcat cagttcgtgt tgtctgaagc aagtgggaga    3660
tatataaata cccagtagct aaaatggtca gtcttttta gatgttttcc tacttagtat    3720
ctcctaataa cgttttgctg tgtcactaga tgttcatttc acaagtgcat gtctttctaa    3780
taatccacac atttcatgct ctaataatcc acacatttca tgctcatttt tattgttttt    3840
acagccagtt atagtaagaa aaaggttttt ccccttgtgc tgctttataa tttagcgtgt    3900
gtctgaacct tatccatgtt tgctagatga ggtcttgtca aatatatcac taccattgtc    3960
accggtgaaa agaaacaggt agttaagtta gggttaacat tcatttcaac cacgaggttg    4020
tatatcatga ctagctttta ctcttggttt acagagaaaa gttaaacagc caactaggca    4080
gtttttaaga atattaacaa tatattaaca aacaccaata caactaatcc tatttggttt    4140
taatgatttc accatgggat taagaactat atcaggaaca tccctgagaa acggttttaa    4200
gtgtagcaac tactcttcct taatggacag ccacataacg tgtaggaagt cctttatcac    4260
ttatcctcga tccataagca tatcttgcag aggggaacta cttcttttaaa cacatggagg    4320 gaaagaagat gatgccactg gcaccagagg gttagtactg tgatgcatcc taaaatattt    4380
attatattgg taaaaattct ggttaaataa aaaattagag atcactcttg gctgatttca    4440
gcaccaggaa ctgtattaca gttttagaga ttaattccta gtgttaccct gattatagca    4500
gttggcatca tggggcattt aattctgact ttatccccac gtcagcctta ataaagtctt    4560
ctttaccttc tctatgaaga ctttaaagcc caaataatca ttttttcacat tgatattcaa    4620 gaattgagat agatagaagc caaagtgggt atctgacaag tggaaaatca aacgtttaag    4680
aagaattaca actctgaaaa gcatttatat gtggaacttc tcaaggagcc tcctggggac    4740
tggaaagtaa gtcatcagcc aggcaaatga ctccatgctga agagagtccc catttcagtc    4800
ccctgagatc tagctgatgc ttagatcctt tgaaataaaa attatgtctt tataactctg    4860 atctttaca taaagcagaa gaggaatcaa ctagttaatt gcaaggtttc tactctgttt    4920
cctctgtaaa gatcagatgg taatctttca aataagaaaa aaataaagac gtatgtttga    4980
ccaagtagtt tcacaagaat atttgggaac ttgtttcttt taattttatt tgtccctgag    5040
tgaagtctag aaagaaaggt aaagagtcta gagtttattc ctctttccaa acattctca    5100 ttcctctcct ccctacactt agtatttccc ccacagagtg cctagaatct taataatgaa    5160
taaaataaaa agcagcaata tgtcattaac aaatccagac ctgaaagggt aaagggttta    5220
taactgcact aataaagaga ggctcttttt ttttcttcca gtttgttggt ttttaatggt    5280
accgtgttgt aaagataccc actaatggac aatcaaattg cagaaaaggc tcaatatcca    5340
agagacaggg actaatgcac tgtacaatct gcttatcctt gcccttctct cttgccaaag    5400
tgtgcttcag aaatatatac tgctttaaaa aagaataaaa gaatatcctt ttacaagtgg    5460
```

-continued

```
ctttacattt cctaaaatgc cataagaaaa tgcaatatct gggtactgta tggggaaaaa      5520
aatgtccaag tttgtgtaaa accagtgcat ttcagcttgc aagttactga acacaataat      5580
gctgttttaa ttttgtttta tatcagttaa aattcacaat aatgtagata gaacaaatta      5640
cagacaagga aagaaaaaac ttgaatgaaa tggattttac agaaagcttt atgataattt      5700
ttgaatgcat tatttatttt ttgtgccatg cattttttt ctcaccaaat gaccttacct      5760
gtaatacagt cttgtttgtc tgtttacaac catgtattta ttgcaatgta catactgtaa      5820
tgttaattgt aaattatctg ttcttattaa aacatcatcc catgatggga tggtgttgat      5880
atatttggaa actcttggtg agagaatgaa tggtgtgtat acatactctg tacatttttc      5940
ttttctcctg taatatagtc ttgtcacctt agagcttgtt tatggaagat tcaagaaaac      6000
tataaaatac ttaaagatat ataaatttaa aaaaacatag ctgcaggtct ttggtcccag      6060
ggctgtgcct taactttaac caatattttc ttctgttttg ctgcatttga aggtaacag       6120 tggagctagg gctgggcatt ttacatccag gcttttaatt gattagaatt ctgccaatag      6180
gtggatttta caaaccaca gacaacctct gaaagattct gagaccctt tgagacagaa        6240 gctcttaagt acttcttgcc agggagcagc actgcatgtg tgatggttgt ttgccatctg      6300
ttgatcagga actactcag ctacttgcat ttgattattt cctttttttt ttttttttaac     6360 tcggaaacac aactggggaa atatattctt tcccagtgat tataaacaat cttttctttt      6420
tttttaagtc cttttggctt ctagagctca taggaaaatg gacttgattt gaaattggag      6480
ccagagttta ctcgtgttgg ttatctattc atcagcttcc tgacatgtta agagaataca     6540
ttaaagagaa aatactgttt tttaatccta aaatttttct tccactaaga taaaccaaat      6600
gtccttacat atatgtaaac ccatctattt aaacgcaaag gtgggttgat gtcagtttac      6660
atagcagaaa gcattcacta tcctctaaga tttgttctg caaaactttc attgctttag      6720
aattttaaaa tttcaccttg tacaatggcc agccctaaa gcaggaaaca tttataatgg      6780
attatatgga aacatcctcc cagtacttgc ccagcccttg aatcatgtgg cttttcagtg     6840
aaaggaaaga ttcttttcct aggaaaaatg agcctatttt attttatttt attttatttt     6900
ttgacacaaa ctgtagattt tagcagcccct ggcccaaagg aatttgatta cttttgttt    6960 aaacagtaca aaggggacac tataattaca aaaacatcct taactgattt gagttgtttt     7020 tatttcttg gatatatttt cagagtggta aattgtgtgt gagaattaca aatgattatt     7080
cttttagtgg tttcttagcc tctcttacag cccacgggga tagtactgta catcaatacc     7140
ttcatatgaa attttatat gcaatgaaaa taaaagcatg ggttgattct gcctatttat     7200
gactcaatct tttacaaata aaagattatt cattttaaat tatagttcaa tcagcatgtc     7260
tcttaggata ctgaacgtgg ttgaaatgaa aggatagtga catcataagt tagtactgat     7320
attcataacc aaataaagcc aacttgagta attttgctac attaaaaatt accaaaatta     7380
cttagatggc ctataagatt aagcatggtg ttttctaagc aagctttgaa aggggccttc     7440
catacttact taattgaata ttctgggata ttgaaaatta ttcagatact tgacaattat     7500
ttttggttac ctactccgca aactacaaag ttttaaggac tcaacaataa gttaatgaga     7560
cacagtgttt gctttcatgg agcttacagt ctggagggga caaaggctta aacaatactc     7620
atataattat atatgtgatc agtacaatga aggagctcag tggggtaaat aagcaggaac     7680
ctgaacttga tctgttccgg agggccacag aaggcttcct tgaggccttg agaaagtgat     7740
ttgcatctga gttctgaagg attgtaagag gtaactaggg aaaaagttga caggaagagg     7800
aaggggatcc agacaagaaa catttgcaaa gatcttgagg cataaatgag cttgagacat     7860
```

| | |
|---|---|
| ctggagaaac tgaggaaaag tgagagagta ggcagggcct ggagccgcag agccattgct | 7920 |
| aaccatcctg tgtgagatat cccccattct gtagctttat tctcataacc ctgctcaatt | 7980 |
| ttctttataa cacttctcac agatttatat acgtgtttgt ttttgttatc tgtctctccc | 8040 |
| accagaccac agctccatga gagcaaggtc tttgcttacc aatatatcac tagcacttaa | 8100 |
| aactatgcct ggtacacagt aggttcttaa tatgtgttga atatagccat caaattgata | 8160 |
| ttggatataa ttcaatctga taagatattt tgagatatta aagagttttt aacttgatac | 8220 |
| cataaaaaaa aaaaaaaaaa | 8240 |

<210> SEQ ID NO 40
<211> LENGTH: 1599
<212> TYPE: DNA
<213> ORGANISM: human

<400> SEQUENCE: 40

| | |
|---|---|
| gggtaaggcg acatttcctg cccccggggc cagggtgaga ggagagatga tgagttgctg | 60 |
| agtgtgcaca cctttccgga acacatacac acccctgct ctgggatccc ttgtgaggct | 120 |
| gccctcatgg agttcccct ggcccagata tgtccccaag caccttccag atcacagaca | 180 |
| tgaccgcag gagctgccag aacctgggct acactgcggc atctcccag gccccggagg | 240 |
| ctgcctccaa cacagggaat gctgagaggg cagaggaggt gcctggagaa ggaagcctgt | 300 |
| tcctgcaggc cgagacccgg gcttggttcc agaagaccca ggcccactgg ctcctgcagc | 360 |
| acggggcagc ccctgcctgg ttccatggct tcatcacccg gagggaggca gagaggctgc | 420 |
| tggagcccaa gcctcagggg tgctacttgg tgcggttcag cgagagcgcg gtgaccttcg | 480 |
| tgctgactta caggagccgg acttgctgcc gccacttcct gctggcccag ctcagggacg | 540 |
| gcgccacgt ggtgctgggc gaggacagcg cccacgcgcg gctgcaggac ctgctgctgc | 600 |
| actacaccgc gcacccgctc agccctacg gggagacgct caccgagccc ctcgcccgac | 660 |
| agactcctga gcctgcagga cttccctga ggaccgaaga atcaaactt ggaagcaaaa | 720 |
| gccaggaccc aaaccccag tacagcccaa tcatcaaaca ggggcaagcc ccagtccga | 780 |
| tgcagaaaga gggggccggg gagaaggagc cctcccagct gctcaggccc aagcctccca | 840 |
| tccccgccaa acctcagctg cccccagaag tctacacaat ccctgttcca cgacaccgcc | 900 |
| cggccccacg ccccaagccc tccaatccta tctacaatga gctgatgaa cccatagctt | 960 |
| tctatgccat gggccggggc agccctgggg aagcccccag caacatctat gtggaagtgg | 1020 |
| aagatgaggg cctacccgcc acccttgggc accctgtcct acggaagagc tggtccaggc | 1080 |
| ctgtcccagg aggccagaat acaggtggct cccagctgca ttctgagaac tctgtgattg | 1140 |
| ggcaaggcc tcccctgccc caccagcccc caccgcctg gagacacac ctcccccaca | 1200 |
| atctttctag acaggtgctt caggacagag acaggcatg gcttcccctt gggcctcctc | 1260 |
| agtaggcggt ctggcctgac ccccaacaaa gaagcctgga ggtcagagaa gcaaatgcgg | 1320 |
| agcctgctcc ctcctaagaa gatcccaaga atccaatggc tcagtccttg gtgatctaag | 1380 |
| acagcaaaga agtgtgcaag gagggccctg ttagctccca ctgtcctggt ttctcctcct | 1440 |
| ggagtctaat ttccttggcc ctctgagcct tttgagtctg ggcccggtc caatgctgct | 1500 |
| gttgtctgag gaatggtttg gtgagaacag atgttagaac ttgtttgttg attcttgtct | 1560 |
| ggctaataaa tcatcaccaa ctgccttctc ctacaggga | 1599 |

<210> SEQ ID NO 41

```
<211> LENGTH: 1658
<212> TYPE: DNA
<213> ORGANISM: human

<400> SEQUENCE: 41
cgtgagtcct cgccagaact aaggctgtgg gtaaggcgac atttcctgcc cccggggcca      60
gggtgagagg agagatgatg agttgctgag tgtgcacacc tttccggaac acatacacac     120
accctgctct gggatccctt gtgaggctgc cctcatggag ttcccctgg cccagatatg      180
tccccaaggg agtcacgaag cccccatccc aaccttcagc accttccaga tcacagacat     240
gacccgcagg agctgccaga acctgggcta cactgcggca tctccccagg ccccggaggc     300
tgcctccaac acagggaatg ctgagagggc agaggaggtg cctggagaag gaagcctgtt     360
cctgcaggcc gagacccggg cttggttcca aagacccag gcccactggc tcctgcagca      420
cggggcagcc cctgcctggt tccatggctt catcacccgg agggaggcag agaggctgct     480
ggagcccaag cctcaggggt gctacttggt gcggttcagc gagagcgcgg tgaccttcgt     540
gctgacttac aggagccgga cttgctgccg ccacttcctg ctggcccagc tcaggacgg      600
gcgccacgtg gtgctgggcg aggacagcgc ccacgcgcgg ctgcaggacc tgctgctgca     660
ctacaccgcg caccgctca gccctacgg ggagacgctc accgagcccc tcgcccgaca      720
gactcctgag cctgcaggac tttcctgag gaccgaagaa tcaaactttg gaagcaaaag      780
ccaggaccca accccagt acagcccaat catcaaacag gggcaagccc cagtccgat       840
gcagaaagag ggggccgggg agaaggagcc ctcccagctg tcaggcccca agcctcccat     900
cccgccaaa cctcagctgc ccccagaagt ctacacaatc cctgttccac gacaccgccc      960
ggccccacgc cccaagccct ccaatcctat ctacaatgag cctgatgaac ccatagcttt     1020
ctatgccatg ggccgggca gccctgggga agccccagc aacatctatg tggaagtgga      1080
agatgagggc ctaccgcca cccttgggca ccctgtccta cggaagagct ggtccaggcc     1140
tgtcccagga ggccagaata caggtggctc ccagctgcat tctgagaact ctgtgattgg     1200
gcaaggccct cccctgcccc accagccccc accgcctgg agacacaccc tccccacaa      1260
tctttctaga caggtgcttc aggacagagg acaggcatgg cttccccttg ggcctcctca     1320
gtaggcggtc tggcctgacc cccaacaaag aagcctggag gtcagagaag caaatgcgga     1380
gcctgctccc tcctaagaag atcccaagaa tccaatggct cagtccttgg tgatctaaga     1440
cagcaaagaa gtgtgcaagg agggccctgt tagctcccac tgtcctggtt ctcctcctg     1500
gagtctaatt tccttggccc tctgagcctt ttgagtctgg gcctggtcc aatgctgctg     1560
ttgtctgagg aatggttgg tgagaacaga tgttagaact tgtttgttga ttcttgtctg     1620
gctaataaat catcaccaac tgccttctcc tacaggga                            1658

<210> SEQ ID NO 42
<211> LENGTH: 1635
<212> TYPE: DNA
<213> ORGANISM: human

<400> SEQUENCE: 42
cggggccagg gtgagaggag agatgatgag ttgctgagtg tgcacacctt tccggaacac      60
atacacacac cctgctctgg gatcccttgt gaggctgccc tcatggagtt ccccctggcc     120
cagatatgtc cccaagggag tcacgaagcc ccatcccaa ccttcagcac cttccagatc      180
acagacatga cccgcaggag ctgccagaac ctgggctaca ctgcggcatc tccccaggcc     240
ccggaggctg cctccaacac agggaatgct gagagggcag aggaggtgcc tggagaagga     300
```

```
agcctgttcc tgcaggccga gacccgggct tggttccaga agacccaggc ccactggctc        360
ctgcagcacg gggcagcccc tgcctggttc catggcttca tcacccggag ggttcggccc        420
cctctctccg tcacccacag ggaggcagag aggctgctgg agcccaagcc tcagggtgc         480 tacttggtgc ggttcagcga gagcgcggtg accttcgtgc tgacttacag gagccggact        540
tgctgccgcc acttcctgct ggcccagctc agggacgggc ccacgtggt gctgggcgag         600 gacagcgccc acgcgcggct gcaggacctg ctgctgcact acaccgcgca cccgctcagc        660
ccctacgggg agacgctcac cgagcccctc gcccgacaga ctcctgagcc tgcaggactt        720
tccctgagga ccgaagaatc aaactttgga agcaaaagcc aggacccaaa cccccagtac        780
agcccaatca tcaaacaggg gcaagcccca gtcccgatgc agaaagaggg ggccggggag        840
aaggagccct cccagctgct caggcccaag cctcccatcc ccgccaaacc tcagctgccc        900
ccagaagtct acacaatccc tgttccacga caccgcccgg cccacgccc caagccctcc        960 aatcctatct acaatgagcc tgatgaaccc atagctttct atgccatggg ccggggcagc       1020
cctggggaag cccccagcaa catctatgtg aagtggaag atgagggcct acccgccacc        1080
cttgggcacc ctgtcctacg gaagagctgg tccaggcctg tcccaggagg ccagaataca       1140
ggtggctccc agctgcattc tgagaactct gtgattgggc aaggccctcc cctgcccac        1200 cagcccccac ccgcctggag acacaccctc ccccacaatc tttctagaca ggtgcttcag       1260
gacagaggac aggcatggct tccccttggg cctcctcagt aggcggtctg gcctgacccc       1320
caacaaagaa gcctggaggt cagagaagca aatgcggagc ctgctccctc ctaagaagat       1380
cccaagaatc caatggctca gtccttggtg atctaagaca gcaaagaagt gtgcaaggag       1440
ggccctgtta gctcccactg tcctggtttc tcctcctgga gtctaatttc cttggccctc       1500
tgagcctttt gagtctgggc cctggtccaa tgctgctgtt gtctgaggaa tggtttggtg       1560
agaacagatg ttagaacttg tttgttgatt cttgtctggc taataaatca tcaccaactg       1620
ccttctccta caggg                                                       1635

<210> SEQ ID NO 43
<211> LENGTH: 9059
<212> TYPE: DNA
<213> ORGANISM: human

<400> SEQUENCE: 43
gagaaggacg cgcggccccc agcgcctctt gggtggccgc ctcggagcat gaccccgcg         60 ggccagcgcc gcgcgctctg atccgaggag accccgcgct cccgcagcca tggccaccgg      120
gggccggcgg ggggcggcgg ccgcgccgct gctggtggcg gtggccgcgc tgctactggg      180
cgccgcgggc cacctgtacc ccggagaggt gtgtccggc atggatatcc ggaacaacct      240
cactaggttg catgagctgg agaattgctc tgtcatcgaa ggacacttgc agatactctt      300
gatgttcaaa acgaggcccg aagatttccg agacctcagt ttccccaaac tcatcatgat      360
cactgattac ttgctgctct ccgggtctca tgggctcgag agcctgaagg acctgttccc      420
caacctcacg gtcatccggg gatcacgact gttctttaac tacgcgctgg tcatcttcga      480
gatggttcac ctcaaggaac tcggcctcta caacctgatg aacatcaccc ggggttctgt      540
ccgcatcgag aagaacaatg agctctgtta cttggccact atcgactggt cccgtatcct      600
ggattccgtg gaggataatt acatcgtgtt gaacaaagat gacaacgagg agtgtggaga      660
catctgtccg ggtaccgcga agggcaagac caactgcccc gccaccgtca tcaacgggca      720
```

-continued

```
gtttgtcgaa cgatgttgga ctcatagtca ctgccagaaa gtttgcccga ccatctgtaa    780
gtcacacggc tgcaccgccg aaggcctctg ttgccacagc gagtgcctgg gcaactgttc    840
tcagcccgac gaccccacca agtgcgtggc ctgccgcaac ttctacctgg acggcaggtg    900
tgtggagacc tgcccgcccc cgtactacca cttccaggac tggcgctgtg tgaacttcag    960
cttctgccag gacctgcacc acaaatgcaa gaactcgcgg aggcagggct gccaccagta   1020
cgtcattcac aacaacaagt gcatccctga gtgtccctcc gggtacacga tgaattccag   1080
caacttgctg tgcaccccat gcctgggtcc ctgtcccaag gtgtgccacc tcctagaagg   1140
cgagaagacc atcgactcgg tgacgtctgc ccaggagctc cgaggatgca ccgtcatcaa   1200
cgggagtctg atcatcaaca ttcgaggagg caacaatctg gcagctgagc tagaagccaa   1260
cctcggcctc attgaagaaa tttcagggta tctaaaaatc cgccgatcct acgtctggt    1320
gtcactttcc ttcttccgga agttacgtct gattcgagga gagaccttgg aaattgggaa   1380
ctactccttc tatgccttgg acaaccagaa cctaaggcag ctctgggact ggagcaaaca   1440
caacctcacc atcactcagg ggaaactctt cttccactat aacccaaaac tctgcttgtc   1500
agaaatccac aagatggaag aagtttcagg aaccaagggg cgccaggaga gaaacgacat   1560
tgccctgaag accaatgggg accaggcatc ctgtgaaaat gagttactta aattttctta   1620
cattcggaca tcttttgaca agatcttgct gagatgggag ccgtactggc cccccgactt   1680
ccgagacctc ttgggggttca tgctgttcta caaagaggcc ccttatcaga atgtgacgga   1740
gttcgacggg caggatgcgt gtggttccaa cagttggacg gtggtagaca ttgacccacc   1800
cctgaggtcc aacgaccccca aatcacagaa ccacccaggg tggctgatgc ggggtctcaa   1860
gccctggacc cagtatgcca tctttgtgaa gaccctggtc accttttcgg atgaacgccg   1920
gacctatggg gccaagagtg acatcattta tgtccgagaca gatgccacca cccctctgt    1980
gccctggat ccaatctcag tgtctaactc atcatcccag attattctga agtggaaacc    2040
accctccgac cccaatggca acatcacccca taccctggtt ttctgggaga ggcaggcgga   2100
agacagtgag ctgttcgagc tggattattg cctcaaaggg ctgaagctgc cctcgaggac   2160
ctggtctcca ccattcgagt ctgaagattc tcagaagcac aaccagagtg agtatgagga   2220
ttcggccggc gaatgctgct cctgtccaaa gacagactct cagatcctga aggagctgga   2280
ggagtcctcg tttaggaaga cgtttgagga ttacctgcac aacgtggttt tcgtccccag   2340
aaaaacctct tcaggcactg gtgccgagga ccctaggcca tctcggaaac gcaggtccct   2400
tggcgatgtt gggaatgtga cggtggccgt gcccacggtg gcagctttcc ccaacacttc   2460
ctcgaccagc gtgcccacga gtccggagga gcacaggcct tttgagaagg tggtgaacaa   2520
ggagtcgctg gtcatctccg gcttgcgaca cttcacgggc tatcgcatcg agctgcaggc   2580
ttgcaaccag gacacccctg aggaacggtg cagtgtggca gcctacgtca gtgcgaggac   2640
catgcctgaa gccaaggctg atgacattgt tggccctgtg acgcatgaaa tctttgagaa   2700
caacgtcgtc cacttgatgt ggcaggagcc gaaggagccc aatggtctga tcgtgctgta   2760
tgaagtgagt tatcggcgat atggtgatga ggagctgcat ctctgcgtct cccgcaagca   2820
cttcgctctg gaacggggct gcaggctgcg tgggctgtca ccggggaact acagcgtgcg   2880
aatccgggcc acctcccttg cgggcaacgg ctcttggacg gaacccacct atttctacgt   2940
gacagactat ttagacgtcc cgtcaaatat tgcaaaaatt atcatcggcc ccctcatctt   3000
tgtctttctc ttcagtgttg tgattggaag tatttatcta ttcctgagaa agaggcagcc   3060
agatgggccg ctgggaccgc tttacgcttc ttcaaaccct gagtatctca gtgccagtga   3120
```

```
tgtgtttcca tgctctgtgt acgtgccgga cgagtgggag gtgtctcgag agaagatcac   3180
cctccttcga gagctggggc agggctcctt cggcatggtg tatgagggca atgccaggga   3240
catcatcaag ggtgaggcag agacccgcgt ggcggtgaag acggtcaacg agtcagccag   3300
tctccgagag cggattgagt tcctcaatga ggcctcggtc atgaagggct tcacctgcca   3360
tcacgtggtg cgcctcctgg gagtggtgtc caagggccag cccacgctgg tggtgatgga   3420
gctgatggct cacggagacc tgaagagcta cctccgttct ctgcggccag aggctgagaa   3480
taatcctggc cgcccctccc ctacccttca gagatgatt  cagatggcgg cagagattgc   3540
tgacgggatg gcctacctga acgccaagaa gtttgtgcat cgggacctgg cagcgagaaa   3600
ctgcatggtc gcccatgatt ttactgtcaa aattggagac tttggaatga ccagagacat   3660
ctatgaaacg gattactacc ggaaaggggg caagggtctg ctccctgtac ggtggatggc   3720
accggagtcc ctgaaggatg gggtcttcac cacttcttct gacatgtggt cctttggcgt   3780
ggtcctttgg gaaatcacca gcttggcaga acagccttac caaggcctgt ctaatgaaca   3840
ggtgttgaaa tttgtcatgg atggagggta tctggatcaa cccgacaact gtccagagag   3900
agtcactgac ctcatgcgca tgtgctggca attcaacccc aagatgaggc caaccttcct   3960
ggagattgtc aacctgctca aggacgacct gcaccccagc tttccagagg tgtcgttctt   4020
ccacagcgag gagaacaagg ctccccgagag tgaggagctg gagatggagt ttgaggacat   4080
ggagaatgtg cccctggacc gttcctcgca ctgtcagagg gaggaggcgg ggggccggga   4140
tggagggtcc tcgctgggtt tcaagcggag ctacgaggaa cacatcccctt acacacacat   4200 gaacggaggc aagaaaaacg ggcggattct gaccttgcct cggtccaatc cttcctaaca   4260
gtgcctaccg tggcggggc  gggcagggggt tcccattttc gctttcctct ggtttgaaag   4320
cctctggaaa actcaggatt ctcacgactc taccatgtcc aatggagttc agagatcgtt   4380
cctatacatt tctgttcatc ttaaggtgga ctcgtttggt taccaattta actagtcctg   4440
cagaggattt aactgtgaac ctggagggca aggggtttcc acagttgctg ctccctttggg  4500 gcaacgacgg tttcaaacca ggatttttgt tttttttcgtt cccccacccc gcccccagca  4560
gatggaaaga aagcacctgt ttttacaaat tctttttttt tttttttttt tttgctggtg   4620
tctgagcttc agtataaaag acaaaacttc ctgtttgtgg aacaaaagtt cgaaagaaaa   4680
aacaaaacaa aaacacccag ccctgttcca ggagaatttc aagttttaca ggttgagctt   4740
caagatggtt ttttttggtt tttttttttc tctcatccag gctgaaggat ttttttttttc  4800 tttacaaaat gagttcctca aattgaccaa tagctgctgc tttcatattt tggataaggg   4860
tctgtggtcc cggcgtgtgc tcacgtgtgt atgcacgtgt gtgtgtccat tagacacggc   4920
tgatgtgtgt gcaaagtatc catgcggagt tgatgctttg ggaattggct catgaaggtt   4980
cttctcaagg gtgcgagctc atccccctct ctccttcctt cttattgact gggagactgt   5040
gctctcgaca gattcttctt gtgtcagaag tctagcctca ggtttctacc ctcccttcac   5100
attggtggcc aagggaggag catttcattt ggagtgatta tgaatctttt caagaccaaa   5160
ccaagctagg acattaaaaa aaaaaaaaga aaagaaaga  aaaacaaaa  tggaaaaagg   5220 aaaaaaaaaa agaactgaga tgacagagtt ttgagaatat atttgtacca tatttaattt   5280
ttaaagtctc tggtattagc ctcataagtt attgactatt ccccggggtt ggcggggagt   5340
ggggacatga gttggtctgc ctgttgtggg gccgggaagg ggagggagtc aggcacaagt   5400
ggcctctttg tttggtctta aaggcatcca tttctgggaa tgaagccatg ttcgctgcta   5460
```

```
acactttttgg atgttgtgag gccacgtgga gtgtgtgaga gactaggttt tatggatggt    5520
ctggttcagg taccaggtct gctggaaggt tcctgttcgg ataagctggt agctacctag    5580
ctctgagcct gccttcaaga acacctgtgt tcatcctctg attctctgtg tgtacctctt    5640
gtggcgtttc ctctcccggg tgtgaacatc ctaaccgtta ttgtgcaaac ccaagaacgt    5700
cagatcccaa agcacaacaa cctggatgga ctttgggaac atctaagcaa tgtaagagag    5760
aggtgcactg agagtacgtc ttggtcccct ccaccctgag agcatctgac ggtcctcagt    5820
actgaactcc cggaagctgc tctgagcccg gtgacctcat ctgggccagg tgtggtgcct    5880
gagctgaatg ctcaggtgct tacagtgttg caatccctaa gagagtagag tctgaggag     5940
aaaccgtgaa aaagacctta cacaccacca agaacttccg aatgggcgtg aatccaccgt    6000
ttcttctctt tgcaaaaaga accaccacag ctgctcaaag aacacagtga actcatcact    6060
ttggttcatc aaaaaatcat cgcccatgcg ttattcctga gtgcattttc ttacaacttt    6120
ttgactgctt cctttctct ttctcttaag agttgtgggc ttaagaatgg atagagtca     6180
taatggcaac ctccaagccc tctcaattct tgattaagaa cacaggtaga catgaatccc    6240
aattgtctat tgctatctta tttatatgat tcgggaaaat acagcatgta aaatattgc    6300
tgaggagcct cagtgattgg gtacaagaag caagagtaca gaaattattt ttgccaaatt    6360
tattttgtaa atatgagggt ctgtacctaa atttaaaaaa aaaacacgta gaactaggta    6420
ttttgttctc ttcttagtaa atttgtagtg gttgtatact acactagctg caattttcac    6480
attttctaa ttcagaaagg ttttttctat attaggggaa aaagtattta ttttaatata    6540
taaaatcact ctgaaaatca ctctcataaa aatggagcg catgtaaatt tttatcaaag     6600
aaaaataaac aggtgaatgg gggatagtga ttttctttt tcagcacagt ctacctcagt     6660
gtattgttaa gatgtgattc aatcatggac atctttgaga tttcagaatt ctacctggaa    6720
ccggtctgaa tcagggaacg tgtgtatcag ctgattcgaa tgccagggac cagtaagaat    6780
tttgagggag ggagttggga tggagaaggt atggccttta tgcgagcata gatccttttc    6840
ttcctggctg gtaatattct tctctgaatt taatcttcct ttaaaaaaaa atcctccatc    6900
tattgtcact atgttcccca aacataaact aagttccagg ctgtcatgat gtatctgata    6960
tatggggtaa cccagcaagg tgtaccttcc tttggtgaga gatggctgcc ggggcaaaga    7020
cgggctttga ttcagagcaa gcattccac ctgttccatg gaatccccct gaagtgagca    7080
caaaggtgcc ctgggctccc tgatggttta tgcccactcc tttcaggctg gtgatgcacc    7140
ttacacacaa acacctaatg caatgtcttt ttaaattctc caagtgggat gggagcatgt    7200
gagggaaatt ccaatccaaa acccattaat gtgctgaacg cttttttttt tttttttttt    7260
tttttgcaa caacaccttg gacctctgtg ttggggtttg actgacctca agctgatatt    7320
attggacctt gtgcagcttt gataacccat gtgagagtct aggcaggacc agtggggccc    7380
aaatcttgct gctcttgtac ttttaggcac tgcccttgca gactcacctt tctccacctg    7440
ccctggagaa aggtagggtg tgctgggcct gccccttgca aatgggattc accagtttca    7500
tttatttgac tctactgcca cagtgaaaag agcaaacagc tattgggttg caaacctcct    7560
ttgacattag gaaatgttga ctttgtaaca ataaaacttt ggtcctagaa agacacggtt    7620
gtcctgggag tttgtagtgt taagttgcaa caacaacaac aaaaagcaac aaaaccagct    7680
taggataaca ctttttgttg cttgttctta aagatgtctc actatgatta aaacccttt     7740
cattaatgta gtgaaagcca cacaggagtt ccttcttcca ggaggagaat accaagcaca    7800
tcactttctc tctgcatcag tgatgtcaaa tacgcatcag aaaatgttca ggttttagga    7860
```

```
gctgtcctag gtgctgtttc atcattggaa gcagtgagaa agagaagcac tgctgcttgt    7920
ctggatatat gctgaggatg attgagagaa gctgtggaa ctgacacaag ggtctgcata     7980
ggtcatcctg tgaccctggg gactatgtta ccaactgaca gacagatctt tcactgtatc    8040
ctagcagggc aggtagtcca ccaagaaatg tgcttattgg attgggaggt gtttatttgt    8100
agtctgctgt aacacgtgtg aaagagcagg agcgtcatca gcatatgact tgcgctggtc    8160
atccggtaaa tggatgtgct gtagtcccag tgctaatcat ttctctcctt cacagtgggt    8220
ggaagtttag ggttaaatgt cctttgaatg tcacctggtg agtccttgac accttaggct    8280
cttcagaaac aatggttttg ttgaggatgg ggaacaggga atgccgattt tatatacatg    8340
gtacacagag aggggtgtca cttcagaaaa tcttccagca tgttcttcag aatattaatt    8400
tatatgcgag gtgaggttgg gaatgaaaag aacaggtcag cacttttttt tttcctagaa    8460
catacaaaag aacatggtgg actttcaggg agtgcaatgg aaggtgaata tttccttaag    8520
ggtccccgag aaatgggagt gaggggaggg gacacaatgg cttttgagc ttacttttac     8580 cttctgatac tagtcaaggt ccagaaccag ccaccagcca aatttctatc tgggtgcggg    8640
ccactgaaaa tccttgttaa aaccagatc acaaatctgg ggctcttggt cccattggag     8700
aaggaaggaa gagcctcaaa ataagtgtgc acccatgcac atattcagga acagcttgtt    8760
tagtctttac actttgcctg aaagttgctt ctcctcgtcc ctttgtgtgc ctgggtggcc    8820
tcggccctgt gcgttggcaa cgcaggatca aatgtgctgc agcttttgca gaaaacaact    8880
cagaaacaca aaaccccccca acagctcaat tattatttt tcaatgtttt cctacaagag    8940
ccaagtagca ccatgtacag aagacgcctt ttttttttgga atattgaaat cgttctgcat    9000
gtaaaatatg ggataatgac ctgtttatat taaaattctg attaaattat ctgagaata    9059

<210> SEQ ID NO 44
<211> LENGTH: 9023
<212> TYPE: DNA
<213> ORGANISM: human

<400> SEQUENCE: 44
gagaaggacg cgcggccccc agcgcctctt gggtggccgc ctcggagcat gaccccgcg      60 ggccagcgcc gcgcgctctg atccgaggag accccgcgct cccgcagcca tggccaccgg    120
gggccggcgg ggggcggcgg ccgcgccgct gctggtggcg gtggccgcgc tgctactggg    180
cgccgcgggc cacctgtacc ccggagaggt gtgtccggc atggatatcc ggaacaacct    240
cactaggttg catgagctgg agaattgctc tgtcatcgaa ggacacttgc agatactctt    300
gatgttcaaa acgaggcccg aagatttccg agacctcagt ttccccaaac tcatcatgat    360
cactgattac ttgctgctct tccgggtcta tgggctcgag agcctgaagg acctgttccc    420
caacctcacg gtcatccggg gatcacgact gttctttaac tacgcgctgg tcatcttcga    480
gatggttcac ctcaaggaac tcggcctcta caacctgatg aacatcaccc gggttctgt    540 ccgcatcgag aagaacaatg agctctgtta cttggccact atcgactggt cccgtatcct    600
ggattccgtg gaggataatt acatcgtgtt gaacaaagat gacaacgagg agtgtggaga    660
catctgtccg ggtaccgcga agggcaagac caactgcccc gccaccgtca tcaacgggca    720
gtttgtcgaa cgatgttgga ctcatagtca ctgccagaaa gtttgcccga ccatctgtaa    780
gtcacacggc tgcaccgccg aaggcctctg ttgccacagc gagtgcctgg gcaactgttc    840
tcagcccgac gaccccacca agtgcgtggc ctgccgcaac ttctacctgg acggcaggtg    900
```

```
tgtggagacc tgcccgcccc cgtactacca cttccaggac tggcgctgtg tgaacttcag    960
cttctgccag gacctgcacc acaaatgcaa gaactcgcgg aggcagggct gccaccagta   1020
cgtcattcac aacaacaagt gcatccctga gtgtccctcc gggtacacga tgaattccag   1080
caacttgctg tgcaccccat gcctgggtcc ctgtcccaag gtgtgccacc tcctagaagg   1140
cgagaagacc atcgactcgg tgacgtctgc ccaggagctc cgaggatgca ccgtcatcaa   1200
cgggagtctg atcatcaaca ttcgaggagg caacaatctg gcagctgagc tagaagccaa   1260
cctcggcctc attgaagaaa tttcagggta tctaaaaatc cgccgatcct acgctctggt   1320
gtcactttcc ttcttccgga agttacgtct gattcgagga gagaccttgg aaattgggaa   1380
ctactccttc tatgccttgg acaaccagaa cctaaggcag ctctgggact ggagcaaaca   1440
caacctcacc atcactcagg ggaaaactct tcttccactat aaccccaaac tctgcttgtc   1500
agaaatccac aagatggaag aagtttcagg aaccaagggg cgccaggaga gaaacgacat   1560
tgccctgaag accaatgggg accaggcatc ctgtgaaaat gagttactta aattttctta   1620
cattcggaca tcttttgaca agatcttgct gagatgggag ccgtactggc cccccgactt   1680
ccgagacctc ttggggttca tgctgttcta caaagaggcc cttatcaga atgtgacgga   1740
gttcgacggg caggatgcgt gtggttccaa cagttggacg tggtagaca ttgacccacc   1800
cctgaggtcc aacgacccca aatcacagaa ccacccaggg tggctgatgc ggggtctcaa   1860
gccctggacc agtatgccca tctttgtgaa gaccctggtc accttttcgg atgaacgccg   1920
gacctatggg gccaagagtg acatcattta tgtccagaca gatgccacca cccctctgt   1980
gccctggat ccaatctcag tgtctaactc atcatcccag attattctga agtggaaacc   2040
accctccgac cccaatggca acatcaccca ctacctggtt ttctgggaga ggcaggcgga   2100
agacagtgag ctgttcgagc tggattattg cctcaaaggg ctgaagctgc cctcgaggac   2160
ctggtctcca ccattcgagt ctgaagattc tcagaagcac aaccagagtg agtatgagga   2220
ttcggccggc gaatgctgct cctgtccaaa gacagactct cagatcctga aggagctgga   2280
ggagtcctcg tttaggaaga cgtttgagga ttacctgcac aacgtggttt tcgtccccag   2340
gccatctcgg aaacgcaggt cccttggcga tgttgggaat gtgacggtgg ccgtgcccac   2400
ggtggcagct ttccccaaca cttcctcgac cagcgtgccc acgagtccgg aggagcacag   2460
gccttttgag aaggtggtga caaggagtc gctggtcatc tccggcttgc gacacttcac   2520
gggctatcgc atcgagctgc aggcttgcaa ccaggacacc cctgaggaac ggtgcagtgt   2580
ggcagcctac gtcagtgcga ggaccatgcc tgaagccaag gctgatgaca ttgttggccc   2640
tgtgacgcat gaaatctttg agaacaacgt cgtccacttg atgtggcagg agccgaagga   2700
gcccaatggt ctgatcgtgc tgtatgaagt gagttatcgg cgatatggtg atgaggagct   2760
gcatctctgc gtctcccgca agcacttcgc tctggaacgg ggctgcaggc tgcgtgggct   2820
gtcaccgggg aactacagcg tgcgaatccg ggccacctcc cttgcgggca cggctcttg   2880
gacggaaccc acctatttct acgtgacaga ctatttagac gtcccgtcaa atattgcaaa   2940
aattatcatc ggcccctca tctttgtctt tctcttcagt gttgtgattg aagtatttta   3000
tctattcctg agaaagaggc agccagatgg gccgctggga ccgctttacg cttcttcaaa   3060
ccctgagtat ctcagtgcca gtgatgtgtt tccatgctct gtgtacgtgc cggacagagtg   3120
ggaggtgtct cgagagaaga tcaccctcct tcgagagctg gggcagggct ccttcggcat   3180
ggtgtatgag ggcaatgcca gggacatcat caagggtgag gcagagaccc gcgtggcggt   3240
gaagacggtc aacgagtcag ccagtctccg agagcggatt gagttcctca atgaggcctc   3300
```

```
ggtcatgaag ggcttcacct gccatcacgt ggtgcgcctc ctgggagtgg tgtccaaggg    3360
ccagcccacg ctggtggtga tggagctgat ggctcacgga gacctgaaga gctacctccg    3420
ttctctgcgg ccagaggctg agaataatcc tggccgccct cccctaccc ttcaagagat     3480
gattcagatg gcggcagaga ttgctgacgg gatggcctac ctgaacgcca agaagtttgt    3540
gcatcgggac ctggcagcga gaaactgcat ggtcgcccat gattttactg tcaaaattgg    3600
agactttgga atgaccagag acatctatga acggattac taccggaaag ggggcaaggg     3660
tctgctccct gtacggtgga tggcaccgga gtccctgaag gatggggtct caccacttc     3720
ttctgacatg tggtcctttg gcgtggtcct ttgggaaatc accagcttgg cagaacagcc    3780
ttaccaaggc ctgtctaatg aacaggtgtt gaaatttgtc atggatggag gtatctgga    3840
tcaacccgac aactgtccag agagagtcac tgacctcatg cgcatgtgct ggcaattcaa    3900
ccccaagatg aggccaacct tcctggagat tgtcaacctg ctcaaggacg acctgcaccc    3960
cagctttcca gaggtgtcgt tcttccacag cgaggagaac aaggctcccg agagtgagga    4020
gctggagatg gagtttgagg acatggagaa tgtgccctg accgttcct cgcactgtca      4080
gagggaggag gcgggggcc gggatggagg gtcctcgctg ggtttcaagc ggagctacga     4140
ggaacacatc ccttacacac acatgaacgg aggcaagaaa aacgggcgga ttctgacctt    4200
gcctcggtcc aatccttcct aacagtgcct accgtggcgg gggcgggcag gggttcccat    4260
tttcgctttc ctctggtttg aaagcctctg gaaaactcag gattctcacg actctaccat    4320
gtccaatgga gttcagagat cgttcctata catttctgtt catcttaagg tggactcgtt    4380
tggttaccaa tttaactagt cctgcagagg atttaactgt gaacctggag ggcaagggt     4440
ttccacagtt gctgctcctt tggggcaacg acgtttcaa accaggattt tgtgttttt     4500
cgttccccc acccgccccc agcagatgga agaaagcac ctgttttac aaattcttt       4560
tttttttt ttttttgct ggtgtctgag cttcagtata aagacaaaa cttcctgttt        4620
gtggaacaaa agttcgaaag aaaaacaaa acaaaacac ccagccctgt tccaggagaa      4680
tttcaagttt tacaggttga gcttcaagat ggttttttg gtttttttt tttctctcat     4740
ccaggctgaa ggattttttt tttctttaca aaatgagttc ctcaaattga ccaatagctg    4800
ctgctttcat attttggata agggtctgtg gtcccggcgt gtgctcacgt gtgtatgcac    4860
gtgtgtgtgt ccattagaca cggctgatgt gtgtgcaaag tatccatgcg gagttgatgc    4920
tttgggaatt ggctcatgaa ggttcttctc aagggtgcga gctcatcccc ctctctcctt    4980
ccttcttatt gactgggaga ctgtgctctc gacagattct tcttgtgtca gaagtctagc    5040
ctcaggtttc taccctccct tcacattggt ggccaaggga ggagcatttc atttggagtg    5100
attatgaatc ttttcaagac caaaccaagc taggacatta aaaaaaaaa aagaaaaga     5160
aagaaaaaac aaaatggaaa aaggaaaaaa aaaagaact gagatgacag agttttgaga    5220
atatattgt accatattta attttaaag tctctggtat tagcctcata agttattgac     5280
tattccccgg ggttggcggg gagtggggac atgagttggt ctgcctgttg tggggccggg    5340
aaggggaggg agtcaggcac aagtggcctc tttgtttggt cttaaaggca tccatttctg    5400
ggaatgaagc catgttcgct gctaacactt ttggatgttg tgaggccacg tggagtgtgt    5460
gagagactag gttttatgga tggtctggtt caggtaccag gtctgctgga aggttcctgt    5520
tcggataagc tggtagctac ctagctctga gcctgccttc aagaacacct gtgttcatcc    5580
tctgattctc tgtgtgtacc tcttgtggcg tttcctctcc cgggtgtgaa catcctaacc    5640
```

```
gttattgtgc aaacccaaga acgtcagatc ccaaagcaca acaacctgga tggactttgg    5700
gaacatctaa gcaatgtaag agagaggtgc actgagagta cgtcttggtc ccctccaccc    5760
tgagagcatc tgacggtcct cagtactgaa ctcccggaag ctgctctgag cccggtgacc    5820
tcatctgggc caggtgtggt gcctgagctg aatgctcagg tgcttacagt gttgcaatcc    5880
ctaagagagt agagtctgga ggagaaaccg tgaaaagac cttacacacc accaagaact     5940
tccgaatggg cgtgaatcca ccgtttcttc tctttgcaaa aagaaccacc acagctgctc    6000
aaagaacaca gtgaactcat cactttggtt catcaaaaaa tcatcgccca tgcgttattc    6060
ctgagtgcat tttcttacaa cttttttgact gcttcctttt cttcttctct taagagttgt   6120
gggcttaaga atgggataga gtcataatgg caacctccaa gccctctcaa ttcttgatta    6180
agaacacagg tagacatgaa tcccaattgt ctattgctat cttatttata tgattcggga    6240
aaatacagca tgtaaaaata ttgctgagga gcctcagtga ttgggtacaa gaagcaagag    6300
tacagaaatt attttttgcca aatttatttt gtaaatatga gggtctgtac ctaaatttaa    6360
aaaaaaaaca cgtagaacta ggtattttgt tctcttctta gtaaatttgt agtggttgta    6420
tactacacta gctgcaattt tcacatttt ctaattcaga aaggttttc ttatattagg       6480 ggaaaaagta tttattttaa tatataaaat cactctgaaa atcactctca taaaaaatgg    6540
agcgcatgta aattttttatc aaagaaaaat aaacaggtga atgggggata gtgattttct   6600 ttttttcagca cagtctacct cagtgtattg ttaagatgtg attcaatcat ggacatcttt   6660
gagatttcag aattctacct ggaaccggtc tgaatcaggg aacgtgtgta tcagctgatt    6720
cgaatgccag ggaccagtaa gaattttgag ggagggagtt gggatggaga aggtatggcc    6780
tttatgcgag catagatcct tttcttcctg gctggtaata ttcttctctg aatttaatct    6840 tccttttaaaa aaaaatcctc catctattgt cactatgttc cccaaacata aactaagttc   6900
caggctgtca tgatgtatct gatatatggg gtaacccagc aaggtgtacc ttccttttggt  6960 gagagatggc tgccggggca agacgggct ttgattcaga gcaagcattc ccacctgttc     7020
catggaatcc ccctgaagtg agcacaaagg tgccctgggc tccctgatgg tttatgccca    7080
ctcctttcag gctggtgatg caccttacac acaaacacct aatgcaatgt cttttttaaat   7140 tctccaagtg ggatgggagc atgtgaggga aattccaatc caaaacccat taatgtgctg    7200
aacgcttttt ttttttttttt tttttttttt gcaacaacac cttggacctc tgtgttgggg   7260
tttgactgac ctcaagctga tattattgga ccttgtgcag ctttgataac ccatgtgaga    7320
gtctaggcag gaccagtggg gcccaaatct tgctgctctt gtacttttag gcactgccct    7380
tgcagactca ccttctcca cctgccctgg agaaggtag ggtgtgctgg gcctgcccct      7440
tgcaaatggg attcaccagt ttcatttatt tgactctact gccacagtga aaagagcaaa    7500
cagctattgg gttgcaaacc tccttttgaca ttaggaaatg ttgactttgt aacaataaaa   7560
ctttggtcct agaaagacac ggttgtcctg ggagtttgta gtgttaagtt gcaacaacaa    7620
caacaaaaag caacaaaacc agcttaggat aacactttt gttgcttgtt cttaaagatg     7680
tctcactatg attaaaaccc ttttcattaa tgtagtgaaa gccacacagg agttccttct    7740
tccaggagga gaataccaag cacatcactt tctctctgca tcagtgatgt caaatacgca    7800
tcagaaaatg ttcaggtttt aggagctgtc ctaggtgctg tttcatcatt ggaagcagtg    7860
agaaagagaa gcactgctgc ttgtctggat ataggctgag gatgattgag agaagctgtg    7920
ggaactgaca caagggtctg cataggtcat cctgtgaccc tggggactat gttaccaact    7980
gacagacaga tctttcactg tatcctagca gggcaggtag tccaccaaga aatgtgctta    8040
```

```
ttggattggg aggtgtttat ttgtagtctg ctgtaacacg tgtgaaagag caggagcgtc    8100
atcagcatat gacttgcgct ggtcatccgg taaatggatg tgctgtagtc ccagtgctaa    8160
tcatttctct ccttcacagt gggtggaagt ttagggttaa atgtcctttg aatgtcacct    8220
ggtgagtcct tgacacctta ggctcttcag aaacaatggt tttgttgagg atggggaaca    8280
gggaatgccg attttatata catggtacac agagaggggt gtcacttcag aaaatcttcc    8340
agcatgttct tcagaatatt aatttatatg cgaggtgagg ttgggaatga aaagaacagg    8400
tcagcacttt ttttttttcct agaacataca aaagaacatg gtggactttc agggagtgca    8460
atggaaggtg aatatttcct taagggtccc cgagaaatgg gagtgagggg aggggacaca    8520
atggcttttt gagcttactt ttaccttctg atactagtca aggtccagaa ccagccacca    8580
gccaaatttc tatctgggtg cgggccactg aaaatccttg ttaaaaacca gatcacaaat    8640
ctggggctct tggtcccatt ggagaaggaa ggaagagcct caaaataagt gtgcacccat    8700
gcacatattc aggaacagct tgtttagtct ttacactttg cctgaaagtt gcttctcctc    8760 gtcccttttgt gtgcctgggt ggcctcggcc ctgtgcgttg gcaacgcagg atcaaatgtg    8820
ctgcagcttt tgcagaaaac aactcagaaa cacaaaaccc cccaacagct caattattat    8880
tttttcaatg ttttcctaca agagccaagt agcaccatgt acagaagacg ccttttttt    8940 tggaatattg aaatcgttct gcatgtaaaa tatgggataa tgacctgttt atattaaaat    9000
tctgattaaa ttatctgaga ata                                           9023

<210> SEQ ID NO 45
<211> LENGTH: 4742
<212> TYPE: DNA
<213> ORGANISM: human

<400> SEQUENCE: 45
ttttctgccc ttctttgctt tggtggcttc cttgtggttc ctcagtggtg cctgcaaccc      60
ctggttcacc tccttccagg ttctggctcc ttccagccat ggctctcaga gtccttctgt     120
taacagcctt gacctatgt catgggttca acttggacac tgaaaacgca atgaccttcc     180
aagagaacgc aaggggcttc gggcagagcg tggtccagct tcagggatcc agggtggtgg     240
ttggagcccc ccaggagata gtggctgcca accaaggggg cagcctctac cagtgcgact     300
acagcacagg ctcatgcgag cccatccgcc tgcaggtccc cgtggaggcc gtgaacatgt     360
ccctgggcct gtccctggca gccaccacca gccccctca gctgctggcc tgtggtccca     420
ccgtgcacca gacttgcagt gagaacacgt atgtgaaagg gctctgcttc ctgtttggat     480
ccaacctacg gcagcagccc cagaagttcc cagaggccct ccgagggtgt cctcaagagg     540
atagtgacat tgccttcttg attgatggct ctggtagcat catcccacat gactttcggc     600
ggatgaagga gtttgtctca actgtgatgg agcaattaaa aaagtccaaa accttgttct     660
ctttgatgca gtactctgaa gaattccgga ttcactttac cttcaaagag ttccagaaca    720 acccctaaccc aagatcactg gtgaagccaa taacgcagct gcttgggcgg acacacacgg    780
ccacgggcat ccgcaaagtg gtacgagagc tgtttaacat caccaacgga gcccgaaaga    840
atgcctttaa gatcctagtt gtcatcacgg atggagaaaa gtttggcgat cccttgggat    900
atgaggatgt catccctgag gcagacagag agggagtcat tcgctacgtc attggggtgg    960
gagatgcctt ccgcagtgag aaatcccgcc aagagcttaa taccatcgca tccaagccgc    1020
ctcgtgatca cgtgttccag gtgaataact ttgaggctct gaagaccatt cagaaccagc    1080
```

```
ttcgggagaa gatctttgcg atcgagggta ctcagacagg aagtagcagc tcctttgagc    1140
atgagatgtc tcaggaaggc ttcagcgctg ccatcacctc taatggcccc ttgctgagca    1200
ctgtggggag ctatgactgg gctggtggag tctttctata tacatcaaag gagaaaagca    1260
ccttcatcaa catgaccaga gtggattcag acatgaatga tgcttacttg ggttatgctg    1320
ccgccatcat cttacggaac cgggtgcaaa gcctggttct gggggcacct cgatatcagc    1380
acatcggcct ggtagcgatg ttcaggcaga acactggcat gtgggagtcc aacgctaatg    1440
tcaagggcac ccagatcggc gcctacttcg gggcctccct ctgctccgtg gacgtggaca    1500
gcaacgcag caccgacctg gtcctcatcg ggccccccca ttactacgag cagacccgag    1560
ggggccaggt gtccgtgtgc cccttgccca gggggagggc tcggtggcag tgtgatgctg    1620
ttctctacgg ggagcagggc caaccctggg gccgctttgg ggcagcccta acagtgctgg    1680
gggacgtaaa tggggacaag ctgacggacg tggccattgg ggccccagga gaggaggaca    1740
accggggtgc tgtttacctg tttcacggaa cctcaggatc tggcatcagc ccctcccata    1800
gccagcggat agcaggctcc aagctctctc ccaggctcca gtattttggt cagtcactga    1860
gtgggggcca ggacctcaca atggatggac tggtagacct gactgtagga gcccaggggc    1920
acgtgctgct gctcaggtcc cagccagtac tgagagtcaa ggcaatcatg gagttcaatc    1980
ccagggaagt ggcaaggaat gtatttgagt gtaatgatca ggtggtgaaa ggcaaggaag    2040
ccggagaggt cagagtctgc ctccatgtcc agaagagcac acgggatcgg ctaagagaag    2100
gacagatcca gagtgttgtg acttatgacc tggctctgga ctccggccgc ccacattccc    2160
gcgccgtctt caatgagaca aagaacagca cacgcagaca gacacaggtc ttggggctga    2220
cccagacttg tgagaccctg aaactacagt tgccgaattg catcgaggac ccagtgagcc    2280
ccattgtgct gcgcctgaac ttctctctgg tgggaacgcc attgtctgct ttcgggaacc    2340
tccggccagt gctggcggag gatgctcaga gactcttcac agccttgttt cccttgaga    2400
agaattgtgg caatgacaac atctgccagg atgacctcag catcaccttc agtttcatga    2460
gcctggactg cctcgtggtg ggtgggcccc gggagttcaa cgtgacagtg actgtgagaa    2520
atgatggtga ggactcctac aggacacagg tcaccttctt cttcccgctt gacctgtcct    2580
accggaaggt gtccacgctc cagaaccagc gctcacagcg atcctggcgc ctggcctgtg    2640
agtctgcctc ctccaccgaa gtgtctgggg ccttgaagag caccagctgc agcataaacc    2700
accccatctt cccggaaaac tcagaggtca cctttaatat cacgtttgat gtagactcta    2760
aggcttccct tggaaacaaa ctgctcctca aggccaatgt gaccagtgag aacaacatgc    2820
ccagaaccaa caaaccgaa ttccaactgg agctgccggt gaaatatgct gtctacatgg    2880
tggtcaccag ccatgggtc tccactaaat atctcaactt cacggcctca gagaatacca    2940
gtcgggtcat gcagcatcaa tatcaggtca gcaacctggg gcagaggagc ctccccatca    3000
gcctggtgtt cttggtgccc gtccggctga accagactgt catatgggac cgcccccagg    3060
tcaccttctc cgagaacctc tcgagtacgt gccacaccaa ggagcgcttg ccctctcact    3120
ccgactttct ggctgagctt cggaaggccc ccgtggtgaa ctgctccatc gctgtctgcc    3180
agagaatcca gtgtgacatc ccgttctttg gcatccagga agaattcaat gctaccctca    3240
aaggcaacct ctcgtttgac tggtacatca agacctcgca taaccacctc ctgatcgtga    3300
gcacagctga gatcttgttt aacgattccg tgttcaccct gctgccggga caggggcgt    3360
ttgtgaggtc ccagacggag accaaagtgg agccgttcga ggtccccaac cccctgccgc    3420
tcatcgtggg cagctctgtc gggggactgc tgctcctggc cctcatcacc gccgcgctgt    3480
```

```
acaagctcgg cttcttcaag cggcaataca aggacatgat gagtgaaggg ggtcccccgg   3540
gggccgaacc ccagtagcgg ctccttcccg acagagctgc ctctcggtgg ccagcaggac   3600
tctgcccaga ccacacgtag cccccaggct gctggacacg tcggacagcg aagtatcccc   3660
gacaggacgg gcttgggctt ccatttgtgt gtgtgcaagt gtgtatgtgc gtgtgtgcaa   3720
gtgtctgtgt gcaagtgtgt gcacatgtgt gcgtgtgcgt gcatgtgcac ttgcacgccc   3780
atgtgtgagt gtgtgcaagt atgtgagtgt gtccaagtgt gtgtgcgtgt gtccatgtgt   3840
gtgcaagtgt gtgcatgtgt gcgagtgtgt gcatgtgtgt gctcaggggc gtgtggctca   3900
cgtgtgtgac tcagatgtct ctggcgtgtg ggtaggtgac ggcagcgtag cctctccggc   3960
agaagggaac tgcctgggct cccttgtgcg tgggtgaagc cgctgctggg ttttcctccg   4020
ggagagggga cggtcaatcc tgtgggtgaa gacagaggga aacacagcag cttctctcca   4080
ctgaaagaag tgggacttcc cgtcgcctgc gagcctgcgg cctgctggag cctgcgcagc   4140
ttggatggga actccatgag aagccgtggg tggaaccagg aacctcctcc acaccagcgc   4200
tgatgcccaa taaagatgcc cactgaggaa tgatgaagct tcctttctgg attcatttat   4260
tatttcaatg tgactttaat tttttggatg gataagcttg tctatggtac aaaaatcaca   4320
aggcattcaa gtgtacagtg aaaagtctcc ctttccagat attcaagtca cctccttaaa   4380
ggtagtcaag attgtgtttt gaggtttcct tcagacagat tccaggcgat gtgcaagtgt   4440
atgcacgtgt gcacacacac cacacataca cacacacaag cttttttaca caaatggtag   4500
catactttat attggtctgt atcttgcttt ttttcaccaa tatttctcag acatcggttc   4560
atattaagac ataaattact ttttcattct tttataccgc tgcatagtat tccattgtgt   4620
gagtgtacca taatgtattt aaccagtctt cttttgatat actattttca ttctcttgtt   4680
attgcatcaa tgctgagtta ataaatcaaa tatatgtcat ttttgcatat atgtaaggat   4740
aa                                                                 4742

<210> SEQ ID NO 46
<211> LENGTH: 12625
<212> TYPE: DNA
<213> ORGANISM: human

<400> SEQUENCE: 46
gctgtcccca agccgattgg tacttcttgt caggaagaaa cgccaagagg tgggagtgcc     60
tggggaggga ggcaggcggt ccctaccgca ggcgcgggga gctgcctttc cgcccctccg    120
cctgctttcc aagcctggac tcttaggagt ggctgaagct gcggagcgct tttgagcct    180
gtgaatgaac cctcctcctc tccctcctcc ttcttctcgc tgagtctcct cctcggctct    240
gacggtacag tgatataatg atgatgggtg tcacaacccg catttgaact tgcaggcgag    300
ctgccccgag ccttctcggg gaagaactcc aggcgtgcgg acgcaacagc cgagaacatt    360
aggtgttgtg gacaggagct gggaccaaga tcttcggcca gccccgcatc ctcccgcatc    420
ttccagcacc gtcccgcacc ctccgcatcc ttccccgggc caccacgctt cctatgtgac    480
ccgcctgggc aacgccgaac ccagtcgcgc agcgctgcag tgaattttcc ccccaaactg    540
caataagccg ccttccaagg ccaagatgtt cataaatata aagagcatct tatggatgtg    600
ttcaacctta atagtaaccc atgcgctaca taaagtcaaa gtgggaaaaa gcccaccggt    660
gaggggctcc ctctctggaa aagtcagcct accttgtcat ttttcaacga tgcctacttt    720
gccacccagt tacaacacca gtgaatttct ccgcatcaaa tggtctaaga ttgaagtgga    780
```

```
caaaaatgga aaagatttga aagagactac tgtccttgtg gcccaaaatg gaaatatcaa    840
gattggtcag gactacaaag ggagagtgtc tgtgcccaca catcccgagg ctgtgggcga    900
tgcctccctc actgtggtca agctgctggc aagtgatgcg ggtctttacc gctgtgacgt    960
catgtacggg attgaagaca cacaagacac ggtgtcactg actgtggatg gggttgtgtt   1020
tcactacagg gcggcaacca gcaggtacac actgaatttt gaggctgctc agaaggcttg   1080
tttggacgtt ggggcagtca tagcaactcc agagcagctc tttgctgcct atgaagatgg   1140
atttgagcag tgtgacgcag gctggctggc tgatcagact gtcagatatc ccatccgggc   1200
tcccagagta ggctgttatg gagataagat gggaaaggca ggagtcagga cttatggatt   1260
ccgttctccc caggaaactt acgatgtgta ttgttatgtg gatcatctgg atggtgatgt   1320
gttccacctc actgtcccca gtaaattcac cttcgaggag ctgcaaaag agtgtgaaaa   1380
ccaggatgcc aggctggcaa cagtggggga actccaggcg gcatggagga acggctttga   1440
ccagtgcgat tacgggtggc tgtcggatgc cagcgtgcgc caccctgtga ctgtggccag   1500
ggcccagtgt ggaggtggtc tacttggggt gagaaccctg tatcgttttg agaaccagac   1560
aggcttccct cccccctgata gcagatttga tgcctactgc tttaaaccta agaggctac   1620
aaccatcgat ttgagtatcc tcgcagaaac tgcatcaccc agtttatcca agaaccaca   1680
aatggtttct gatagaacta caccaatcat cccttagtt gatgaattac ctgtcattcc    1740
aacagagttc cctcccgtgg gaaatattgt cagttttgaa cagaaagcca cagtccaacc   1800
tcaggctatc acagatagtt tagccaccaa attacccaca cctactggca gtaccaagaa   1860
gccctgggat atggatgact actcaccttc tgcttcagga cctcttggaa agctagacat   1920
atcagaaatt aaggaagaag tgctccagag tacaactggc gtctctcatt atgctacgga   1980
ttcatgggat ggtgtcgtgg aagataaaca aacacaagaa tcggttacac agattgaaca   2040
aatagaagtg ggtccttttgg taacatctat ggaaatctta aagcacattc cttccaagga   2100
attccctgta actgaaacac cattggtaac tgcaagaatg atcctggaat ccaaaactga   2160
aaagaaaatg gtaagcactg tttctgaatt ggtaaccaca ggtcactatg gattcacctt   2220
gggagaagag gatgatgaag acagaacact tacagttgga tctgatgaga gcaccttgat   2280
ctttgaccaa attcctgaag tcattacggt gtcaaagact tcagaagaca ccatccacac   2340
tcatttagaa gacttggagt cagtctcagc atccacaact gtttccccctt taattatgcc   2400
tgataataat ggatcatcca tggatgactg ggaagagaga caaactagtg gtaggataac   2460
ggaagagttt cttggcaaat atctgtctac tacacctttt ccatcacagc atcgtacaga   2520
aatagaattg tttccttatt ctggtgataa atattagta gagggaattt ccacagttat   2580
ttatccttct ctacaaacag aaatgacaca tagaagagaa agaacagaaa cactaatacc   2640
agagatgaga acagatactt atacagatga aatacaagaa gagatcacta aaagtccatt   2700
tatgggaaaa acagaagaag aagtcttctc tgggatgaaa ctctctacat ctctctcaga   2760
gccaattcat gttacagagt cttctgtgga aatgaccaag tcttttgatt tcccaacatt   2820
gataacaaag ttaagtgcag agccaacaga agtaagagat atggaggaag actttacagc   2880
aactccaggt actacaaaat atgatgaaaa tattacaaca gtgcttttgg cccatggtac   2940
tttaagtgtt gaagcagcca ctgtatcaaa atggtcatgg gatgaagata atacaacatc   3000
caagccttta gagtctacag aaccttcagc ctcttcaaaa ttgccccctg ccttactcac   3060
aactgtgggg atgaatggaa aggataaaga catcccaagt ttcactgaag atggagcaga   3120
tgaatttact cttattccag atagtactca aaagcagtta gaggaggtta ctgatgaaga   3180
```

```
catagcagcc catggaaaat tcacaattag atttcagcca actacatcaa ctggtattgc    3240
agaaaagtca actttgagag attctacaac tgaagaaaaa gttccaccta tcacaagcac    3300
tgaaggccaa gtttatgcaa ccatggaagg aagtgctttg ggtgaagtag aagatgtgga    3360
cctctctaag ccagtatcta ctgttcccca atttgcacac acttcagagg tggaaggatt    3420
agcatttgtt agttatagta gcacccaaga gcctactact tatgtagact cttcccatac    3480
cattcctctt tctgtaattc ccaagacaga ctggggagtg ttagtacctt ctgttccatc    3540
agaagatgaa gttctaggtg aaccctctca agacatactt gtcattgatc agactcgcct    3600
tgaagcgact atttctccag aaactatgag aacaacaaaa atcacagagg gaacaactca    3660
ggaagaattc ccttggaaag aacagactgc agagaaacca gttcctgctc tcagttctac    3720
agcttggact cccaaggagg cagtaacacc actggatgaa caagagggcg atggatcagc    3780
atatacagtc tctgaagatg aattgttgac aggttctgag agggtcccag ttttagaaac    3840
aactccagtt ggaaaaattg atcacagtgt gtcttatcca ccaggtgctg taactgagca    3900
caaagtgaaa acagatgaag tggtaacact aacaccacgc attgggccaa agtatctttt    3960
aagtccaggg cctgaacaaa aatatgaaac agaaggtagt agtacaacag gatttacatc    4020
atctttgagt ccttttagta cccacattac ccagcttatg gaagaaacca ctactgagaa    4080
aacatcccta gaggatattg atttaggctc aggattattt gaaaagccca agccacaga    4140 actcatagaa ttttcaacaa tcaaagtcac agttccaagt gatattacca ctgccttcag    4200
ttcagtagac agacttcaca caacttcagc attcaagcca tcttccgcga tcactaagaa    4260
accacctctc atcgacaggg aacctggtga agaaacaacc agtgacatgg taatcattgg    4320
agaatcaaca tctcatgttc ctcccactac ccttgaagat attgtagcca aggaaacaga    4380
aaccgatatt gatagagagt atttcacgac ttcaagtcct cctgctacac agccaacaag    4440
accacccact gtggaagaca agaggcctt tggacctcag gcgctttcta cgccacagcc    4500
cccagcaagc acaaaatttc accctgacat taatgtttat attattgagg tcagagaaaa    4560
taagacaggt cgaatgagtg atttgagtgt aattggtcat ccaatagatt cagaatctaa    4620
agaagatgaa ccttgtagtg aagaaacaga tccagtgcat gatctaatgg ctgaaatttt    4680
acctgaattc cctgacataa ttgaaataga cctataccac agtgaagaaa atgaagaaga    4740
agaagaagag tgtgcaaatg ctactgatgt gacaaccacc ccatctgtgc agtacataaa    4800
tgggaagcat ctcgttacca ctgtgcccaa ggacccagaa gctgcagaag ctaggcgtgg    4860
ccagtttgaa agtgttgcac cttctcagaa ttttcggac agctctgaaa gtgatactca    4920
tccatttgta atagccaaaa cggaattgtc tactgctgtg caacctaatg aatctacaga    4980
aacaactgag tctcttgaag ttacatggaa gcctgagact accctgaaa catcagaaca    5040 tttttcaggt ggtgagcctg atgttttccc cacagtccca ttccatgagg aatttgaaag    5100
tggaacagcc aaaaaggggg cagaatcagt cacagagaga gatactgaag ttggtcatca    5160
ggcacatgaa catactgaac ctgtatctct gtttcctgaa gagtcttcag agagattgc    5220 cattgaccaa gaatctcaga aaatagcctt tgcaagggct acagaagtaa catttggtga    5280
agaggtagaa aaaagtactt ctgtcacata cactcccact atagttccaa gttctgcatc    5340
agcatatgtt tcagaggaag aagcagttac cctaatagga aatccttggc cagatgacct    5400
gttgtctacc aaagaaagct gggtagaagc aactcctaga caagttgtag agctctcagg    5460
gagttcttcg attccaatta cagaaggctc tggagaagca gaagaagatg aagatacaat    5520
```

```
gttcaccatg gtaactgatt tatcacagag aaatactact gatacactca ttactttaga    5580
cactagcagg ataatcacag aaagcttttt tgaggttcct gcaaccacca tttatccagt    5640
ttctgaacaa ccttctgcaa aagtggtgcc taccaagttt gtaagtgaaa cagacacttc    5700
tgagtggatt tccagtacca ctgttgagga aaagaaaagg aaggaggagg agggaactac    5760
aggtacggct tctacatttg aggtatattc atctacacag agatcggatc aattaatttt    5820 acccttttgaa ttagaaagtc caaatgtagc tacatctagt gattcaggta ccaggaaaag    5880
ttttatgtcc ttgacaacac caacacagtc tgaaagggaa atgacagatt ctactcctgt    5940
ctttacagaa acaaatacat tagaaaattt gggggcacag accactgagc acagcagtat    6000
ccatcaacct gggggttcagg aagggctgac cactctccca cgtagtcctg cctctgtctt    6060
tatggagcag ggctctggag aagctgctgc cgacccagaa accaccactg tttcttcatt    6120
ttcattaaac gtagagtatg caattcaagc cgaaaaggaa gtagctggca cttttgtctcc    6180 gcatgtggaa actacattct ccactgagcc aacaggactg gttttgagta cagtaatgga    6240
cagagtagtt gctgaaaata taacccaaac atccaggaa atagtgattt cagagcgatt    6300
aggagaacca aattatgggg cagaaataag gggcttttcc acaggttttc ctttggagga    6360
agatttcagt ggtgacttta gagaatactc aacagtgtct catcccatag caaaagaaga    6420
aacggtaatg atggaaggct ctggagatgc agcatttagg gacacccaga cttcaccatc    6480
tacagtacct acttcagttc acatcagtca catatctgac tcagaaggac ccagtagcac    6540
catggtcagc acttcagcct tcccctggga agagtttaca tcctcagctg agggctcagg    6600
tgagcaactg tcacagtca gcagctctgt tgttccagtg cttcccagtg ctgtgcaaaa    6660
gttttctggt acagcttcct ccattatcga cgaaggattg ggagaagtgg gtactgtcaa    6720
tgaaattgat agaagatcca ccattttacc aacagcagaa gtggaaggta cgaaagctcc    6780
agtagagaag gaggaagtaa aggtcagtgg cacagtttca acaaactttc cccaaactat    6840
agagccagcc aaattatggt ctaggcaaga agtcaaccct gtaagacaag aaattgaaag    6900
tgaaacaaca tcagaggaac aaattcaaga agaaagtca tttgaatccc ctcaaaactc    6960
tcctgcaaca gaacaaacaa tctttgattc acagacattt actgaaactg aactcaaaac    7020
cacagattat tctgtactaa caacaaagaa aacttacagt gatgataaag aaatgaagga    7080
ggaagacact tctttagtta acatgtctac tccagatcca gatgcaaatg gcttggaatc    7140
ttacacaact ctccctgaag ctactgaaaa gtcacatttt ttcttagcta ctgcattagt    7200
aactgaatct ataccagctg aacatgtagt cacagattca ccaatcaaaaa aggaagaaag    7260 tacaaaacat tttccgaaag gcatgagacc aacaattcaa gagtcagata ctgagctctt    7320
attctctgga ctgggatcag gagaagaagt tttacctact ctaccaacag agtcagtgaa    7380
ttttactgaa gtggaacaaa tcaataacac attatatccc cacacttctc aagtggaaag    7440
tacctcaagt gacaaaattg aagactttaa cagaatggaa aatgtggcaa agaagttgg    7500 accactcgta tctcaaacag acatctttga aggtagtggg tcagtaacca gcacaacatt    7560
aatagaaatt ttaagtgaca ctggagcaga aggacccacg gtggcacctc tccctttctc    7620 cacgacatc ggacatcctc aaaatcagac tgtcaggtgg gcagaagaaa tccgactag    7680 tagaccacaa accataactg aacaagactc taacaagaat tcttcaacag cagaaattaa    7740
cgaaacaaca acctcatcta ctgattttct ggctagagct tatggttttg aaatggccaa    7800
agaatttgtt acatcagcac caaaaccatc tgacttgtat tatgaacctt ctggagaagg    7860
atctggagaa gtggatattg ttgattcatt tcacacttct gcaactactc aggcaaccag    7920
```

```
acaagaaagc agcaccacat ttgtttctga tgggtccctg gaaaaacatc ctgaggtgcc    7980
aagcgctaaa gctgttactg ctgatggatt cccaacagtt tcagtgatgc tgcctcttca    8040
ttcagagcag aacaaaagct cccctgatcc aactagcaca ctgtcaaata cagtgtcata    8100
tgagaggtcc acagacggta gtttccaaga ccgtttcagg gaattcgagg attccacctt    8160
aaaacctaac agaaaaaaac ccactgaaaa tattatcata gacctggaca agaggacaa    8220
ggatttaata ttgacaatta cagagagtac catccttgaa attctacctg agctgacatc    8280
ggataaaaat actatcatag atattgatca tactaaacct gtgtatgaag acattcttgg    8340
aatgcaaaca gatatagata cagaggtacc atcagaacca catgacagta atgatgaaag    8400
taatgatgac agcactcaag ttcaagagat ctatgaggca gctgtcaacc tttctttaac    8460
tgaggaaaca tttgagggct ctgctgatgt tctggctagc tacactcagg caacacatga    8520
tgaatcaatg acttatgaag atagaagcca actagatcac atgggctttc acttcacaac    8580
tgggatccct gctcctagca cagaaacaga attagacgtt ttacttccca cggcaacatc    8640
cctgccaatt cctcgtaagt ctgccacagt tattccagag attgaaggaa taaaagctga    8700
agcaaaagcc ctggatgaca tgtttgaatc aagcactttg tctgatggtc aagctattgc    8760
agaccaaagt gaaataatac caacattggg ccaatttgaa aggactcagg aggagtatga    8820
agacaaaaaa catgctggtc cttcttttca gccagaattc tcttcaggag ctgaggaggc    8880
attagtagac catactccct atctaagtat tgctactacc caccttatgg atcagagtgt    8940
aacagaggtg cctgatgtga tggaaggatc caatccccca tattacactg atacaacatt    9000
agcagtttca acatttgcga agttgtcttc tcagacacca tcatctcccc tcactatcta    9060
ctcaggcagt gaagcctctg gacacacaga gatcccccag cccagtgctc tgccaggaat    9120
agacgtcggc tcatctgtaa tgtccccaca ggattctttt aaggaaattc atgtaaatat    9180
tgaagcgact ttcaaaccat caagtgagga ataccttcac ataactgagc ctccctcttt    9240
atctcctgac acaaaattag aaccttcaga agatgatggt aaacctgagt tattagaaga    9300
aatggaagct tctcccacag aacttattgc tgtggaagga actgagattc tccaagattt    9360
ccaaaacaaa accgatggtc aagtttctgg agaagcaatc aagatgtttc ccaccattaa    9420
aacacctgag gctggaactg ttattacaac tgccgatgaa attgaattag aaggtgctac    9480
acagtggcca cactctactt ctgcttctgc cacctatggg gtcgaggcag gtgtggtgcc    9540
ttggctaagt ccacagactt ctgagaggcc cacgctttct tcttctccag aaataaaccc    9600
tgaaactcaa gcagctttaa tcagagggca ggattccacg atagcagcat cagaacagca    9660
agtggcagcg agaattcttg attccaatga tcaggcaaca gtaaaccctg tggaatttaa    9720
tactgaggtt gcaacaccac catttttccct tctggagact tctaatgaaa cagatttcct    9780
gattggcatt aatgaagagt cagtggaagg cacggcaatc tatttaccag gacctgatcg    9840
ctgcaaaatg aacccgtgcc ttaacggagg cacctgttat cctactgaaa cttcctacgt    9900
atgcacctgt gtgccaggat acagcggaga ccagtgtgaa cttgattttg atgaatgtca    9960
ctctaatccc tgtcgtaatg gagccacttg tgttgatggt tttaacacat tcaggtgcct   10020
ctgccttcca agttatgttg gtgcactttg tgagcaagat accgagacat gtgactatgg   10080
ctggcacaaa ttccaagggc agtgctacaa atactttgcc catcgacgca catgggatgc   10140
agctgaacgg gaatgccgtc tgcagggtgc ccatctcaca agcatcctgt ctcacgaaga   10200
acaaatgttt gttaatcgtg tgggccatga ttatcagtgg ataggcctca atgacaagat   10260
```

```
gtttgagcat gacttccgtt ggactgatgg cagcacactg caatacgaga attggagacc      10320
caaccagcca gacagcttct tttctgctgg agaagactgt gttgtaatca tttggcatga      10380
gaatggccag tggaatgatg ttccctgcaa ttaccatctc acctatacgt gcaagaaagg      10440
aacagtcgct tgcggccagc cccctgttgt agaaaatgcc aagacctttg gaaagatgaa      10500
acctcgttat gaaatcaact ccctgattag ataccactgc aaagatggtt tcattcaacg      10560
tcaccttcca actatccggt gcttaggaaa tggaagatgg gctataccta aaattacctg      10620
catgaaccca tctgcatacc aaaggactta ttctatgaaa tactttaaaa attcctcatc      10680
agcaaaggac aattcaataa atacatccaa acatgatcat cgttggagcc ggaggtggca      10740
ggagtcgagg cgctgatccc taaaatggcg aacatgtgtt ttcatcattt cagccaaagt      10800
cctaacttcc tgtgcctttc ctatcacctc gagaagtaat tatcagttgg tttggatttt      10860
tggaccaccg ttcagtcatt ttgggttgcc gtgctcccaa acatttttaa atgaaagtat      10920
tggcattcaa aaagacagca gacaaaatga aagaaaatga gagcagaaag taagcatttc      10980
cagcctatct aatttcttta gttttctatt tgcctccagt gcagtccatt tcctaatgta      11040
taccagccta ctgtactatt taaaatgctc aatttcagca ccgatggcca tgtaaataag      11100
atgatttaat gttgattttta atcctgtata taaaataaaa agtcacaatg agtttgggca      11160
tatttaatga tgattatgga gccttagagg tctttaatca ttggttcggc tgcttttatg      11220
tagtttaggc tggaaatggt ttcacttgct ctttgactgt cagcaagact gaagatggct      11280
tttcctggac agctagaaaa cacaaaatct tgtaggtcat tgcacctatc tcagccatag      11340
gtgcagtttg cttctacatg atgctaaagg ctgcgaatgg gatcctgatg gaactaagga      11400
ctccaatgtc gaactcttct ttgctgcatt cctttttctt cacttacaag aaaggcctga      11460
atggaggact tttctgtaac caggaacatt ttttaggggt caaagtgcta ataattaact      11520
caaccaggtc tactttttaa tggctttcat aacactaact cataaggtta ccgatcaatg      11580
catttcatac ggatatagac ctagggctct ggagggtggg ggattgttaa acacatgca      11640 aaaaaaaaa aaaaaaaaa aaaagaaatt ttgtatatat aaccatttta atcttttata      11700
aagttttgaa tgttcatgta tgaatgctgc agctgtgaag catacataaa taatgaagt      11760 aagccatact gatttaattt attggatgtt attttcccta agacctgaaa atgaacatag      11820
tatgctagtt atttttcagt gttagccttt tactttcctc acacaatttg gaatcatata      11880
atataggtac tttgtccctg attaaataat gtgacggata gaatgcatca agtgtttatt      11940
atgaaaagag tggaaaagta tatagctttt agcaaaaggt gtttgcccat tctaagaaat      12000
gagcgaatat atagaaatag tgtgggcatt tcttcctgtt aggtggagtg tatgtgttga      12060
catttctccc catctcttcc cactctgttt tctccccatt atttgaataa agtgactgct      12120
gaagatgact ttgaatcctt atccacttaa tttaatgttt aaagaaaaac ctgtaatgga      12180
aagtaagact ccttccctaa tttcagttta gagcaacttg aagaagagta gacaaaaaat      12240
aaaatgcaca tagaaaaaga gaaaagggc acaagggat tggcccaata ttgattctt       12300 ttttataaaa cctccttttgg cttagaagga atgactctag ctacaataat acacagtatg      12360
tttaagcagg ttcccttggt tgttgcatta aatgtaatcc acctttaggt attttagagc      12420
acagaacaac actgtgttga tctagtaggt ttctattttt cctttctctt tacaatgcac      12480
ataatacttt cctgtattta tatcataacg tgtatagtgt aaaatgtgaa tgacttttt       12540 tgtgaatgaa aatctaaaat ctttgtaact ttttatatct gcttttgttt caccaaagaa      12600
acctaaaatc cttctttac tacac                                            12625
```

<210> SEQ ID NO 47
<211> LENGTH: 6795
<212> TYPE: DNA
<213> ORGANISM: human

<400> SEQUENCE: 47

| | | | | | |
|---|---|---|---|---|---|
| acagtgatat | aatgatgatg | ggtgtcacaa | cccgcatttg | aacttgcagg | cgagctgccc | 60 |
| cgagcctttc | tggggaagaa | ctccaggcgt | gcggacgcaa | cagccgagaa | cattaggtgt | 120 |
| tgtggacagg | agctgggacc | aagatcttcg | gccagccccg | catcctcccg | catcttccag | 180 |
| caccgtcccg | caccctccgc | atccttcccc | gggccaccac | gcttcctatg | tgacccgcct | 240 |
| gggcaacgcc | gaacccagtc | gcgcagcgct | gcagtgaatt | ttccccccaa | actgcaataa | 300 |
| gccgccttcc | aaggccaaga | tgttcataaa | tataaagagc | atcttatgga | tgtgttcaac | 360 |
| cttaatagta | acccatgcgc | tacataaagt | caaagtggga | aaaagcccac | cggtgagggg | 420 |
| ctccctctct | ggaaaagtca | gcctaccttg | tcatttttca | acgatgccta | ctttgccacc | 480 |
| cagttacaac | accagtgaat | ttctccgcat | caaatggtct | aagattgaag | tggacaaaaa | 540 |
| tggaaaagat | ttgaaagaga | ctactgtcct | tgtggcccaa | aatggaaata | tcaagattgg | 600 |
| tcaggactac | aaagggagag | tgtctgtgcc | cacacatccc | gaggctgtgg | gcgatgcctc | 660 |
| cctcactgtg | gtcaagctgc | tggcaagtga | tgcgggtctt | taccgctgtg | acgtcatgta | 720 |
| cgggattgaa | gacacacaag | acacggtgtc | actgactgtg | gatggggttg | tgtttcacta | 780 |
| cagggcggca | accagcaggt | acacactgaa | ttttgaggct | gctcagaagg | cttgtttgga | 840 |
| cgttggggca | gtcatagcaa | ctccagagca | gctctttgct | gcctatgaag | atggatttga | 900 |
| gcagtgtgac | gcaggctggc | tggctgatca | gactgtcaga | tatcccatcc | gggctcccag | 960 |
| agtaggctgt | tatggagata | agatgggaaa | ggcaggagtc | aggacttatg | gattccgttc | 1020 |
| tccccaggaa | acttacgatg | tgtattgtta | tgtggatcat | ctggatggtg | atgtgttcca | 1080 |
| cctcactgtc | cccagtaaat | tcaccttcga | ggaggctgca | aaagagtgtg | aaaaccagga | 1140 |
| tgccaggctg | gcaacagtgg | gggaactcca | ggcggcatgg | aggaacggct | ttgaccagtg | 1200 |
| cgattacggg | tggctgtcgg | atgccagcgt | gcgccaccct | gtgactgtgg | ccagggccca | 1260 |
| gtgtggaggt | ggtctacttg | gggtgagaac | cctgtatcgt | tttgagaacc | agacaggctt | 1320 |
| cccctccccct | gatagcagat | tgatgcctta | ctgctttaaa | cctaaagagg | ctacaaccat | 1380 |
| cgatttgagt | atcctcgcag | aaactgcatc | acccagttta | tccaaagaac | cacaaatggt | 1440 |
| ttctgataga | actacaccaa | tcatcccttt | agttgatgaa | ttacctgtca | ttccaacaga | 1500 |
| gttccctccc | gtgggaaata | ttgtcagttt | tgaacagaaa | gccacagtcc | aacctcaggc | 1560 |
| tatcacagat | agtttagcca | ccaaattacc | cacacctact | ggcagtacca | agaagcctg | 1620 |
| ggatatggat | gactactcac | cttctgcttc | aggacctctt | ggaaagctag | acatatcaga | 1680 |
| aattaaggaa | gaagtgctcc | agagtacaac | tggcgtctct | cattatgcta | cggattcatg | 1740 |
| ggatggtgtc | gtggaagata | acaaacaca | gaatcggtt | acacagattg | aacaaataga | 1800 |
| agtgggtcct | ttggtaacat | ctatggaaat | cttaaagcac | attccttcca | aggaattccc | 1860 |
| tgtaactgaa | acaccattgg | taactgcaag | aatgatcctg | gaatccaaaa | ctgaaaagaa | 1920 |
| aatggtaagc | actgttttctg | aattggtaac | cacaggtcac | tatggattca | ccttgggaga | 1980 |
| agaggatgat | gaagacagaa | cacttacagt | tggatctgat | gagagcacct | tgatctttga | 2040 |
| ccaaattcct | gaagtcatta | cggtgtcaaa | gacttcagaa | gacaccatcc | acactcattt | 2100 |

```
agaagacttg gagtcagtct cagcatccac aactgtttcc cctttaatta tgcctgataa    2160
taatggatca tccatggatg actgggaaga gagacaaact agtggtagga taacggaaga    2220
gtttcttggc aaatatctgt ctactacacc ttttccatca cagcatcgta cagaaataga    2280
attgtttcct tattctggtg ataaaatatt agtagaggga atttccacag ttatttatcc    2340
ttctctacaa acagaaatga cacatagaag agaaagaaca gaaacactaa taccagagat    2400
gagaacagat acttatacag atgaaataca agaagagatc actaaaagtc catttatggg    2460
aaaaacagaa gaagaagtct tctctgggat gaaactctct acatctctct cagagccaat    2520
tcatgttaca gagtcttctg tggaaatgac caagtctttt gatttcccaa cattgataac    2580
aaagttaagt gcagagccaa cagaagtaag agatatggag gaagacttta cagcaactcc    2640
aggtactaca aaatatgatg aaaatattac aacagtgctt ttggcccatg gtactttaag    2700
tgttgaagca gccactgtat caaaatggtc atgggatgaa gataatacaa catccaagcc    2760
tttagagtct acagaacctt cagcctcttc aaaattgccc cctgccttac tcacaactgt    2820
ggggatgaat ggaaaggata aagacatccc aagtttcact gaagatggag cagatgaatt    2880
tactcttatt ccagatagta ctcaaaagca gttagaggag gttactgatg aagacatagc    2940
agcccatgga aaattcacaa ttagatttca gccaactaca tcaactggta ttgcagaaaa    3000
gtcaactttg agagattcta caactgaaga aaaagttcca cctatcacaa gcactgaagg    3060
ccaagtttat gcaaccatgg aaggaagtgc tttgggtgaa gtagaagatg tggacctctc    3120
taagccagta tctactgttc cccaatttgc acacacttca gaggtggaag gattagcatt    3180
tgttagttat agtagcaccc aagagcctac tacttatgta gactcttccc ataccattcc    3240
tctttctgta attcccaaga cagactgggg agtgttagta ccttctgttc catcagaaga    3300
tgaagttcta ggtgaaccct ctcaagacat acttgtcatt gatcagactc gccttgaagc    3360
gactatttct ccagaaacta tgagaacaac aaaaatcaca gagggaacaa ctcaggaaga    3420
attcccttgg aaagaacaga ctgcagagaa accagttcct gctctcagtt ctacagcttg    3480
gactcccaag gaggcagtaa caccactgga tgaacaagag ggcgatggat cagcatatac    3540
agtctctgaa gatgaattgt tgacaggttc tgagagggtc ccagttttag aaacaactcc    3600
agttggaaaa attgatcaca gtgtgtctta tccaccaggt gctgtaactg agcacaaagt    3660
gaaaacagat gaagtggtaa cactaacacc acgcattggg ccaaaagtat ctttaagtcc    3720
agggcctgaa caaaaatatg aaacagaagg tagtagtaca acaggattta catcatcttt    3780
gagtcctttt agtacccaca ttacccagct tatggaagaa accactactg agaaaacatc    3840
cctagaggat attgatttag gctcaggatt atttgaaaag cccaaagcca cagaactcat    3900
agaattttca acaatcaaag tcacagttcc aagtgatatt accactgcct tcagttcagt    3960
agacagactt cacacaactt cagcattcaa gccatcttcc gcgatcacta agaaaccacc    4020
tctcatcgac agggaacctg gtgaagaaac aaccagtgac atggtaatca ttggagaatc    4080
aacatctcat gttcctccca ctaccttga agatattgta gccaaggaaa cagaaaccga    4140
tattgataga gagtatttca cgacttcaag tcctcctgct acacagccaa caagaccacc    4200
cactgtggaa gacaaagagg cctttggacc tcaggcgctt tctacgccac agcccccagc    4260
aagcacaaaa tttcaccctg acattaatgt ttatattatt gaggtcagag aaaataagac    4320
aggacctgat cgctgcaaaa tgaacccgtg ccttaacgga ggcacctgtt atcctactga    4380
aacttcctac gtatgcacct gtgtgccagg atacagcgga gaccagtgtg aacttgattt    4440
tgatgaatgt cactctaatc cctgtcgtaa tggagccact tgtgttgatg gttttaacac    4500
```

```
attcaggtgc ctctgccttc caagttatgt tggtgcactt tgtgagcaag ataccgagac    4560
atgtgactat ggctggcaca aattccaagg gcagtgctac aaatactttg cccatcgacg    4620
cacatgggat gcagctgaac gggaatgccg tctgcagggt gcccatctca caagcatcct    4680
gtctcacgaa gaacaaatgt tgttaatcg tgtgggccat gattatcagt ggataggcct    4740
caatgacaag atgtttgagc atgacttccg ttggactgat ggcagcacac tgcaatacga    4800
gaattggaga cccaaccagc cagacagctt cttttctgct ggagaagact gtgttgtaat    4860
catttggcat gagaatggcc agtggaatga tgttccctgc aattaccatc tcacctatac    4920
gtgcaagaaa ggaacagtcg cttgcggcca gcccctgtt gtagaaaatg ccaagacctt    4980
tggaaagatg aaacctcgtt atgaaatcaa ctccctgatt agataccact gcaaagatgg    5040
tttcattcaa cgtcaccttc caactatccg gtgcttagga aatggaagat gggctatacc    5100
taaaattacc tgcatgaacc catctgcata ccaaaggact tattctatga aatactttaa    5160
aaattcctca tcagcaaagg acaattcaat aaatacatcc aaacatgatc atcgttggag    5220
ccggaggtgg caggagtcga ggcgctgatc cctaaaatgg cgaacatgtg ttttcatcat    5280
ttcagccaaa gtcctaactt cctgtgcctt tcctatcacc tcgagaagta attatcagtt    5340
ggtttggatt tttggaccac cgttcagtca tttttgggttg ccgtgctccc aaaacatttt    5400
aaatgaaagt attggcattc aaaaagacag cagacaaaat gaaagaaaat gagagcagaa    5460
agtaagcatt tccagcctat ctaatttctt tagttttcta tttgcctcca gtgcagtcca    5520
tttcctaatg tataccagcc tactgtacta tttaaaatgc tcaatttcag caccgatggc    5580
catgtaaata agatgattta atgttgattt taatcctgta tataaaataa aaagtcacaa    5640
tgagtttggg catatttaat gatgattatg gagccttaga ggtctttaat cattggttcg    5700 gctgcttta tgtagtttag gctggaaatg gtttcacttg ctctttgact gtcagcaaga    5760
ctgaagatgg cttttcctgg acagctagaa aacacaaaat cttgtaggtc attgcaccta    5820
tctcagccat aggtgcagtt tgcttctaca tgatgctaaa ggctgcgaat gggatcctga    5880
tggaactaag gactccaatg tcgaactctt ctttgctgca ttcctttttc ttcacttaca    5940
agaaaggcct gaatggagga cttttctgta accaggaaca ttttttaggg gtcaaagtgc    6000
taataattaa ctcaaccagg tctactttt aatggctttc ataacactaa ctcataaggt    6060
taccgatcaa tgcatttcat acggatatag acctagggct ctggagggtg ggggattgtt    6120
aaaacacatg caaaaaaaaa aaaaaaaaa aaaaagaaa ttttgtatat ataaccattt    6180 taatcttta taagtttttg aatgttcatg tatgaatgct gcagctgtga agcatacata    6240
aataaatgaa gtaagccata ctgatttaat ttattggatg ttatttcc taagacctga    6300 aaatgaacat agtatgctag ttattttca gtgttagcct tttactttcc tcacacaatt    6360
tggaatcata taatataggt actttgtccc tgattaaata atgtgacgga tagaatgcat    6420
caagtgttta ttatgaaaag agtggaaaag tatatagctt ttagcaaaag gtgtttgccc    6480
attctaagaa atgagcgaat atatagaaat agtgtgggca tttcttcctg ttaggtggag    6540
tgtatgtgtt gacatttctc cccatctctt cccactctgt tttctcccca ttatttgaat    6600
aaagtgactg ctgaagatga ctttgaatcc ttatccactt aatttaatgt ttaaagaaaa    6660
acctgtaatg gaaagtaaga ctccttccct aatttcagtt tagagcaact tgaagaagag    6720
tagacaaaaa ataaaatgca catagaaaaa gagaaaaagg gcacaaaggg attggcccaa    6780
tattgattct tttt                                                     6795
```

<210> SEQ ID NO 48
<211> LENGTH: 9096
<212> TYPE: DNA
<213> ORGANISM: human

<400> SEQUENCE: 48

```
acagtgatat aatgatgatg ggtgtcacaa cccgcatttg aacttgcagg cgagctgccc      60
cgagcctttc tggggaagaa ctccaggcgt gcggacgcaa cagccgagaa cattaggtgt     120
tgtggacagg agctgggacc aagatcttcg gccagcccg catcctcccg catcttccag      180
caccgtcccg caccctccgc atccttcccc gggccaccac gcttcctatg tgacccgcct     240
gggcaacgcc gaacccagtc gcgcagcgct gcagtgaatt ttccccccaa actgcaataa     300
gccgccttcc aaggccaaga tgttcataaa tataaagagc atcttatgga tgtgttcaac     360
cttaatagta acccatgcgc tacataaagt caaagtggga aaaagcccac cggtgagggg     420
ctccctctct ggaaaagtca gcctaccttg tcattttca acgatgccta ctttgccacc      480
cagttacaac accagtgaat ttctccgcat caaatggtct aagattgaag tggacaaaaa     540
tggaaaagat ttgaaagaga ctactgtcct tgtgcccaa aatggaaata tcaagattgg      600
tcaggactac aaagggagag tgtctgtgcc cacacatccc gaggctgtgg gcgatgcctc     660
cctcactgtg gtcaagctgc tggcaagtga tgcgggtctt taccgctgtg acgtcatgta     720
cgggattgaa gacacacaag acacggtgtc actgactgtg gatggggttg tgtttcacta     780
cagggcggca accagcaggt acacactgaa ttttgaggct gctcagaagg cttgtttgga     840
cgttgggca gtcatagcaa ctccagagca gctctttgct gcctatgaag atggatttga      900
gcagtgtgac gcaggctggc tggctgatca gactgtcaga tatcccatcc gggctcccag     960
agtaggctgt tatggagata agatgggaaa ggcaggagtc aggacttatg gattccgttc    1020
tccccaggaa acttacgatg tgtattgtta tgtggatcat ctggatggtg atgtgttcca    1080
cctcactgtc cccagtaaat tcaccttcga ggaggctgca aaagagtgtg aaaaccagga    1140
tgccaggctg gcaacagtgg gggaactcca ggcggcatgg aggaacggct tgaccagtg     1200
cgattacggg tggctgtcgg atgccagcgt gcgccaccct gtgactgtgg ccagggccca    1260
gtgtggaggt ggtctacttg gggtgagaac cctgtatcgt tttgagaacc agacaggctt    1320
ccctcccct gatagcagat ttgatgccta ctgctttaaa cgtcgaatga gtgatttgag     1380
tgtaattggt catccaatag attcagaatc taaagaagat gaaccttgta gtgaagaaac    1440
agatccagtg catgatctaa tggctgaaat tttacctgaa ttccctgaca taattgaaat    1500
agacctatac cacagtgaag aaaatgaaga agaagaagaa gagtgtgcaa atgctactga    1560
tgtgacaacc accccatctg tgcagtacat aaatgggaag catctcgtta ccactgtgcc    1620
caaggaccca gaagctgcag aagctaggcg tggccagttt gaaagtgttg caccttctca    1680
gaatttctcg gacagctctg aaagtgatac tcatccattt gtaatagcca aaacggaatt    1740
gtctactgct gtgcaaccta atgaatctac agaaacaact gagtctcttg aagttacatg    1800
gaagcctgag acttaccctg aaacatcaga acattttca ggtggtgagc ctgatgtttt     1860
ccccacagtc ccattccatg aggaatttga agtggaaca gccaaaaaag gggcagaatc    1920
agtcacagag agagatactg aagttggtca tcaggcacat gaacatactg aacctgtatc    1980
tctgtttcct gaaagagtct tcaggagagat tgccattgac caagaatctc agaaaatagc    2040
cttttgcaagg gctacagaag taacatttgg tgaagaggta gaaaaagta cttctgtcac    2100
atacactccc actatagttc caagttctgc atcagcatat gtttcagagg aagaagcagt    2160
```

```
taccctaata ggaaatcctt ggccagatga cctgttgtct accaaagaaa gctgggtaga    2220
agcaactcct agacaagttg tagagctctc agggagttct tcgattccaa ttacagaagg    2280
ctctggagaa gcagaagaag atgaagatac aatgttcacc atggtaactg atttatcaca    2340
gagaaatact actgatacac tcattacttt agacactagc aggataatca cagaaagctt    2400
ttttgaggtt cctgcaacca ccatttatcc agtttctgaa caaccttctg caaaagtggt    2460
gcctaccaag tttgtaagtg aaacagacac ttctgagtgg atttccagta ccactgttga    2520
ggaaaagaaa aggaaggagg aggagggaac tacaggtacg gcttctacat ttgaggtata    2580
ttcatctaca cagagatcgg atcaattaat tttacccttt gaattagaaa gtccaaatgt    2640
agctacatct agtgattcag gtaccaggaa aagttttatg tccttgacaa caccaacaca    2700
gtctgaaagg gaaatgacag attctactcc tgtctttaca gaaacaaata cattagaaaa    2760
tttgggggca cagaccactg agcacagcag tatccatcaa cctggggttc aggaagggct    2820
gaccactctc ccacgtagtc ctgcctctgt ctttatggag cagggctctg agaagctgc     2880 tgccgaccca gaaaccacca ctgtttcttc attttcatta aacgtagagt atgcaattca    2940
agccgaaaag gaagtagctg gcactttgtc tccgcatgtg gaaactacat tctccactga    3000
gccaacagga ctggttttga gtacagtaat ggacagagta gttgctgaaa atataaccca    3060
aacatccagg gaaatagtga tttcagagcg attaggagaa ccaaattatg gggcagaaat    3120 aagggggcttt tccacaggtt ttcctttgga ggaagatttc agtggtgact ttagagaata    3180
ctcaacagtg tctcatccca tagcaaaaga agaaacggta atgatggaag gctctggaga    3240
tgcagcattt agggacaccc agacttcacc atctacagta cctacttcag ttcacatcag    3300
tcacatatct gactcagaag gacccagtag caccatggtc agcacttcag ccttcccctg    3360
ggaagagttt acatcctcag ctgagggctc aggtgagcaa ctggtcacag tcagcagctc    3420
tgttgttcca gtgcttccca gtgctgtgca aaagttttct ggtacagctt cctccattat    3480
cgacgaagga ttgggagaag tgggtactgt caatgaaatt gatagaagat ccaccatttt    3540
accaacagca gaagtggaag gtacgaaagc tccagtagag aaggaggaag taaaggtcag    3600
tggcacagtt tcaacaaact ttccccaaac tatagagcca gccaaattat ggtctaggca    3660
agaagtcaac cctgtaagac aagaaattga aagtgaaaca acatcagagg aacaaattca    3720
agaagaaaag tcatttgaat cccctcaaaa ctctcctgca acagaacaaa caatctttga    3780
ttcacagaca tttactgaaa ctgaactcaa aaccacagat tattctgtac taacaacaaa    3840
gaaaacttac agtgatgata agaaatgaa ggaggaagac acttctttag ttaacatgtc     3900
tactccagat ccagatgcaa atggcttgga atcttacaca actctccctg aagctactga    3960
aaagtcacat ttttcttag ctactgcatt agtaactgaa tctataccag ctgaacatgt     4020
agtcacagat tcaccaatca aaaggaaga agtacaaaa cattttccga aaggcatgag     4080
accaacaatt caagagtcag atactgagct cttattctct ggactgggat caggagaaga    4140
agttttacct actctaccaa cagagtcagt gaattttact gaagtggaac aaatcaataa    4200
cacattatat ccccacactt ctcaagtgga aagtacctca agtgacaaaa ttgaagactt    4260
taacagaatg gaaaatgtgg caaaagaagt tggaccactc gtatctcaaa cagacatctt    4320
tgaaggtagt gggtcagtaa ccagcacaac attaatagaa attttaagtg acactggagc    4380
agaaggaccc acggtggcac ctctcccttt ctccacggac atcggacatc ctcaaaatca    4440
gactgtcagg tgggcagaag aaatccagac tagtagacca caaaccataa ctgaacaaga    4500
```

```
ctctaacaag aattcttcaa cagcagaaat taacgaaaca acaacctcat ctactgattt    4560
tctggctaga gcttatggtt ttgaaatggc caaagaattt gttacatcag caccaaaacc    4620
atctgacttg tattatgaac cttctggaga aggatctgga gaagtggata ttgttgattc    4680
atttcacact tctgcaacta ctcaggcaac cagacaagaa agcagcacca catttgtttc    4740
tgatgggtcc ctggaaaaac atcctgaggt gccaagcgct aaagctgtta ctgctgatgg    4800
attcccaaca gtttcagtga tgctgcctct tcattcagag cagaacaaaa gctcccctga    4860
tccaactagc acactgtcaa atacagtgtc atatgagagg tccacagacg gtagtttcca    4920
agaccgtttc agggaattcg aggattccac cttaaaacct aacagaaaaa aacccactga    4980
aaatattatc atagacctgg acaaagagga caaggattta atattgacaa ttacagagag    5040
taccatcctt gaaattctac ctgagctgac atcggataaa aatactatca tagatattga    5100
tcatactaaa cctgtgtatg aagacattct tggaatgcaa acagatatag atacagaggt    5160
accatcagaa ccacatgaca gtaatgatga agtaatgat gacagcactc aagttcaaga    5220
gatctatgag gcagctgtca acctttcttt aactgaggaa catttgagg gctctgctga    5280 tgttctggct agctacactc aggcaacaca tgatgaatca atgacttatg aagatagaag    5340
ccaactagat cacatgggct ttcacttcac aactgggatc cctgctccta gcacagaaac    5400
agaattagac gttttacttc ccacggcaac atccctgcca attcctcgta agtctgccac    5460
agttattcca gagattgaag gaataaaagc tgaagcaaaa gccctggatg acatgtttga    5520
atcaagcact ttgtctgatg gtcaagctat tgcagaccaa agtgaaataa taccaacatt    5580
gggccaattt gaaaggactc aggaggagta tgaagacaaa aaacatgctg gtccttcttt    5640
tcagccagaa ttctcttcag gagctgagga ggcattagta gaccatactc cctatctaag    5700
tattgctact acccaacctta tggatcgag tgtaacagag gtgcctgatg tgatggaagg    5760
atccaatccc ccatattaca ctgatacaac attagcagtt tcaacatttg cgaagttgtc    5820
ttctcagaca ccatcatctc ccctcactat ctactcaggc agtgaagcct ctggacacac    5880
agagatcccc cagcccagtg ctctgccagg aatagacgtc ggctcatctg taatgtcccc    5940
acaggattct tttaaggaaa ttcatgtaaa tattgaagcg actttcaaac catcaagtga    6000 ggaataccett cacataactg agcctccctc tttatctcct gacacaaaat tagaaccttc    6060
agaagatgat ggtaaacctg agttattaga agaaatggaa gcttctccca cagaacttat    6120
tgctgtggaa ggaactgaga ttctccaaga tttccaaaac aaaaccgatg gtcaagtttc    6180
tggagaagca atcaagatgt ttcccaccat taaaacacct gaggctggaa ctgttattac    6240
aactgccgat gaaattgaat tagaaggtgc tacacagtgg ccacactcta cttctgcttc    6300
tgccacctat ggggtcgagg caggtgtggt gccttggcta agtccacaga cttctgagag    6360
gcccacgctt tcttcttctc cagaaataaa ccctgaaact caagcagctt taatcagagg    6420
gcaggattcc acgatagcag catcagaaca gcagtggca gcgagaattc ttgattccaa    6480
tgatcaggca acagtaaacc ctgtggaatt taatactgag gttgcaacac caccattttc    6540
ccttctggag acttctaatg aaacagattt cctgattggc attaatgaag agtcagtgga    6600
aggcacggca atctatttac caggacctga tcgctgcaaa atgaacccgt gccttaacgg    6660
aggcacctgt tatcctactg aaacttccta cgtatgcacc tgtgtgccag atacagcgg    6720 agaccagtgt gaacttgatt ttgatgaatg tcactctaat ccctgtcgta atggagccac    6780
ttgtgttgat ggttttaaca cattcaggtg cctctgcctt ccaagttatg ttggtgcact    6840
ttgtgagcaa gataccgaga catgtgacta tggctggcac aaattccaag gcagtgcta    6900
```

```
caaatacttt gcccatcgac gcacatggga tgcagctgaa cgggaatgcc gtctgcaggg    6960
tgcccatctc acaagcatcc tgtctcacga agaacaaatg tttgttaatc gtgtgggcca    7020
tgattatcag tggataggcc tcaatgacaa gatgtttgag catgacttcc gttggactga    7080
tggcagcaca ctgcaatacg agaattggag acccaaccag ccagacagct tcttttctgc    7140
tggagaagac tgtgttgtaa tcatttggca tgagaatggc cagtggaatg atgttccctg    7200
caattaccat ctcacctata cgtgcaagaa aggaacagtc gcttgcggcc agccccctgt    7260
tgtagaaaat gccaagacct tggaaagat gaaacctcgt tatgaaatca actccctgat    7320
tagataccac tgcaaagatg gtttcattca acgtcacctt ccaactatcc ggtgcttagg    7380
aaatggaaga tgggctatac ctaaaattac ctgcatgaac ccatctgcat accaaaggac    7440
ttattctatg aaatacttta aaaattcctc atcagcaaag gacaattcaa taaatacatc    7500
caaacatgat catcgttgga gccggagtg gcaggagtcg aggcgctgat ccctaaaatg    7560
gcgaacatgt gttttcatca tttcagccaa agtcctaact tcctgtgcct ttcctatcac    7620
ctcgagaagt aattatcagt tggtttggat ttttggacca ccgttcagtc attttgggtt    7680
gccgtgctcc caaacattt taaatgaaag tattggcatt caaaaagaca gcagacaaaa    7740
tgaaagaaaa tgagagcaga agtaagcat ttccagccta tctaatttct ttagttttct    7800
atttgcctcc agtgcagtcc atttcctaat gtataccagc ctactgtact atttaaaatg    7860
ctcaatttca gcaccgatgg ccatgtaaat aagatgattt aatgttgatt ttaatcctgt    7920
atataaaata aaaagtcaca atgagtttgg gcatatttaa tgatgattat ggagccttag    7980
aggtctttaa tcattggttc ggctgctttt atgtagttta ggctggaaat ggtttcactt    8040
gctctttgac tgtcagcaag actgaagatg gcttttcctg gacagctaga aaacacaaaa    8100
tcttgtaggt cattgcacct atctcagcca taggtgcagt ttgcttctac atgatgctaa    8160
aggctgcgaa tgggatcctg atggaactaa ggactccaat gtcgaactct tctttgctgc    8220 attcctttt cttcacttac aagaaaggcc tgaatggagg acttttctgt aaccaggaac    8280
attttttagg ggtcaaagtg ctaataatta actcaaccag gtctacttt taatggcttt    8340 cataacacta actcataagg ttaccgatca atgcatttca tacggatata gacctagggc    8400
tctggagggt gggggattgt taaaacacat gcaaaaaaaa aaaaaaaaa aaaaaagaa    8460 attttgtata tataaccatt ttaatctttt ataaagtttt gaatgttcat gtatgaatgc    8520
tgcagctgtg aagcatacat aaataaatga agtaagccat actgatttaa tttattggat    8580 gttatttttcc ctaagacctg aaaatgaaca tagtatgcta gttatttttc agtgttagcc    8640 tttttactttc ctcacacaat ttggaatcat ataatatagg tactttgtcc ctgattaaat    8700
aatgtgacgg atagaatgca tcaagtgttt attatgaaaa gagtggaaaa gtatatagct    8760
tttagcaaaa ggtgtttgcc cattctaaga aatgagcgaa tatatagaaa tagtgtgggc    8820
atttcttcct gttaggtgga gtgtatgtgt tgacatttct ccccatctct tcccactctg    8880
ttttctcccc attatttgaa taaagtgact gctgaagatg actttgaatc cttatccact    8940
taatttaatg tttaaagaaa aacctgtaat ggaaagtaag actccttccc taatttcagt    9000
ttagagcaac ttgaagaaga gtagacaaaa aataaaatgc acatagaaaa agagaaaaag    9060
ggcacaaagg gattggccca atattgattc tttttt                            9096
```

<210> SEQ ID NO 49
<211> LENGTH: 3834
<212> TYPE: DNA

<213> ORGANISM: human

<400> SEQUENCE: 49

```
acagtgatat aatgatgatg ggtgtcacaa cccgcatttg aacttgcagg cgagctgccc      60
cgagcctttc tggggaagaa ctccaggcgt gcggacgcaa cagccgagaa cattaggtgt     120
tgtggacagg agctgggacc aagatcttcg gccagccccg catcctcccg catcttccag     180
caccgtcccg caccctccgc atccttcccc gggccaccac gcttcctatg tgacccgcct     240
gggcaacgcc gaacccagtc gcgcagcgct gcagtgaatt ttccccccaa actgcaataa     300
gccgccttcc aaggccaaga tgttcataaa tataaagagc atcttatgga tgtgttcaac     360
cttaatagta acccatgcgc tacataaagt caaagtggga aaaagcccac cggtgagggg     420
ctccctctct ggaaaagtca gcctaccttg tcatttttca acgatgccta ctttgccacc     480
cagttacaac accagtgaat ttctccgcat caaatggtct aagattgaag tggacaaaaa     540
tggaaaagat ttgaaagaga ctactgtcct tgtgcccaa aatggaaata tcaagattgg     600
tcaggactac aaagggagag tgtctgtgcc acacatccc gaggctgtgg gcgatgcctc     660
cctcactgtg gtcaagctgc tggcaagtga tgcgggtctt taccgctgtg acgtcatgta     720
cgggattgaa gacacacaag acacggtgtc actgactgtg gatggggttg tgtttcacta     780
cagggcggca accagcaggt acacactgaa ttttgaggct gctcagaagg cttgtttgga     840
cgttggggca gtcatagcaa ctccagagca gctctttgct gcctatgaag atggatttga     900
gcagtgtgac gcaggctggc tggctgatca gactgtcaga tatcccatcc gggctcccag     960
agtaggctgt tatggagata agatgggaaa ggcaggagtc aggacttatg gattccgttc    1020
tcccaggaa acttacgatg tgtattgtta tgtggatcat ctggatggtg atgtgttcca    1080
cctcactgtc cccagtaaat tcaccttcga ggaggctgca aaagagtgtg aaaaccagga    1140
tgccaggctg gcaacagtgg gggaactcca ggcggcatgg aggaacggct tgaccagtg    1200
cgattacggg tggctgtcgg atgccagcgt gcgccaccct gtgactgtgg ccagggccca    1260
gtgtggaggt ggtctacttg gggtgagaac cctgtatcgt tttgagaacc agacaggctt    1320
ccctcccct gatagcagat tgatgcta ctgctttaaa cgacctgatc gctgcaaaat    1380
gaacccgtgc cttaacggag gcacctgtta tcctactgaa acttcctacg tatgcacctg    1440
tgtgccagga tacagcggag accagtgtga acttgatttt gatgaatgtc actctaatcc    1500
ctgtcgtaat ggagccactt gtgttgatgg ttttaacaca ttcaggtgcc tctgccttcc    1560
aagttatgtt ggtgcacttt gtgagcaaga taccgagaca tgtgactatg gctggcacaa    1620
attccaaggg cagtgctaca atactttgc ccatcgacgc acatgggatg cagctgaacg    1680
ggaatgccgt ctgcagggtg cccatctcac aagcatcctg tctcacgaag aacaaatgtt    1740
tgttaatcgt gtgggccatg attatcagtg gataggcctc aatgacaaga tgtttgagca    1800
tgacttccgt tggactgatg gcagcacact gcaatacgag aattggagac ccaaccagcc    1860
agacagcttc ttttctgctg gagaagactg tgttgtaatc atttggcatg agaatggcca    1920
gtggaatgat gttccctgca attaccatct cacctatacg tgcaagaaag gaacagtcgc    1980
ttgcggccag ccccctgttg tagaaaatgc caagaccttt ggaagatga aacctcgtta    2040
tgaaatcaac tccctgatta gataccactg caaagatggt ttcattcaac gtcaccttcc    2100
aactatccgg tgcttaggaa atggaagatg gctataccct aaaattacct gcatgaaccc    2160
atctgcatac caaaggactt attctatgaa atactttaaa aattcctcat cagcaaagga    2220
caattcaata aatacatcca aacatgatca tcgttggagc cggaggtggc aggagtcgag    2280
```

```
gcgctgatcc ctaaaatggc gaacatgtgt tttcatcatt tcagccaaag tcctaacttc    2340
ctgtgccttt cctatcacct cgagaagtaa ttatcagttg gtttggattt ttggaccacc    2400
gttcagtcat tttgggttgc cgtgctccca aaacatttta aatgaaagta ttggcattca    2460
aaaagacagc agacaaaatg aaagaaaatg agagcagaaa gtaagcattt ccagcctatc    2520
taatttcttt agttttctat ttgcctccag tgcagtccat ttcctaatgt ataccagcct    2580
actgtactat ttaaaatgct caatttcagc accgatggcc atgtaaataa gatgatttaa    2640
tgttgatttt aatcctgtat ataaaataaa agtcacaat gagtttgggc atatttaatg    2700
atgattatgg agccttagag gtctttaatc attggttcgg ctgcttttat gtagtttagg    2760
ctggaaatgg tttcacttgc tctttgactg tcagcaagac tgaagatggc ttttcctgga    2820
cagctagaaa acacaaaatc ttgtaggtca ttgcacctat ctcagccata ggtgcagttt    2880
gcttctacat gatgctaaag gctgcgaatg ggatcctgat ggaactaagg actccaatgt    2940
cgaactcttc tttgctgcat tccttttttct tcacttacaa gaaaggcctg aatggaggac    3000
ttttctgtaa ccaggaacat ttttaggg tcaaagtgct aataattaac tcaaccaggt    3060 ctactttta atggctttca taacactaac tcataaggtt accgatcaat gcatttcata    3120
cggatataga cctagggctc tggagggtgg gggattgtta aaacacatgc aaaaaaaaaa    3180 aaaaaaaaa aaaagaaat tttgtatata taaccatttt aatctttat aaagttttga    3240 atgttcatgt atgaatgctg cagctgtgaa gcatacataa ataaatgaag taagccatac    3300
tgatttaatt tattggatgt tatttttccct aagacctgaa aatgaacata gtatgctagt    3360
tatttttcag tgttagcctt ttactttcct cacacaattt ggaatcatat aatataggta    3420
ctttgtccct gattaaataa tgtgacggat agaatgcatc aagtgtttat tatgaaaaga    3480
gtggaaaagt atatagctt tagcaaaagg tgtttgccca ttctaagaaa tgagcgaata    3540
tatagaaata gtgtgggcat ttcttcctgt taggtggagt gtatgtgttg acatttctcc    3600
ccatctcttc ccactctgtt ttctccccat tatttgaata aagtgactgc tgaagatgac    3660
tttgaatcct tatccactta atttaatgtt taaagaaaaa cctgtaatgg aaagtaagac    3720
tccttcccta atttcagttt agagcaactt gaagaagagt agacaaaaaa taaaatgcac    3780
atagaaaaag agaaaaggg cacaagggga ttggcccaat attgattctt tttt    3834
```

<210> SEQ ID NO 50
<211> LENGTH: 4060
<212> TYPE: DNA
<213> ORGANISM: human

<400> SEQUENCE: 50

```
atgagcaaac tcagaatggt gctacttgaa gactctggat ctgctgactt cagaagacat      60
tttgtcaact tgagtcccct taccattact gtggtcttac ttctcagtgc ctgttttgtc     120
accagttctc ttggaggaac agacaaggag ctgaggctag tggatggtga aaacaagtgt     180
agcgggagag tggaagtgaa agtccaggag gagtggggaa cggtgtgtaa taatggctgg     240
agcatggaag cggtctctgt gatttgtaac cagctgggat gtccaactgc tatcaaagcc     300
cctggatggg ctaattccag tgcaggttct ggacgcattt ggatggatca tgtttcttgt     360
cgtgggaatg agtcagctct ttgggattgc aaacatgatg gatgggaaa gcatagtaac     420 tgtactcacc aacaagatgc tggagtgacc tgctcagatg gatccaattt ggaaatgagg     480
ctgacgcgtg gagggaatat gtgttctgga agaatagaga tcaaattcca aggacggtgg     540
```

```
ggaacagtgt gtgatgataa cttcaacata gatcatgcat ctgtcatttg tagacaactt    600
gaatgtggaa gtgctgtcag tttctctggt tcatctaatt ttggagaagg ctctggacca    660
atctggtttg atgatcttat atgcaacgga aatgagtcag ctctctggaa ctgcaaacat    720
caaggatggg gaaagcataa ctgtgatcat gctgaggatg ctggagtgat ttgctcaaag    780
ggagcagatc tgagcctgag actggtagat ggagtcactg aatgttcagg aagattagaa    840
gtgagattcc aaggagaatg ggggacaata tgtgatgacg ctgggacagt tacgatgct     900 gctgtggcat gcaagcaact gggatgtcca actgccgtca cagccattgg tcgagttaac    960
gccagtaagg gatttggaca catctggctt gacagcgttt cttgccaggg acatgaacct   1020
gctatctggc aatgtaaaca ccatgaatgg ggaaagcatt attgcaatca caatgaagat   1080
gctggcgtga catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatctt atcaagtgta ctccaaaatc caggcaacaa acacatggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttgaggggg acattccctg ttctggacgt gttgaagtga agcatggtga cacgtggggc   1500
tccatctgtg attcggactt ctctctggaa gctgccagcg ttctatgcag ggaattacag   1560
tgtggcacag ttgtctctat cctggggggga gctcactttg agagggaaa tggacagatc   1620 tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccgtgtgagg gcagagtgga gctcaaaacg   1800
cttggtgcct ggggatccct ctgtaactct cactgggaca tagaagatgc ccatgttctt   1860
tgccagcagc ttaaatgtgg agttgcccct tctaccccag gaggagcacg ttttggaaaa   1920
ggaaatggtc agatctggag gcatatgttt cactgcactg gactgagca gcacatggga   1980 gattgtcctg taactgctct aggtgcttca ttatgtcctt cagagcaagt ggcctctgta   2040
atctgctcag gaaaccagtc ccaaacactg tcctcgtgca attcatcgtc tttgggccca   2100
acaaggccta ccattccaga agaaagtgct gtggcctgca tagagagtgg tcaacttcgc   2160
ctggtaaatg gaggaggtcg ctgtgctggg agagtagaga tctatcatga gggctcctgg   2220
ggcaccatct gtgatgacag ctgggaccctg agtgatgccc acgtggtttg cagacagctg   2280
ggctgtggag aggccattaa tgccactggt tctgctcatt ttggggaagg aacagggccc   2340
atctggctgg atgagatgaa atgcaatgga aagaatccc gcatttggca gtgccattca   2400
cacggctggg ggcagcaaaa ttgcaggcac aaggaggatg cgggagttat ctgctcagaa   2460
ttcatgtctc tgagactgac cagtgaagcc agcagagagg cctgtgcagg gcgtctggaa   2520
gttttttaca atggagcttg gggcactgtt ggcaagagta gcatgtctga aaccactgtg   2580
ggtgtggtgt gcaggcagct gggctgtgca gacaaaggga aaatcaaccc tgcatcttta   2640
gacaaggcca tgtccattcc catgtgggtg gacaatgttc agtgtccaaa aggacctgac   2700
acgctgtggc agtgcccatc atctccatgg gagaagagac tggccagccc ctcggaggag   2760
acctggatca catgtgacaa caagataaga cttcaggaag gacccacttc ctgttctgga   2820
cgtgtggaga tctggcatgg aggttcctgg ggacagtgt gtgatgactc ttgggacttg   2880
gacgatgctc aggtggtgtg tcaacaactt ggctgtggtc cagctttgaa agcattcaaa   2940
```

```
gaagcagagt tggtcaggg gactggaccg atatggctca atgaagtgaa gtgcaaaggg    3000
aatgagtctt ccttgtggga ttgtcctgcc agacgctggg gccatagtga gtgtgggcac    3060
aaggaagacg ctgcagtgaa ttgcacagat atttcagtgc agaaacccc  acaaaaagcc    3120 acaacaggtc gctcatcccg tcagtcatcc tttattgcag tcgggatcct tggggttgtt    3180
ctgttggcca ttttcgtcgc attattcttc ttgactaaaa agcgaagaca gagacagcgg    3240
cttgcagttt cctcaagagg agagaactta gtccaccaaa ttcaataccg ggagatgaat    3300
tcttgcctga atgcagatga tctggaccta atgaattcct cagaaaattc ccatgagtca    3360
gctgatttca gtgctgctga actaatttct gtgtctaaat ttcttcctat ttctggaatg    3420
gaaaaggagg ccattctgag ccacactgaa aaggaaaatg ggaatttata acccagtgag    3480
ttcagccttt aagatacctt gatgaagacc tggactattg aatggagcag aaattcacct    3540
ctctcactga ctattacagt tgcatttta tggagttctt cttctcctag gattcctaag    3600
actgctgctg aatttataaa aattaagttt gtgaatgtga ctacttagtg gtgtatatga    3660
gactttcaag ggaattaaat aaataaataa gaatgttatt gatttgagtt tgctttaatt    3720
acttgtcctt aattctatta atttctaaat gggcttccta attttttgta gagtttccta    3780
gatgtattat aatgtgtttt atttgacagt gtttcaattt gcatatacag tactgtatat    3840
tttttcttat ttggtttgaa taattttcct attaccaaat aaaataaat  ttattttac    3900 tttagttttt ctaagacagg aaaagttaat gatattgaag ggtctgtaaa taatatatgg    3960
ctaactttat aaggcatgac tcacaacgat tctttaactg ctttttgtta ctgtaattct    4020
gttcactaga ataaaatgca gagccacacc tggtgagggc                           4060

<210> SEQ ID NO 51
<211> LENGTH: 4076
<212> TYPE: DNA
<213> ORGANISM: human

<400> SEQUENCE: 51
atgagcaaac tcagaatggt gctacttgaa gactctggat ctgctgactt cagaagacat      60
tttgtcaact tgagtcccttt caccattact gtggtcttac ttctcagtgc ctgttttgtc    120
accagttctc ttggaggaac agacaaggag ctgaggctag tggatggtga aaacaagtgt    180
agcgggagag tggaagtgaa agtccaggag gagtggggaa cggtgtgtaa taatggctgg    240
agcatggaag cggtctctgt gatttgtaac cagctgggat gtccaactgc tatcaaagcc    300
cctggatggg ctaattccag tgcaggttct ggacgcattt ggatggatca tgtttcttgt    360
cgtgggaatg agtcagctct ttgggattgc aaacatgatg gatggggaaa gcatagtaac    420
tgtactcacc aacaagatgc tggagtgacc tgctcagatg gatccaattt ggaaatgagg    480
ctgacgcgtg gagggaatat gttctggaa gaatagaga tcaaattcca aggacggtgg    540
ggaacagtgt gtgatgataa cttcaacata gatcatgcat ctgtcatttg tagacaactt    600
gaatgtggaa gtgctgtcag tttctctggt tcatctaatt ttggagaagg ctctggacca    660 atctggttg atgatcttat atgcaacgga aatgagtcag ctctctggaa ctgcaaacat    720
caaggatggg gaaagcataa ctgtgatcat gctgaggatg ctggagtgat tgctcaaag    780 ggagcagatc tgagcctgag actggtagat ggagtcactg aatgttcagg aagattagaa    840
gtgagattcc aaggagaatg ggggacaata tgtgatgacg gctgggacag ttacgatgct    900
gctgtggcat gcaagcaact gggatgtcca actgccgtca cagccattgg tcgagttaac    960
```

```
gccagtaagg gatttggaca catctggctt gacagcgttt cttgccaggg acatgaacct    1020
gctatctggc aatgtaaaca ccatgaatgg ggaaagcatt attgcaatca caatgaagat    1080
gctggcgtga catgttctga tggatcagat ctggagctaa gacttagagg tggaggcagc    1140
cgctgtgctg ggacagttga ggtggagatt cagagactgt tagggaaggt gtgtgacaga    1200
ggctggggac tgaaagaagc tgatgtggtt tgcaggcagc tgggatgtgg atctgcactc    1260
aaaacatctt atcaagtgta ctccaaaatc caggcaacaa acacatggct gtttctaagt    1320
agctgtaacg gaaatgaaac ttctctttgg gactgcaaga actggcaatg gggtggactt    1380
acctgtgatc actatgaaga agccaaaatt acctgctcag cccacaggga acccagactg    1440
gttggagggg acattccctg ttctggacgt gttgaagtga agcatggtga cacgtggggc    1500
tccatctgtg attcggactt ctctctggaa gctgccagcg ttctatgcag ggaattacag    1560
tgtggcacag ttgtctctat cctgggggga gctcactttg gagagggaaa tggacagatc    1620
tgggctgaag aattccagtg tgagggacat gagtcccatc tttcactctg cccagtagca    1680
ccccgcccag aaggaacttg tagccacagc agggatgttg gagtagtctg ctcaagtaag    1740
acccagaaaa catctttaat tggttctcat actgtgaaag ggacagggtt agggagtcat    1800
agctgtcttt ttctaaagcc ctgtctcctt ccaggataca cagaaattcg cttggtgaat    1860
ggcaagaccc cgtgtgaggg cagagtggag ctcaaaacgc ttggtgcctg gggatccctc    1920
tgtaactctc actgggacat agaagatgcc catgttcttt gccagcagct taatgtgga    1980 gttgcccttt ctaccccagg aggagcacgt tttggaaaag gaaatggtca gatctggagg    2040
catatgtttc actgcactgg gactgagcag cacatgggag attgtcctgt aactgctcta    2100
ggtgcttcat tatgtccttc agagcaagtg gcctctgtaa tctgctcagg aaaccagtcc    2160
caaacactgt cctcgtgcaa ttcatcgtct ttgggcccaa caaggcctac cattccagaa    2220
gaaagtgctg tggcctgcat agagagtggt caacttcgcc tggtaaatgg aggaggtcgc    2280
tgtgctggga gagtagagat ctatcatgag ggctcctggg gcaccatctg tgatgacagc    2340
tgggacctga gtgatgccca cgtggtttgc agacagctgg gctgtggaga ggccattaat    2400
gccactggtt ctgctcattt tggggaagga acagggccca tctggctgga tgagatgaaa    2460
tgcaatggaa aagaatcccg catttggcag tgccattcac acggctgggg gcagcaaaat    2520
tgcaggcaca aggaggatgc gggagttatc tgctcagaat tcatgtctct gagactgacc    2580
agtgaagcca gcagagaggc ctgtgcaggg cgtctggaag tttttttacaa tggagcttgg    2640 ggcactgttg gcaagagtag catgtctgaa accactgtgg gtgtggtgtg caggcagctg    2700
ggctgtgcag acaaagggaa aatcaaccct gcatctttag acaaggccat gtccattccc    2760
atgtgggtgg acaatgttca gtgtccaaaa ggacctgaca cgctgtggca gtgcccatca    2820
tctccatggg agaagagact ggccagcccc tcggaggaga cctggatcac atgtgacaac    2880
aagataagac ttcaggaagg acccacttcc tgttctggac gtgtggagat ctggcatgga    2940
ggttcctggg gacagtgtgt gatgactct ggacttgg acgatgctca ggtggtgtgt    3000
caacaacttg gctgtggtcc agctttgaaa gcattcaaag aagcagagtt tggtcagggg    3060 actgaccga tatggctcaa tgaagtgaag tgcaaaggga atgagtcttc cttgtgggat    3120
tgtcctgcca gacgctgggg ccatagtgag tgtgggcaca aggaagacgc tgcagtgaat    3180
tgcacagata tttcagtgca gaaaacccca caaaaagcca caacaggtcg ctcatcccgt    3240
cagtcatcct ttattgcagt cgggatcctt ggggttgttc tgttggccat ttcgtcgca    3300 ttattcttct tgactaaaaa gcgaagacag agacagcggc ttgcagtttc ctcaagagga    3360
```

```
gagaacttag tccaccaaat tcaatacaggg gagatgaatt cttgcctgaa tgcagatgat   3420
ctggacctaa tgaattcctc aggaggccat tctgagccac actgaaaagg aaaatgggaa   3480
tttataaccc agtgagttca gcctttaaga taccttgatg aagacctgga ctattgaatg   3540
gagcagaaat tcacctctct cactgactat tacagttgca tttttatgga gttcttcttc   3600
tcctaggatt cctaagactg ctgctgaatt tataaaaatt aagtttgtga atgtgactac   3660
ttagtggtgt atatgagact ttcaagggaa ttaaataaat aaataagaat gttattgatt   3720
tgagtttgct ttaattactt gtccttaatt ctattaattt ctaaatgggc ttcctaattt   3780
tttgtagagt ttcctagatg tattataatg tgtttatttt gacagtgttt caatttgcat   3840
atacagtact gtatattttt tcttatttgg tttgaataat tttcctatta ccaaataaaa   3900
ataaatttat ttttacttta gttttttctaa gacaggaaaa gttaatgata ttgaagggtc   3960
tgtaaataat atatggctaa ctttataagg catgactcac aacgattctt taactgcttt   4020
ttgttactgt aattctgttc actagaataa aatgcagagc cacacctggt gagggc         4076

<210> SEQ ID NO 52
<211> LENGTH: 1714
<212> TYPE: DNA
<213> ORGANISM: human

<400> SEQUENCE: 52
tgccgccaga gtaaagcttt ctacccttta ctccctgcaa agaaacaaga gtgcttatcc     60
cagctaagct ccagggtaat gttatcatga cagcttcaac ttttagacca caggcaaatg    120
ctttgttaaa actctatgct ggtcattccc ttcaggattt ggcactcacc aacatacccct   180 tctttcaagt gaaaaggcat ctcttttaat ggtcctgacc tttggaatag aagcatgta    240 ccctggacag agcacttcaa actagaggaa ccataaatcc atggctaacc ttgacaaata   300
cactgaaaca ttcaagatgg gtagcaacag taccagcact gctgagattt actgtaatgt   360
cactaatgtg aaatttcaat actccctcta tgcaaccacc tatatcctca tattcattcc   420
tggtcttctg gctaacagtg cagccttgtg ggttctgtgc cgcttcatca gcaagaaaaa   480
taaagccatc attttcatga tcaacctctc tgtggctgac cttgctcatg tattatcttt   540 accccctccgg atttactatt acatcagcca ccactggcct ttccagagag cccttttgcct  600 gctctgcttc tacctgaagt atctcaacat gtatgccagc atttgtttcc tgacgtgcat   660
cagtcttcaa aggtgctttt ttctcctcaa gcccttcagg gccagagact ggaagcgtag   720
gtacgatgtg ggcatcagtg ctgccatctg gatcgttgtg gggactgcct gtttgccatt   780
tcccatcctg agaagcacag acttaaacaa caacaagtcc tgctttgctg atcttggata   840
caagcaaatg aatgcagttg cgttggtcgg atgattaca gttgctgagc ttgcaggatt   900
tgtgatccca gtgatcatca tcgcatggtg tacctggaaa actactatat ccttgagaca   960
gccaccaatg gctttccaag ggatcagtga gaggcagaaa gcactgcgga tggtgttcat  1020
gtgtgctgca gtcttcttca tctgcttcac tccctatcat attaacttta ttttttacac  1080
catggtaaag gaaaccatca ttagcagttg tcccgttgtc cgaatcgcac tgtatttcca  1140 cccttttttgc ctgtgccttg caagtctctg ctgccttttg gatccaattc tttattactt  1200
tatggcttca gagtttcgtg accaactatc ccgccatggc agttctgtga cccgctcccg  1260
cctcatgagc aaggagagtg gttcatcaat gattggctaa aattaagata tctctttaat  1320
tacgcctttg tttacctacg ttccttgtct ttttccaaag gccagaattg tcaaccaatt  1380
```

| | | | |
|---|---|---|---|
| tctttaattg | aacattgtaa | aaaacaggaa | taagtactttt tgtgtaatat tcacagtcaa | 1440 |
| caggggtgtg | atggtgaagg | cagagtgtga | aaaacgtgag agaggaagag aaaatagatt | 1500 |
| tacctgattc | ctctttaaaa | ttcaagccac | tttcttattt aagaaaccta gatcaagttt | 1560 |
| ttacagatgt | aaataaaagt | tgaatagttt | accttaaatt tttttcaata agtaagttat | 1620 |
| tgttaataat | gcacagtaaa | tatgtgaatt | ttcctagat gtaaaaaaaa aaatctttca | 1680 |
| tataaagacc | ttaaattctg | agtgagagta | aaaa | 1714 |

<210> SEQ ID NO 53
<211> LENGTH: 1597
<212> TYPE: DNA
<213> ORGANISM: human

<400> SEQUENCE: 53

| | | | | |
|---|---|---|---|---|
| tttgtgcaaa | taaggtttct | gtggtgagac | accagataaa ctcaacttcc tctttcaaca | 60 |
| acaaatgtgt | cagttatcag | caggatccat | gccgccagag taaagctttc tacccttttac | 120 |
| tccctgcaaa | gaaacaagag | tgcttatccc | agctaagctc cagggaacca taaatccatg | 180 |
| gctaaccttg | acaaatacac | tgaaacattc | aagatgggta gcaacagtac cagcactgct | 240 |
| gagatttact | gtaatgtcac | taatgtgaaa | tttcaatact ccctctatgc aaccacctat | 300 |
| atcctcatat | tcattcctgg | tcttctggct | aacagtgcag ccttgtgggt tctgtgccgc | 360 |
| ttcatcagca | agaaaaataa | agccatcatt | ttcatgatca acctctctgt ggctgacctt | 420 |
| gctcatgtat | tatctttacc | cctccggatt | tactattaca tcagccacca ctggcctttc | 480 |
| cagagagccc | tttgcctgct | ctgcttctac | ctgaagtatc tcaacatgta tgccagcatt | 540 |
| tgtttcctga | cgtgcatcag | tcttcaaagg | tgcttttttc tcctcaagcc cttcagggcc | 600 |
| agagactgga | agcgtaggta | cgatgtgggc | atcagtgctg ccatctggat cgttgtgggg | 660 |
| actgcctgtt | tgccatttcc | catcctgaga | agcacagact taaacaacaa caagtcctgc | 720 |
| tttgctgatc | ttggatacaa | gcaaatgaat | gcagttgcgt tggtcgggat gattacagtt | 780 |
| gctgagcttg | caggatttgt | gatcccagtg | atcatcatcg catggtgtac ctggaaaact | 840 |
| actatatcct | tgagacagcc | accaatggct | ttccaaggga tcagtgagag cagaaagca | 900 |
| ctgcggatgg | tgttcatgtg | tgctgcagtc | ttcttcatct gcttcactcc ctatcatatt | 960 |
| aactttatttt | tttacaccat | ggtaaaggaa | accatcatta gcagttgtcc cgttgtccga | 1020 |
| atcgcactgt | atttccaccc | ttttttgcctg | tgccttgcaa gtctctgctg ccttttggat | 1080 |
| ccaattcttt | attactttat | ggcttcagag | tttcgtgacc aactatcccg ccatggcagt | 1140 |
| tctgtgaccc | gctcccgcct | catgagcaag | gagagtggtt catcaatgat tggctaaaat | 1200 |
| taagatatct | ctttaattac | gcctttgttt | acctacgttc cttgtctttt tccaaaggcc | 1260 |
| agaattgtca | accaatttct | ttaattgaac | attgtaaaaa acaggaataa gtacttttgt | 1320 |
| gtaatattca | cagtcaacag | gggtgtgatg | gtgaaggcag agtgtgaaaa acgtgagaga | 1380 |
| ggaagagaaa | atagatttac | ctgattcctc | tttaaaattc aagccacttt cttatttaag | 1440 |
| aaacctagat | caagttttta | cagatgtaaa | taaagttga atagtttacc ttaaattttt | 1500 |
| ttcaataagt | aagttattgt | taataatgca | cagtaaatat gtgaattttt cctagatgta | 1560 |
| aaaaaaaaa | tctttcatat | aaagacctta | aattctg | 1597 |

<210> SEQ ID NO 54
<211> LENGTH: 4661
<212> TYPE: DNA
<213> ORGANISM: human

<400> SEQUENCE: 54

```
cgctcccctc agctcctgca gtgctaatta agggagggag cagcgggag  cttgcagtga      60
ccaagagggt gttgaggcta ggaggccacg ataaacagga tacgataaaa gtccttaacc     120
aagacgcaga tgggaagaag cgttagagcg agcagcactc acatctcaag aaccagcctt     180
tcaaacagtt tccagagatg gattatccta ctttactttt ggctcttctt catgtataca     240
gagctctatg tgaagaggtg ctttggcata catcagttcc ctttgccgag aacatgtctc     300
tagaatgtgt gtatccatca atgggcatct taacacaggt ggagtggttc aagatcggga     360
cccagcagga ttccatagcc attttcagcc tactcatgg  catggtcata aggaagccct     420
atgctgagag ggtttacttt ttgaattcaa cgatggcttc caataacatg actcttttct     480
ttcggaatgc ctctgaagat gatgttggct actattcctg ctctctttac acttacccac     540
agggaacttg gcagaaggtg atacaggtgg ttcagtcaga tagttttgag gcagctgtgc     600
catcaaatag ccacattgtt tcggaacctg gaaagaatgt cacactcact tgtcagcctc     660
agatgacgtg gcctgtgcag gcagtgaggt gggaaaagat ccagcccgt  cagatcgacc     720
tcttaactta ctgcaacttg gtccatggca gaaatttcac ctccaagttc ccaagacaaa     780
tagtgagcaa ctgcagccac ggaaggtgga gcgtcatcgt catccccgat gtcacagtct     840
cagactcggg gctttaccgc tgctacttgc aggccagcgc aggagaaaac gaaaccttcg     900
tgatgagatt gactgtagcc gagggtaaaa ccgataacca atataccctc tttgtggctg     960
gagggacagt tttattgttg ttgtttgtta tctcaattac caccatcatt gtcattttcc    1020
ttaacagaag gagaaggaga gagagaagag atctatttac agagtcctgg gatacacaga    1080
aggcacccaa taactataga agtcccatct ctaccagtca acctaccaat caatccatgg    1140
atgatacaag agaggatatt tatgtcaact atccaacctt ctctcgcaga ccaaagacta    1200
gagtttaagc ttattcttga catgagtgca ttagtaatga ctcttatgta ctcatgcatg    1260
gatctttatg caatttttt  ccactaccca aggtctacct tagatactag ttgtctgaat    1320
tgagttactt tgataggaaa aatacttcat tacctaaaat cattttttcat agaactgttt    1380
cagaaaacct gactctaact ggtttatata caaagaaaa  cttactgtat catataacag    1440
aatgatccag gggagattaa gctttgggca agggctattt accagggctt aaatgttgtg    1500
tctagaatta agtatgggca taaactggct tctgaatccc tttccagagt gttggatcca    1560
tttccctggt cttggcctca ctctcatgca ggctttcctc ttgtgttggc aagatggctg    1620
ccaactcttg gcaattcata catccttgtt tctgtctggt agagagtttg cttctcaaat    1680
ggagcaaaca aatttgatta ttttttcatt gttaaatagg caacatgacc agaaaggatg    1740
gaatggctta agtaaactaa gggttcactt ctagagctga gaagcagggt caaagcacaa    1800
tactgggcaa ttcagagcat ggttagaaga ggaaagggga gtctcaaagc tggagagttt    1860
accaacaaat attgactgca gtgattaacc aagacatttt tgttaactaa aaagtgaaat    1920
atgggatgga ttctagaaat ggggtatctc tgtccatact tctagaatcc actctatcag    1980
catagtccag aagaatacct ggcagtagaa gaaatgaata ttcaagagga agataaatgc    2040
gagagggcaa tcctttacta ttctcatatt tatttatctc tcattctgta tagaattctt    2100
gccgccatcc caggtctagc cttaggagca aatgtagtag atagtcgaat aataaataac    2160
ttaatgtttt ggacatattt tgtctacttt tgagaattat ttttaatatg taaattctct    2220
caaagggtc  aggcacctag ttattatttt ttaatgatta tgtgaaagtt gaatataata    2280
```

```
taccactaaa agtgacagtt gaaagtggtg gcataggacg gtagggtaga aatttgggag    2340
ggaaaaaaga aattgggagg gtacaggcaa caggagaaag gaatcaaacc acagaaaaat    2400
acaaagggaa acttctgctt cactattcag acaaagacag ccctaatgac atcaccaaca    2460
gtcaaagcaa ttagagacca tacctaatat tgtttaaatt ctagatgtag gctaacaatg    2520
aaaagtattt gccaaactga ataaaactgt catggttacc ttgaaaggac aatggttatt    2580
gttaaatata gtgatcattc atgtctaaaa gattcattat ttatctctaa agatttctaa    2640
agaccaccat ctagaaaaga ttcattatga aggctgtatt taaatatcaa agttgtggac    2700
ttcatgataa tcttaaataa agcaaatcca aattctcctg ttgcctagac agattctaag    2760
atgtaattta cacttttaag ctaattagtg agtattttat gattttagcc ttaaacacca    2820
tgtatgccaa ataatgcact tgttttgtga attacagaaa tggtaagtgc ccacatttct    2880
gtgaattata aaatttgtga gtttctttta acccttttca ggagtgaaaa aataaaaacg    2940
accatttcct ggttgtgctt aagtatatgc aagaagggta aactctcatt tttattatgt    3000
ttgcttaaag atcttttat acctggattc atgaaatgtt tccacaaata tattagtgta    3060
acaaacttga aaggcagttt acaagaaagc actctactat cagatcaatc aaagattctg    3120
tgagtgaatt tattggtttg catggtgaag caagcttagc atcaattaaa aggtaaataa    3180
tttcttttct gaatggtaaa gacaatcaaa atattacttt ctggaaaact ccaataacca    3240
aattctcaat gattagtgta tgtgagcagg aaaacatttt tacagttgta gtatggggaa    3300
atataaatcc aattttaaga gagaaaatta tgactgggtg tggaagggac agtatagtca    3360
gataccattg tcatggtggt ttttactggg aacttcatga aagactttg tagcaaacca    3420 ctgcagtatt gcaaagcctc cagaacattt ggaacttgtc tcttttttcct tgtgtgtgtt    3480 tgtgtttttg gtctctcatt caaaatattg atgagaacta tttactctgt cctttcttct    3540
ctatatattc ttcctctaca gagtgtaggg tttttttcagg aatttggagc catctgaagt    3600
cctcccaaaa attctctgac gtcttctgat gctcctgtta taccctcagg ggtaatgctt    3660
gtgaaattcc attcattcat tttctttctc tggacatctt tacttaccaa agcactttca    3720
ttgtcatctt tttaacatca ttcttaattc gtgatagtt tgggactctc cctagtgtat    3780
gtttctcccc ctctactctt ttgcacctat gattctgatt gttactaaga aagcagatga    3840
aaaacagatc cacagaataa acgatcagaa ttccagtaaa ttctatttta aatacagata    3900 cttttacaa gttgctgctt tggaagcaaa atgcttctta agttttacat atatatatat    3960
atatatacat atatatatac acatataatt tatcgatg gataatacat taagaatcta    4020
tgcttccttt gaatgccatt aatatttatg ttaaagtaac caatgaaagg aaattacttt    4080
gttataataa gataggaaga cttgttaatg gagtacacag ttttgtcagg gaaagaacac    4140
atcttattga actatgatga ctatgcattg actatattat tataagagat accttcaaac    4200
tttatttaaa gaactttagg tataatatgt tgagaaaata aaatagaaat ttcatttact    4260
tgtaatcatg cttaaaatgg gaggcaggta ggtgaagata taattttag taaaaactcc    4320 aatttatgtt ttaagtaatt cagtgtatta ctaaaatact atatatataa acttaaaata    4380
catgggttat caatttaaaa gacaaagtaa gtaaaaatac ttttagtagg cattcgtgga    4440
ttgtgaacat ccaagttata ttggtttgta tagaatggca ttaagtaaaa attacagctg    4500
tataacagta gttttctaaa ttgagagagt ccacattgta attagagatc actgtgacca    4560
aaatgcttct ccttgattta taatgatgta ctgtatttg tactgctat atgaaatttc    4620 agcaagattg acgatattat aaagatgctt ataaagtgta a                        4661
```

<210> SEQ ID NO 55
<211> LENGTH: 2013
<212> TYPE: DNA
<213> ORGANISM: human

<400> SEQUENCE: 55

| | | | | | |
|---|---|---|---|---|---|
| caagtgagct | gcccaccttg | gcctcccaaa | gtgttgggat | tacaggcgtg | agccaccaca | 60 |
| cccagcaaaa | tttctaacaa | gctctcaaat | gatgctgatg | ttgctggttg | gggtggaggt | 120 |
| ggggcatacc | ttgagagcca | ctagattaga | ccaggggttg | gcgtattatg | gcagggccag | 180 |
| tcactgtgtt | ttataaaatt | ctattggtac | atagtttctg | ctgtctcttt | aaatattgtc | 240 |
| tgtggctgct | tttggcagag | ttgagcatta | gagacagatt | acatgggccc | caaacttaaa | 300 |
| atatttactg | tttgaccatt | ttaagaaaaa | gtttatttaa | ccttatcccc | tttttctttc | 360 |
| tctctctctc | tctctctttc | cttccttcct | tccttccttc | ttttttttttc | tgagacggag | 420 |
| tcttactctg | tgcccaggct | agagtgcagt | ggcatgatct | cggctcactg | caacctccac | 480 |
| ctcccgggtt | caagcgattc | tcctgcctca | gcctctcaag | tagctgggat | tacaggccgg | 540 |
| ctgcctaccc | tccagactgt | ccgctatggc | tccaaggctg | ttacccgcca | ccgtcgtgtg | 600 |
| atgcactttc | agcggcagaa | gctgatggct | gtgactgaat | atatccccc | gaaaccagcc | 660 |
| atccacccat | catgcctgcc | atctcctccc | agcccccac | aggaggagat | aggcctcatc | 720 |
| aggcttctcc | gccgggagat | agcagcagtt | ttccaggaca | accgaatgat | agccgtctgc | 780 |
| cagaatgtgg | ctctgagtgc | agaggacaag | cttcttatgc | gacaccagct | gcggaaacac | 840 |
| aagatcctga | tgaaggtctt | ccccaaccag | gtcctgaagc | ccttcctgga | ggattccaag | 900 |
| taccaaaatc | tgctgcccct | ttttgtgggg | cacaacatgc | tgctggtcag | tgaagagccc | 960 |
| aaggtcaagg | agatggtacg | gatcttaagg | actgtgccat | tcctgccgct | gctaggtggc | 1020 |
| tgcattgatg | acaccatcct | cagcaggcag | ggctttatca | actactccaa | gctccccagc | 1080 |
| ctgcccctgg | tgcaggggga | gcttgtagga | ggcctcacct | gcctcacagc | ccagacccac | 1140 |
| tccctgctcc | agcaccagcc | cctccagctg | accaccctgt | tggaccagta | catcagagag | 1200 |
| caacgcgaga | aggattctgt | catgtcggcc | aatgggaagc | cagatcctga | cactgttccg | 1260 |
| gactcgtagc | cagcctgttt | agccagcccc | gcgcataaat | acactctgcg | ttattggctg | 1320 |
| tgctctcctc | aatgggacat | gtggaagaac | ttggggtcgg | ggagtgtgtt | tgtcacttgg | 1380 |
| ttttcactag | taatgatatt | gtcaggtata | gggccacttg | gagatgcaga | ggattccatt | 1440 |
| tcagatgtca | gtcaccggct | tcgtccttag | ttttcccaac | ttgggacgtg | ataggagcaa | 1500 |
| agtctctcca | ttctccaggt | ccaaggcaga | gatcctgaaa | agatagggct | attgtcccct | 1560 |
| gcctccttgg | tcactgcctc | ttgctgcacg | ggctcctgag | cccaccccct | tggggcacaa | 1620 |
| cctgccactg | ccacagtagc | tcaaccaagc | agttgtgctg | agaatggcac | ctggtgagag | 1680 |
| cctgctgtgt | gccaggcttt | gtgctgagtg | ctgtacatgt | attagttcct | ttactgctga | 1740 |
| ccacattgta | cccatttcac | agagaaggag | cagagaaatt | aagtggcttg | ctcaaggtca | 1800 |
| tgcagttagt | aagtggcaga | acagggactt | gaaccaagcc | ctctgctctg | aagaccgcgt | 1860 |
| cctgaatttc | ttcactagag | cttcctcatc | aggttaccca | gaagtgggtc | ccatccacca | 1920 |
| tccaggtgtg | cttggatgtt | agttctccac | cctcgaggtg | tacgctgtga | aaagtttggg | 1980 |
| agcactgctt | tataataaaa | tgaaatatat | tct | | | 2013 |

<210> SEQ ID NO 56

<211> LENGTH: 1725
<212> TYPE: DNA
<213> ORGANISM: human

<400> SEQUENCE: 56

```
gtggagatgg ctgcggccgt ggcggggatg ctgcgagggg gtctcctgcc ccaggcgggc      60
cggctgccta ccctccagac tgtccgctat ggctccaagg ctgttacccg ccaccgtcgt     120
gtgatgcact ttcagcggca gaagctgatg gctgtgactg aatatatccc cccgaaacca     180
gccatccacc catcatgcct gccatctcct cccagccccc cacaggagga gataggcctc     240
atcaggcttc tccgccggga gatagcagca gttttccagg acaaccgaat gatagccgtc     300
tgccagaatg tggctctgag tgcagaggac aagcttctta tgcgacacca gctgcggaaa     360
cacaagatcc tgatgaaggt cttccccaac caggtcctga gcccttcct ggaggattcc      420
aagtaccaaa atctgctgcc ccttttgtg gggcacaaca tgctgctggt cagtgaagag      480
cccaaggtca aggagatggt acggatctta aggactgtgc cattcctgcc gctgctaggt     540
ggctgcattg atgacaccat cctcagcagg cagggcttta tcaactactc caagctcccc     600
agcctgcccc tggtgcaggg ggagcttgta ggaggcctca cctgcctcac agcccagacc     660
cactccctgc tccagcacca gcccctccag ctgaccaccc tgttggacca gtacatcaga     720
gagcaacgcg agaaggattc tgtcatgtcg gccaatggga agccagatcc tgacactgtt     780
ccggactcgt agccagcctg tttagccagc cctgcgcata aatacactct gcgttattgg     840
ctgtgctctc ctcaatggga catgtggaag aacttggggt cggggagtgt gtttgtcact     900
tggttttcac tagtaatgat attgtcaggt atagggccac ttggagatgc agaggattcc     960
atttcagatg tcagtcaccg gcttcgtcct tagttttccc aacttgggac gtgataggag    1020
caaagtctct ccattctcca ggtccaaggc agagatcctg aaaagatagg ctattgtcc     1080
cctgcctcct tggtcactgc ctcttgctgc acgggctcct gagcccaccc ccttggggca    1140
caacctgcca ctgccacagt agctcaacca agcagttgtg ctgagaatgg cacctggtga    1200
gagcctgctg tgtgccaggc tttgtgctga gtgctgtaca tgtattagtt cctttactgc    1260
tgaccacatt gtacccatt  cacagagaag gagcagagaa attaagtggc ttgctcaagg    1320
tcatgcagtt agtaagtggc agaacaggga cttgaaccaa gccctctgct ctgaagaccg    1380
cgtcctgaat tcttcacta  gagcttcctc atcaggttac ccagaagtgg gtcccatcca    1440
ccatccaggt gtgcttggat gttagttctc caccctcgag gtgtacgctg tgaaaagttt    1500
gggagcactg ctttataata aaatgaaata tattctactt cctttatttt gtggtttaca    1560
cggttgtcct ccctctaaac ttactctcag gggcttctct gtcatctgac tttcctcact    1620
cttgcttccc ttcctaggaa aatcctcttc ccctatacct gttcccacaa atggcatccc    1680
gcgcatgctt gccctattaa aggcagctga cagctgtacc cacta                    1725
```

<210> SEQ ID NO 57
<211> LENGTH: 7665
<212> TYPE: DNA
<213> ORGANISM: human

<400> SEQUENCE: 57

```
ggccgacccg gctcgccagc tccacgctcg gctccagact ccggcatttc ctccccgcta      60
gctggcgcgg cctcgcctcc ccctcggaag aggaaactcc cggggtccga gtaacagggt     120
caggcgcgga gaggagcggc gggagagcca ggagggccgc ccagggtagg aggcgagcca     180
ggccgggcca gaagctggcc gacggcgcg  cgcgggggcg ccgggcgggg agggccgctg     240
```

```
ggccggactc agcgcgcagc cggggcaggg cgcggcccgg ggcccgagag cgcagggcgg    300
gccgcagctg gaaggaacac ttgagctggg agaggaggcc gagctggagg gcggcctccc    360
tcgggcctgc gttcgggaag ccgccgcgga ggaggagacg gggacagcgg ggctgcccgg    420
gcgctgtgcg catgctgggc ttgggtcgcc gccggggctt gccccctggg ctgctcggcc    480
accgccgccc cgggcgcccg gcatgtcggt gcactacacc ctcaatctac gcgtcttctg    540
gccccctggtg accggcctgt gcaccgccct ggtgtgcctc taccatgtcc tgcggggaag    600
cgggggcgcc cgggccgagc ccgccgacgg cgtggatggc ggcttcccgt tgcttaaggt    660
ggccgtcctg ctcctcctca gctatgtcct cctgcgctgt cgccacgctg tccggcagcg    720
cttcctgccc gggtctcccc gtctggaggg tcacgccgcc ttctcctcga cacttccg     780
agagccgggc ctcagcatcc tgctggagag ttactacgag catgaggtgc gcctgtctcc    840
gcacgtgttg ggccacagca aggcgcacgt gagccggatc gtgggcgagc tggtgcgggc    900
tggccgcgcc cggggtccc ccggtctcat tcctgggggga cgctggcct tggccttccg    960
cggagacttc atccaggtgg gcagcgccta cgagcaacat aaaatccgcc ggcccgacag   1020
cttcgacgtg ctggtgccac tgcgcctccc gccgcttgtg cgctggagc cacgagcct    1080
gggcgaggag ccagcgctgg ccccggcctt ccgcggctgc ttcttgtgcg ccctcaaggc   1140
accaccctca ccatcggggg cctcgggggg ccactggctt cgggactgca aacccttgc    1200
tgatgccttc tgcgtggatg tgcgcgggcg gcgtcacctc tctgctactc tggtgctgcg   1260
ctggttccag tcgcatctgc agcgctcctt ggccactgtg cgttacagcc tggaggggcg   1320
ctgtcgggtc accttgaccc caggtggcct ggaacagccc cccaccttac acatcttgcc   1380
ctgccgcact gactcaggct gctgccgcct ttctatggct gtgcgtctca tccccgctgt   1440
ccatctggga gatgggtct ccttgtggc gccaccacg ccaccttgc ccagcgcgcc       1500
cctgttggag ctccctgagg gcctgcgtgc ggaggcactg tggggtgtga acacagcacg   1560
ccaggagcag aagctgctga gttggctgca ggaacgggca gctccaggtg cctgctacct   1620
caagtgcctg cagttgctta aggctctgcg cgatctgggg gcccgtgggc tggactcagc   1680
ggccgccacc cagtggggac gcatcctatc ctcatatgtg ctcaagacag tgctgctggc   1740
agtgctgctg cgcaagggggg cccctgggca aggctgggac gaggagcacc tgggaaggtg   1800
tttggaggag ttggtgcagt tccttaggga ctgcctgctg cgacgccata cgctcttcca   1860
ctgcgtcctg ggccctggtg gggcggctgc cgaggtgggt cccctgccca aggcactgag   1920
ggaagccgcc ccagttgacc tcctggccgc tttcgacggg cacgcccggg aacttgcagc   1980
agcgcggttg ctgtccacgt ggcaaaggct gccccagctt ctccgggcct acggggggtcc   2040
ccgctacctt gccaggtgcc ccccaccccg gagtcagcgc acccagggct tccttgaagg   2100
tgaaccgtaa accctgacag cacccccacc tgaccaaatg ctcctaaagc ctttcccact   2160
gggtgggggt gggaatggcg gtgaagccag ttaaatgcaa gattgcagaa ggcattggaa   2220
aatttggtgg ctgccacaag ctttagtggc ttaaatatca ccttctcgct tcacagtcca   2280
gtataatatg acatcttcac acccactaga gtgtcctggg caaaccatgg aagacatcc    2340
aacaggagac ccaagaattg gttcaaatat tgttctgtgt agacggattc tgtagaagga   2400
tgtggctttt agagaagtcc agtagaagaa gcaagaacta gctgcaggga agttccttc    2460
tgtcggtttt tagacacaga tctctctgcc caaattaaaa aaaacaaaa caaaacacta    2520
aagttttga cacaattact tgctaggtac tgggttcctg attgtctta aaagaaaaa     2580
```

```
tctgaatctt tatttgcaac tggaattgaa gttctatttt aggggctaat gtttagagga    2640
acataatttc cactgttcaa attaatatta atgtattttt aaaatggtgc aatcacaggt    2700
gtttgacaag attgtcaaca agttaagtca catagatgga aaggcaatcg agagttggtt    2760
agagaagctt ccagagaaaa tagcacttta tattgatcaa ttcactcatt ttgtggtaat    2820
tgctagcacc aagcattgca tctgaaaggg aagccagtta tatttattat taaatgtaca    2880
accttgaaaa gcagccagca tgcttgccta actaacatcg ccgcaggcca caagctggga    2940
tatgtacctg tccgtcaaca tccattcatt aaactaccta ctaccagcca gagatgtctg    3000
gaaccaaagt agcaaccaaa tacatattca agacaacact ggtgaaggca taaaacatgt    3060
tggctttgga gaaagatgtg ttttaggctt tgcctgtaaa ggtgtttctc caaggctggc    3120
tgctggctgg agacagaaaa cttttttgtt ttaaggtttt tagcaaactc cttcacaaag    3180
agatttcttt ctgagcttaa tgagctaatg aagaggaaat gcctgctgct tagcatgtgg    3240
tttgtgctgg gtctctaacc attgatggtt cttccttgtc caggcagtct tacgtggtcc    3300
aagagacctg ttgattcagc acaggtcttg caaaacattt cacttatagt tcagtatctt    3360
gggctctgtg cttgaagatc agttactccc tggtcgtggg cagaggagac aaattaggaa    3420
aagagcaagg gagacagccc ttgacggcag tctgtctctt ttctctttag gtgtcagtat    3480
caccaggttg ggtgtatttt gcagctggga ggagccggtc ctggaattct tccttgttct    3540
cccaaattta taacagtcct caattgcagt ttaagttcag catggcccct catctgcttg    3600
cctgattgga aatgcagcca gtccaagtgt tacaaattgg dattttttg ttttctaaat    3660 aaaaacatgt acttcctcag actcttaaag ctaaatttg gaagacagaa atgcctatgt    3720
gaatagaatc attgttgaag ttctgagctc ttttgaggga actctataag ccttctttct    3780
ttaggggatc cacttgcctg ctgtgggaaa tcatagtgag tgatttacag gaatccttct    3840
cctccaagct gcattggctt cttatatcct ttgcgacctt gggctgaaag agaaacagct    3900
gcaaatgttg tgctgtctct ttgaggttgt cttggggaca gttccccgca aaggtcattc    3960
ctagcttttg aggtcaatgt tgggtcataa ggtactgcat tgtgcaaaga agtcagtctg    4020
ctaactttat gcaaagatag aaactgcacg gtatttttta aaattagttt ttaaaataaa    4080
tgccaagagt agatcttata tatatatata tgtatacata ttttatatat atatatattt    4140
ccatactcaa ccacaacttc ctctgtactc attgtttact acagtggggg acatcaaggg    4200
ttggaaggat tataaagctt taaggctggg cgtggtggct cacgcctgta atcccagcac    4260
tttgggaggc gaggtgggcg gatcacctga ggtcaggagt tcaagaccag cctagccaac    4320
atagtgaaac tctgtctcta ctaaaaaata caaaaattag ctgggcgtgg tggcgggcgc    4380
ctgtaatccc agatactcgg gaggctaagg caggagaatc acttgaaccc gggaggtgaa    4440
ggttgcagag agccaagatc acaccactgc actccagcct gggtgaccga gcgagactcc    4500
gtctcaaaaa aaaaaaaaaa aagctttaaa aagctgaatt ttagaaatat ttctagcagt    4560
gtcagtgagt tcctcttta atagtgtttt aaagtataaa tctggtaaca tactgttctt    4620
gtagtttttt gttagttttg tttttcaggt taattaccca aagcctcatc catcctcaag    4680
gtttttaaat tttattttt taaaataaat tgtgcattgt atttgtgaat ttttaaaata    4740
ttactgtttt atttaaatgc catgctgagc aattgttctc tgtacatggt aaccaaaact    4800
tagagatttc gatcaatttt gatcaatgtt tagtaaacca aaacatgtac tgtgtacaac    4860
ggaaataata tggcatatta gccaggcatg atggttgccc aagacagtta aattaagctc    4920
aattctgtat tttattaggg ctctgttatg tccttcatct gaaatgtaca catttttggt    4980
```

```
gtatgcttgg tactggagat tcatatatgc aaatattctc atgcaagaag ttccacagta    5040
acaacagcaa aaagaaaaaa ttagttgtcc agccagtgct ggaggaaaat gtttctgggg    5100
aagatgactc agtcattttg tggcgagaca ccctttggta actcccactg accagtcttg    5160
ggagccttcc tggaatgatc gtgggctgag cggagatgtt ttttgcaaaa tgaaactgaa    5220
gctgaaagaa aggagaattc gagtgaacca agagaaatcc aaagacctgg ggaaggagga    5280
cttaagatga aagtgaagca agagagggaa ggggaaatga agtgaaaatg gcgtgagggt    5340
gtgagagagg tttgggttag gaaacatgtt tttagtgcta tttccaacca ggggtcgcaa    5400
actcagcagc ctgtagaaac aggggtggga ggtgggggggg aagctgtgcc cacctttaaa    5460 gaggggggcca ttgctcagcc atgcagaaaa aaatggggca acaagctgga aatcaggttt    5520
ttttttttta aagtgaaact tgatgatttt taaacaagta attaaaaaaa tgtccaaaac    5580
accatgtggg ccaaacattt gtttgagcct gggggccacc agtttgcgac cactgcctta    5640
cgtagttaac accctgagta tgtatacagt catattttt gttttggata tggtagtgtt    5700
atatatactt gggggcgtga tatttgaagt catctttatc tctcagagtt aagctttatt    5760
gtagaagaaa aaaaaaaaag ttaacacagc catagataac acttaactca cagttcccag    5820
gaggacactt gatctcgaag ctgctctttt tgagtcagat cctacatcaa accacttagg    5880
gccagttttt ggcatttcct tcctggtgat ttggggtaaa cttctttgct ctgtcggagt    5940
ttgcagatga gtaatcagaa ggattgcaga ataacttgtt tctttgtatt ttattcttac    6000
atttaaatta attttggggg gttagtggta tcctagctcg tgcctttaca gggatgattg    6060
gtggctagat ttggggtgca agcttcttag gctcatacca tttcaactac caagaacaca    6120 ggttttgtt tttgttttt gagacagggt ctcagtctgt tgcccaggct ggagtgcagt    6180
ggcaagattg cagctcattg cagccttgac ctcctgggct caagcgatcc tcctgcctcg    6240
gcctcccaac tagctgggac cacaggtatg tgccactaca cccagcgaat ttttaaatta    6300
tttgtagagt cagggtctcc ctatgttgcc caggctggtc ttgaactact ggactcaagc    6360
catcctccca cctcggcctc ccaaagtgtt gggattatag gcgcgagcca ccacacctgg    6420
cctaaaagcg tcgttctgat cagacttcac ccctgaatgt ttctatcatt ttcttttctt    6480
tttttttttt tttcgagaca gagttttgct cttgttttac aggctggggt gcggtgggat    6540
gatcttggct cactgcaatc tcctcctccc aggttcaagt gattcttggg ccttagcctc    6600
ccgagtagct gggattacag gcacctgcca ccacgcctgg ctaatatata tatatatata    6660
tatatatttt tttttttttt ttttagtaga tgggggttt catcatgttg gccaggctgg    6720
tctcgaactc ctgacctcag gtgatctacc tgcctcggcc tcccaaagtg cagggattac    6780
aggtgtgagt gagccaccgc ggccggcctc tatcattttc tgactcagca gctccaccaa    6840
aattgacatc ctagcaaaca ctgtgaagga attaacctaa gtgcttccag agcatctcat    6900
gtaacctcta tggagtaagt cacttttct gtaacatgtg gcttttgacc ttgatgaaga    6960
ctttgacttc tcatccctgt ctacatggag gaagatgatt cagtggtggg gaaaatgaac    7020
ctcggtaaca tttccaatgt ccttcaagag ggaaacaagt tcagtgttat catcgtggca    7080
ttcgttagtt tttttttttt taaatcactt gtttagatac aactttattt ttttataccc    7140
acatagcaca tgactggggg gataaagcat gtataagttg ggagagggta aagaatgtgt    7200
gactatgtat acagaaaata gactaaaatg tgcagcaaaa tgatatatac tgtaatctgg    7260
tttttgaagt atctactatt ctggaatatt gttaaacaac ttttgctttt tgaaaaaaaa    7320
```

```
aggtgccttg attcagttgc gtgacttaga acattcatcc tattttattg tgattttaa      7380 tgtcttctga ccccaaactg tgttttggt tgcagtctgg cggctgcagg catagcgtcg       7440
gttttgttcc aataacagag accaaagagt taatcagata tggttcagct gctacaattg     7500
tatgattcaa aggcaattta atcaccccaa atttccatgg cccccacagt caagacctgc     7560
cattcgtttt ctcttgcagg ttggagtaaa tttgcacttt gaatcatgtg ggtcatttgg     7620
ggaccttgtt cttttctatt ttgctttatt aataaaggaa cttgt                     7665
```

<210> SEQ ID NO 58
<211> LENGTH: 1609
<212> TYPE: DNA
<213> ORGANISM: human

<400> SEQUENCE: 58

```
gtaaagagag gcacgtggtt aagctctcgg ggtgtggact ccaccagtct cacttcagtt       60
ccttttgcat gaagagctca gaatcaaaag aggaaaccaa cccctaagat gagctttcca      120
tgtaaatttg tagccagctt ccttctgatt ttcaatgttt cttccaaagg tgcagtctcc      180
aaagagatta cgaatgcctt ggaaacctgg ggtgccttgg gtcaggacat caacttggac      240
attcctagtt ttcaaatgag tgatgatatt gacgatataa aatgggaaaa aacttcagac     300
aagaaaaaga ttgcacaatt cagaaaagag aaagagactt tcaaggaaaa agatacatat     360
aagctattta aaaatggaac tctgaaaatt aagcatctga gaccgatga tcaggatatc      420 tacaaggtat caatatatga tacaaaagga aaaaatgtgt tggaaaaaat atttgatttg     480
aagattcaag agagggtctc aaaaccaaag atctcctgga cttgtatcaa cacaaccctg     540
acctgtgagg taatgaatgg aactgacccc gaattaaacc tgtatcaaga tgggaaacat     600
ctaaaacttt ctcagagggt catcacacac aagtggacca ccagcctgag tgcaaaattc    660
aagtgcacag cagggaacaa agtcagcaag gaatccagtg tcgagcctgt cagctgtcca     720
gagaaaggtc tggacatcta tctcatcatt ggcatatgtg gaggaggcag cctcttgatg     780
gtctttgtgg cactgctcgt tttctatatc accaaaagga aaaaacagag gagtcggaga    840
aatgatgagg agctggagac aagagcccac agagtagcta ctgaagaaag gggccggaag     900
ccccaccaaa ttccagcttc aacccctcag aatccagcaa cttcccaaca tcctcctcca    960
ccacctggtc atcgttccca ggcacctagt catcgtcccc cgcctcctgg acaccgtgtt    1020
cagcaccagc ctcagaagag gcctcctgct ccgtcgggca cacaagttca ccagcagaaa    1080
ggccgcgccc tccccagacc tcgagttcag ccaaaacctc cccatggggc agcagaaaac   1140
tcattgtccc cttcctctaa ttaaaaaaga tagaaactgt cttttcaat aaaaagcact     1200 gtggatttct gccctcctga tgtgcatatc cgtacttcca tgaggtgttt tctgtgtgca    1260
gaacattgtc acctcctgag gctgtgggcc acagccacct ctgcatcttc gaactcagcc    1320
atgtggtcaa catctggagt tttggtctc ctcagagagc tccatcacac cagtaaggag     1380
aagcaatata agtgtgattg caagaatggt agaggaccga gcacagaaat cttagagatt    1440
tcttgtcccc tctcaggtca tgtgtagatg cgataaatca agtgattggt gtgcctgggt   1500
ctcactacaa gcagcctatc tgcttaagag actctggagt ttcttatgtg ccctggtgga   1560
cacttgccca ccatcctgtg agtaaaagtg aaataaaagc tttgactag                1609
```

<210> SEQ ID NO 59
<211> LENGTH: 3274
<212> TYPE: DNA
<213> ORGANISM: human

<400> SEQUENCE: 59

```
gtcatgcgtg ccacgctctc ctctacgcgc cggaccctgg gatgctcttc ggccgcatcc    60
cgctgcgcta cgccatactg atgcagatgc gcttcgatgg acgcctgggc ttccccggcg   120
gattcgtgga cacgcaggac agaagcctag aggacgggct gaaccgcgag ctgcgcgagg   180
agctgggcga agcggctgcc gctttccgcg tggagcgcac tgactaccgc agctcccacg   240
tcgggtcagg gccacgcgtt gtgcccact tctatgccaa gcgtctgacg ctcgaggagc   300
tgttggctgt ggaggccggc gcaacacgcg ccaaggacca cgggctggag gtgctgggcc   360
tggtgcgagt gccctgtat acctgcggg atggtgtagg aggcctgcct accttcctgg   420
agaattcctt tattggctct gcgcgggagc agttacttga agctctccag gacttgggac   480
tgctgcagtc tggctctatt tcaggcctta agattccagc tcatcactag aggcagccct   540
ccatggaccc atgaaaactg agatgaggac cttggtacta gggagggagg aaggacgtg   600
ggaatgtttt cttattggat ctgagagatg atacatgata ccagatgaaa agaaggagaa   660
gtgtgtacca tatgttttga gcagaggacc ctccaactta tggcatcagg ggcaaaaagt   720
cacagcttat cccaggcacc ctggcaggtt ctcagagcct gcctcctccc tgtttatatg   780
cgtacagcct ggtaaccccc aggcatgcaa atatacaatc tgtaacaaca cacagcctga   840
caccttcccc tggtcatgtc cagtttaacc ttgaagtggc atttgtcaca ctaccctggt   900
ccctgattgc aaggagcttc tgaagcaagg gtgaatcctt cccacactcc tccatggttg   960
ccctccaggg tctagcccag cctatttgtt agggaggata gagaaacaga gcacccctg  1020
tgctttctga aaatagactt gctcttgtct tgagtggtga ccaaagcagt tggctcttaa  1080
aaggtgggag agcagcccaa ccaatcccca atccttttct tctgaaactg agcaggaagg  1140
gtaaggaagt ggctaggtct ccttggactg agcatggaca tgagtcctgt gaggactggt  1200
gtctctcctc tagagctttc atctttggga tgcctgagac tccgagacta tcagaaggga  1260
attgacccac cccagtctag caccaccctg ccttcacttc atctacataa aggtggtata  1320
aaaacataga ctggaggagg taatccatgg agagagaaaa agaagagggc tcaggacaag  1380
gccctgagga ggcccaatcc taaaagtttg ggcagaggga accaggcacg ttaaagaaga  1440
cagaaagcgg actatgcaga gtgcttgtga gggtttcact aaaacagagg caaaactgtc  1500
cattgaattc agtaacatga agtgtttgat gactatgatg gcagcagttt caggaagggc  1560
ggtatggaag gcaggctgta ctggttgagt gaatggaaag ttggggagta aacgtgtga  1620
gaagttggcc ttcaagggc tcaggttaat aatagagagc tatggagtca aggcatgttt  1680
aagatgggag gtagagcatg ccaatattga tggcaacagt caagatggtg tgatgagaga  1740
gatggaggg gcacaaagag gaggacccct gaaggagcag agtccatgag aaagaaggag  1800
ggatgggacc tttgtaggaa agacacagt cctgcagcct catatggctc aataaaacag  1860
aaaggggcaa gtatagaaga ttaggatgac taaattaatg gggaaatgat gaaggagttt  1920
gaatctcttc tttgtgaaat gaagtgagac tatcagctag ttgtgggtgg agtgtgttct  1980
cagaaggtat gaagtagatg ttttcctagg tgttggaaaa caggttgatt aaggcaacag  2040
cagaagggca gggcaaggct gagctctgag atggtcagtt tagagtagga tgctgggcac  2100
tcaggtgtgt gtgtgttgag tggggctctg cacacacctg tcttcccctc atcaggattc  2160
aggagctggg atgggtacac ttactgcagt gttgggtttt gccagggaa gtaaaaggag  2220
ttgagagaaa gatgggtcag ttcagaagac atacacagga gaaattgtag tgatgaaatg  2280
```

```
-continued tgcagtctaa ggtttaatct gaccaagaaa ttggaattga aaacaggagg tgactaggga    2340
gggattagga aattagaggt cttgacaaga tagaaactcc agcatggtga ggggttgggc    2400
agggaggtat atttgagcca gacaggagtg ctttggaaat tgagaggtgg agcaatctca    2460
ggtaaaggca aaatagaggg tatgacctgg ggttgctggc cagagccagg gaggagcctt    2520
aagaagtgaa atctagggtt ggcgaggctg gagggcaggg tgagcctcca catgggtgct    2580
gaagcaagaa accgacagat gttgaggaga atggtgtgac ctaggagtca gcatccttgg    2640
tgaacaagag gagtggccac aaggccagtg gcacctgcca gaggggaaag caggcatgac    2700
aggatagcat ctcccaggtg agagcctttt gaggaaggga gggtgggcag tggtctggaa    2760
gcttgatgca gagcagtgtg ggtcccactg gcagcccttg gtcttagaag aatgggagta    2820
cccagtgggg gagcagctgt acaatgaggt agactcctag aggttaatta tcatctccta    2880
atcttaccct gaccctttg  tcaaacgtta tctagattaa acctcagtat aggcaggctg    2940
caggaaatgg acattccagt ggcccctggg gttccagcct gtagcagctt catctgtgct    3000
ttgtgcactt ggttctcagt catctctgca agggaccctg acgcctggga gatcagagcc    3060
actgaccctt tatggcactg ctaacagacc ccttccctca ggtaattctg gatccagaac    3120
tcattatggg atgtaatcca ggtcaacact aataccactt ggaaggttcc gctctgtctc    3180
actctgcttg agtatcccac tgatcagtct ctcagtgcct gcctactggg cagctcatct    3240
gtccacttat tcgtattaaa tttgcttttt attt                                3274
```